(12) United States Patent
Kshirsagar et al.

(10) Patent No.: US 8,178,677 B2
(45) Date of Patent: May 15, 2012

(54) HYDROXYALKYL SUBSTITUTED IMIDAZOQUINOLINES

(75) Inventors: Tushar A. Kshirsagar, Woodbury, MN (US); Bryon A. Merrill, River Falls, WI (US); Scott E. Langer, Woodbury, MN (US); Kyle J. Lindstrom, Houlton, WI (US); Sarah J. Slania, Minneapolis, MN (US); Gregory J. Marszalek, Woodbury, MN (US); Karl J. Manske, Minneapolis, MN (US); Philip D. Heppner, Forest Lake, MN (US); Gregory D. Lundquist, Jr., Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 963 days.

(21) Appl. No.: 11/885,005

(22) PCT Filed: Feb. 22, 2006

(86) PCT No.: PCT/US2006/006223
§ 371 (c)(1),
(2), (4) Date: Jul. 25, 2008

(87) PCT Pub. No.: WO2006/098852
PCT Pub. Date: Sep. 21, 2006

(65) Prior Publication Data
US 2009/0029988 A1    Jan. 29, 2009

Related U.S. Application Data

(60) Provisional application No. 60/655,380, filed on Feb. 23, 2005.

(51) Int. Cl.
*C07D 471/00* (2006.01)
*A61K 31/535* (2006.01)
(52) U.S. Cl. ...................... 546/82; 514/222.8
(58) Field of Classification Search ............... None
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,605,899 A | 2/1997 | Gerster et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,465,654 B2 | 10/2002 | Gerster et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |

(Continued)

FOREIGN PATENT DOCUMENTS

EP        0 394 026        10/1990

(Continued)

OTHER PUBLICATIONS

Yutilov et al., Synthesis and some reactions of 4-nitroimidazo[4-5-c]pyridin-2-ones. VINITI.1978:1193-78. Russian. CAPLUS English Abstract DN 91:175261.

Wozniak et al., "The Amination of 3-nitro-1, 5-naphthyridines by Liquid Ammonia/Potassium Permanganate[1,2]. A New and Convenient Animation Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul. 1978, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

(Continued)

*Primary Examiner* — Janet Andres
*Assistant Examiner* — Heidi Reese

(57) ABSTRACT

Certain imidazoquinolines with a hydroxymethyl or hydroxyethyl substituent at the 2-position, pharmaceutical compositions containing the compounds, intermediates, methods of making and methods of use of these compounds as immunomodulators, for preferentially inducing IFN-α biosynthesis in animals and in the treatment of diseases including viral and neoplastic diseases are disclosed.

18 Claims, 2 Drawing Sheets

U.S. PATENT DOCUMENTS

| | | | |
|---|---|---|---|
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 * | 5/2008 | Gorden et al. ............ 530/300 |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,968,562 B2 | 6/2011 | Skwierczynski et al. |
| 7,968,563 B2 | 6/2011 | Kshirsager et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0155767 A1 | 7/2007 | Radmer et al. |
| 2007/0166384 A1 | 7/2007 | Zarraga et al. |
| 2007/0167479 A1 | 7/2007 | Busch et al. |

| | | |
|---|---|---|
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |
| 2008/0085895 A1 | 4/2008 | Griesgraber et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269186 A1 | 10/2008 | Griesgraber et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 92/15581 A1 | 9/1992 |
| WO | WO 92/15582 A1 | 9/1992 |
| WO | WO 02/36592 | 5/2002 |
| WO | WO 03/009852 A1 | 2/2003 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-as-triazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

* cited by examiner

HYDROXYALKYL SUBSTITUTED IMIDAZOQUINOLINES

CROSS REFERENCE TO RELATED APPLICATIONS

This application is a national stage filing under 35 U.S.C. §371 of PCT International application PCT/US2006/006223 designating the United States of America, and filed Feb. 22, 2006. This application claims the benefit under 35 U.S.C. §119(e) of U.S. provisional application Ser. No. 60/655,380, filed Feb. 23, 2005, which is incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

The present invention provides a new class of compounds which preferentially induce the biosynthesis of interferon ($\alpha$) (IFN-$\alpha$) in animals. Such compounds are of the following Formulas I, II, and III:

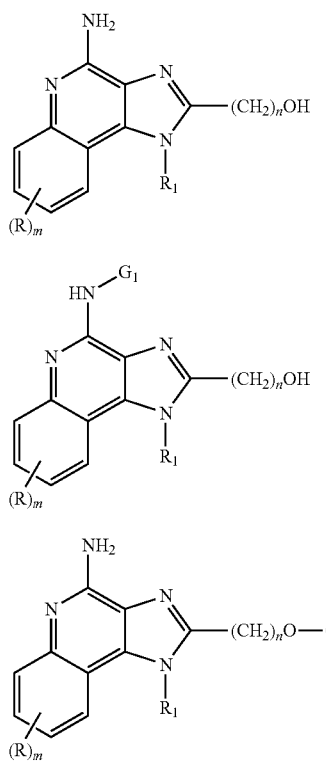

wherein R, $R_1$, $G_1$, $G_2$, m, and n are as defined below.

It has now surprisingly been discovered that the amount of TNF-$\alpha$ induced by the 2-(hydroxyalkyl) substituted compounds of the invention is substantially less than the amount of TNF-$\alpha$ induced by closely related analogs having an alkyl or alkyl ether substituent at the 2-position and that the compounds of the invention still retain the ability to induce the biosynthesis of IFN-$\alpha$. See, for example, FIGS. 1-4 below. The reduction in the amount of TNF-$\alpha$ induced is seen over a broad range of test concentrations. In some embodiments the amount of TNF-$\alpha$ induced by the compounds of the invention is at least two-fold less than the amount of TNF-$\alpha$ induced by analogs having an alkyl or alkyl ether substituent at the 2-position. In other embodiments the amount of TNF-$\alpha$ induced by the compounds of the invention is at least three-fold less than the amount of TNF-$\alpha$ induced by analogs having an alkyl or alkyl ether substituent at the 2-position. In still other embodiments the amount of TNF-$\alpha$ induced by the compounds of the invention is at least four-fold less than the amount of TNF-$\alpha$ induced by analogs having an alkyl or alkyl ether substituent at the 2-position.

As used herein "substantially less than the amount of TNF-$\alpha$" means that there is at least a two-fold reduction in the maximal TNF-$\alpha$ response as determined using the test methods described herein.

The compounds or salts of Formulas I, II, and III are especially useful as immune response modifiers due to their ability to preferentially induce interferon-$\alpha$, thus providing a benefit over compounds that also induce pro-inflammatory cytokines (e.g. TNF-$\alpha$) or that induce pro-inflammatory cytokines at higher levels.

A compound is said to preferentially induce IFN-$\alpha$ if, when tested according to the test methods described herein, the effective minimum concentration for IFN-$\alpha$ induction is less than the effective minimum concentration for TNF-$\alpha$ induction. In some embodiments, the effective minimum concentration for IFN-$\alpha$ induction is at least 3-fold less than the effective minimum concentration for TNF-$\alpha$ induction. In some embodiments, the effective minimum concentration for IFN-$\alpha$ induction is at least 6-fold less than the effective minimum concentration for TNF-$\alpha$ induction. In other embodiments, the effective minimum concentration for IFN-$\alpha$ induction is at least 9-fold less than the effective minimum concentration for TNF-$\alpha$ induction. In some embodiments, when tested according to the test methods described herein, the amount TNF-$\alpha$ induced by compounds of the invention is at or below the background level of TNF-$\alpha$ in the test method.

The invention further provides pharmaceutical compositions containing an effective amount of a compound or salt of Formulas I, II, and/or III and methods of preferentially inducing the biosynthesis of IFN-$\alpha$ in an animal, and treating a viral infection or disease and/or treating a neoplastic disease in an animal by administering an effective amount of a compound or salt of Formulas I, II, and/or III or a pharmaceutical composition containing an effective amount of a compound or salt of Formulas I, II, and/or III to the animal.

In addition, methods of synthesizing compounds of Formulas I, II, and III and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

Figure 1:
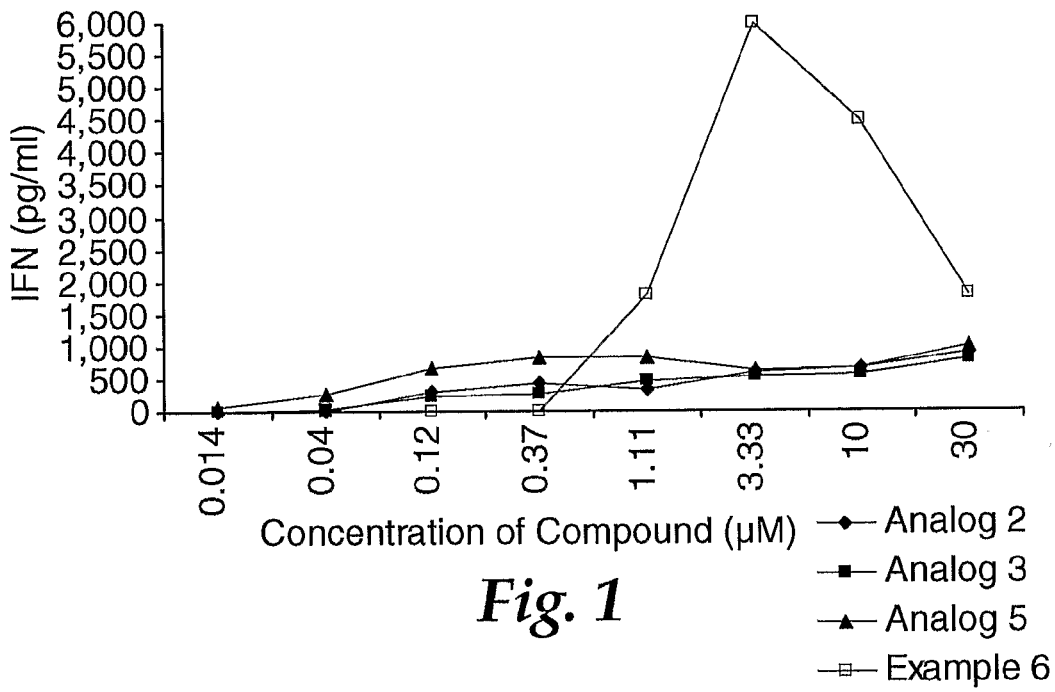
FIG. 1 shows the IFN-α dose response curves (corresponding to values shown in Table 5 below) for Example 6, Analog 2, Analog 3, and Analog 5.

The present invention provides compounds of the following Formulas I, II, and III:

wherein R, $R_1$, $G_1$, $G_2$, m, and n are as defined below; and pharmaceutically acceptable salts thereof.

In one embodiment, the present invention provides a compound of the following Formula I:

wherein:

m is 0 or 1;

n is 1 or 2;

R is selected from the group consisting of $C_{1-10}$ alkyl, $C_{1-10}$ alkoxy, halogen, and $C_{1-10}$ haloalkyl;

$R_1$ is selected from the group consisting of:

—X—Y—$R_4$,

—X—$R_5$, and

—X-Het;

X is straight chain or branched chain alkylene optionally interrupted by one —O— group;

Y is selected from the group consisting of —$S(O)_{0-2}$— and —$N(R_8)$-Q-;

$R_4$ is selected from the group consisting of hydrogen, alkyl, alkenyl, aryl, arylalkylenyl, heteroaryl, and heteroarylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo;

$R_5$ is selected from the group consisting of:

Het is selected from the group consisting of tetrahydropyranyl and tetrahydrofuranyl;

$R_6$ is selected from the group consisting of =O and =S;

$R_7$ is $C_{2-7}$ alkylene;

$R_8$ is selected from the group consisting of hydrogen, alkyl, alkoxyalkylenyl, hydroxyalkylenyl, arylalkylenyl, and heteroarylalkylenyl;

$R_{10}$ is $C_{3-8}$ alkylene;

A is selected from the group consisting of —O—, —C(O)—, —$CH_2$—, —$S(O)_{0-2}$—, and —N(Q-$R_4$)—;

Q is selected from the group consisting of a bond, —C($R_6$)—, —$S(O)_2$—, —C($R_6$)—N($R_8$)—, —$S(O)_2$—N($R_8$)—, —C($R_6$)—O—, and —C($R_6$)—S—; and a and b are independently integers from 1 to 6 with the proviso that a+b is $\leq 7$;

with the proviso that when Y is —$S(O)_{0-2}$— then X can not contain an —O— group; or a pharmaceutically acceptable salt thereof.

In another embodiment, the present invention provides a compound of the following Formula II, which is a prodrug:

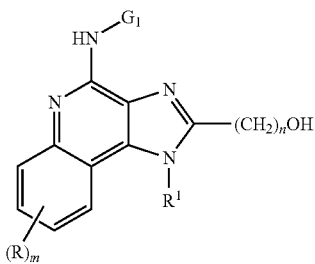

wherein:
G₁ is selected from the group consisting of:
—C(O)—R',
α-aminoacyl,
α-aminoacyl-α-aminoacyl,
—C(O)—O—R',
—C(O)—N(R")R',
—C(=NY')—R',
—CH(OH)—C(O)—OY',
—CH(O$C_{1-4}$ alkyl)$Y_0$,
—$CH_2Y_1$, and
—$CH(CH_3)Y_1$;

R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$, with the proviso that R" can also be hydrogen;

α-aminoacyl is an α-aminoacyl group derived from an α-amino acid selected from the group consisting of racemic, D-, and L-amino acids;

Y' is selected from the group consisting of hydrogen, $C_{1-6}$ alkyl, and benzyl;

$Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$alkylenyl;

$Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl;

m is 0 or 1;
n is 1 or 2;
R is selected from the group consisting of $C_{1-10}$ alkyl, $C_{1-10}$ alkoxy, halogen, and $C_{1-10}$ haloalkyl;
$R_1$ is selected from the group consisting of:
—X—Y—$R_4$,
—X—$R_5$, and
—X-Het;

X is straight chain or branched chain alkylene optionally interrupted by one —O— group;
Y is selected from the group consisting of —$S(O)_{0-2}$— and —N($R_8$)-Q-;
$R_4$ is selected from the group consisting of hydrogen, alkyl, alkenyl, aryl, arylalkylenyl, heteroaryl, and heteroarylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo;

$R_5$ is selected from the group consisting of:

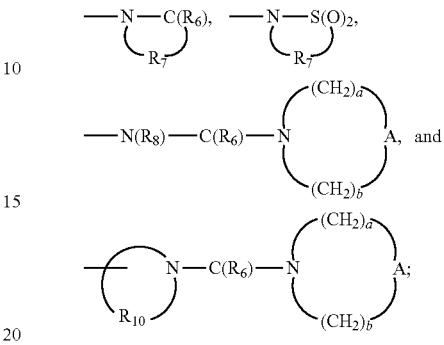

Het is selected from the group consisting of tetrahydropyranyl and tetrahydrofuranyl;
$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_{10}$ is $C_{3-8}$ alkylene;
A is selected from the group consisting of —O—, —C(O)—, —$CH_2$—, —$S(O)_{0-2}$—, and —N(Q-$R_4$)—;
Q is selected from the group consisting of a bond, —C($R_6$)—, —$S(O)_2$—, —C($R_6$)—N($R_8$)—, —$S(O)_2$—N($R_8$)—, —C($R_6$)—O—, and —C($R_6$)—S—; and
a and b are independently integers from 1 to 6 with the proviso that a+b is ≦7;
with the proviso that when Y is —$S(O)_{0-2}$— then X can not contain an —O— group; or a pharmaceutically acceptable salt thereof.

In another embodiment, the present invention provides a compound of the following Formula III, which is a prodrug:

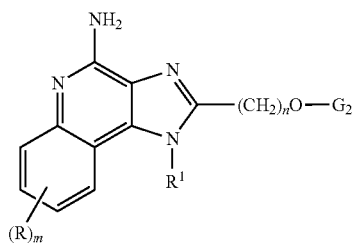

wherein:
$G_2$ is selected from the group consisting of:
—$X_2$—C(O)—R',
α-aminoacyl,
α-aminoacyl-α-aminoacyl,
—$X_2$—C(O)—O—R', and
—C(O)—N(R")R';
$X_2$ is selected from the group consisting of a bond; —$CH_2$—O—; —CH($CH_3$)—O—; —C($CH_3$)$_2$—O—; and, in the case of —$X_2$—C(O)—O—R', —$CH_2$—NH—;
R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an α-aminoacyl group derived from an α-amino acid selected from the group consisting of racemic, D-, and L-amino acids;

m is 0 or 1;

n is 1 or 2;

R is selected from the group consisting of $C_{1-10}$ alkyl, $C_{1-10}$ alkoxy, halogen, and $C_{1-10}$ haloalkyl;

$R_1$ is selected from the group consisting of:
—X—Y—$R_4$,
—X—$R_5$, and
—X-Het;

X is straight chain or branched chain alkylene optionally interrupted by one —O— group;

Y is selected from the group consisting of —S(O)$_{0-2}$— and —N(R$_8$)-Q-;

$R_4$ is selected from the group consisting of hydrogen, alkyl, alkenyl, aryl, arylalkylenyl, heteroaryl, and heteroarylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo;

$R_5$ is selected from the group consisting of:

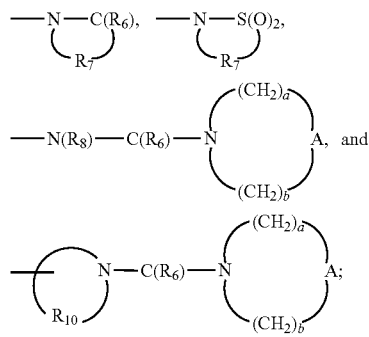

Het is selected from the group consisting of tetrahydropyranyl and tetrahydrofuranyl;

$R_6$ is selected from the group consisting of =O and =S;

$R_7$ is $C_{2-7}$ allylene;

$R_8$ is selected from the group consisting of hydrogen, alkyl, alkoxyalkylenyl, hydroxyalkylenyl, arylalkylenyl, and heteroarylalkylenyl;

$R_{10}$ is $C_{3-8}$ alkylene;

A is selected from the group consisting of —O—, —C(O)—, —CH$_2$—, —S(O)$_{0-2}$—, and —N(Q-R$_4$)—;

Q is selected from the group consisting of a bond, —C(R$_6$)—, —S(O)$_2$, —C(R$_6$)—N(R$_8$)—, —S(O)$_2$—N(R$_8$)—, —C(R$_6$)—O—, and —C(R$_6$)—S—; and a and b are independently integers from 1 to 6 with the proviso that a+b is ≦7;

with the proviso that when Y is —S(O)$_{0-2}$— then X can not contain an —O— group; or a pharmaceutically acceptable salt thereof.

Unless otherwise specified, as used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclobutyl, cyclopropylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, chlorobutyl, trifluoromethyl, 2,2,2-trifluoroethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_8$)—C(O)—N($R_8$)— each $R_8$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Y, X, $R_1$, Q, $G_1$, $G_2$, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formula I, II, or III, n is 1.
For certain embodiments of Formula I, II, or III, n is 2.
For certain embodiments of Formula I, II, or III, including any one of the above embodiments, m is 0.

For certain embodiments of Formula I, II, or III, including any one of the above embodiments, $R_1$ is —X—Y—$R_4$ wherein X is straight chain or branched chain $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —S(O)$_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl; with the proviso that when Y is —S(O)$_2$— then X can not contain an —O— group. For certain of these embodiments, as well as any one of the above embodiments, $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino]carbonyl}amino)propyl, and 2,2-dimethyl-3-(methylsulfonyl)propyl.

For certain embodiment, including any one of the above embodiments of Formulas I, II, and III, $R_1$ is —X—Y—$R_4$ wherein X is straight chain or branched chain $C_{1-8}$ alkylene which may be interrupted by one —O— group; Y is selected from the group consisting of —N($R_8$)—C(O)—, —N($R_8$)—S(O)$_2$—, —N($R_8$)—S(O)$_2$—N($R_{8a}$)—, —N($R_8$)—C(O)—N($R_{8a}$)—, and —S(O)$_2$— wherein $R_8$ is hydrogen, methyl, benzyl, or pyridin-3-ylmethyl; $R_{8a}$ is hydrogen, methyl, or ethyl, and $R_4$ is selected from the group consisting of $C_{1-7}$ alkyl, halo$C_{1-4}$ alkyl, hydroxy$C_{1-4}$ alkyl, phenyl, benzyl, 1-phenylethyl, 2-phenylethyl, 2-phenylethenyl, phenylcyclopropyl, pyridinyl, thienyl, N-methylimidazolyl, 3,5-dimethylisoxazolyl, wherein benzyl is unsubstituted or substituted by a methyl group, and phenyl is unsubstituted or substituted by one or two substituents independently selected from the group consisting of methyl, fluoro, chloro, cyano, hydroxy, and dimethylamino; with the proviso that when Y is —S(O)$_2$— then X can not contain an —O— group. For certain of these embodiments, Y is selected from the group consisting of —N($R_8$)—C(O)—, —N($R_8$)—S(O)$_2$—, and —N($R_8$)—C(O)—N($R_{8a}$)—. For certain of these embodiments, $R_{8a}$ is hydrogen. Alternatively, for certain of these embodiments, $R_{8a}$ is methyl. For certain of these embodiments, $R_8$ is hydrogen. Alternatively, for certain of these embodiments, $R_8$ is benzyl. Alternatively, for certain of these embodiments, $R_8$ is pyridin-3-ylmethyl. Alternatively, for certain of these embodiments, Y is —S(O)$_2$—. For certain of these embodiments, X is $C_{1-6}$ alkylene.

For certain embodiments of Formula I, II, or III, including any one of the above embodiments except where $R_1$ is —X—Y—$R_4$, $R_1$ is —X—$R_5$, wherein X is straight chain or branched chain $C_{1-6}$ alkylene, and $R_5$ is

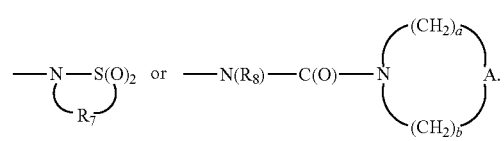

For certain of these embodiments, $R_5$ is

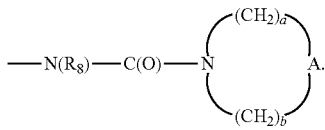

For certain of these embodiments, $R_8$ is hydrogen, methyl, or pyridin-3-ylmethyl, A is —O—, —CH$_2$—, or —N(CH$_3$)—, a is 1 or 2, and b is 2. For certain of these embodiments, $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl.

For certain embodiments of Formula I, II, or III, including any one of the above embodiments except where $R_1$ is —X—Y—R$_4$ or —X—R$_5$, $R_1$ is —C$_{1-4}$ alkylenyl-Het. For certain of these embodiments, as well as any one of the above embodiments where Het is present, Het is selected from the group consisting of tetrahydropyranyl and tetrahydrofuranyl. For certain of these embodiments, as well as any one of the above embodiments where Het is present, $R_1$ is tetrahydro-2H-pyran-4-ylmethyl.

For certain embodiments, for example, embodiments of Formula I, the present invention provides a compound selected from the group consisting of N-[4-(4-amino-2-hydroxymethyl-1H-imidazo[4,5-c]quinolin-1-yl)butyl]methanesulfonamide and N-{4-[4-amino-2-(2-hydroxyethyl)-1H-imidazo[4,5-c]quinolin-1-yl]butyl}methanesulfonamide, or a pharmaceutically acceptable salt thereof.

For certain embodiments, for example, embodiments of Formula I, the present invention provides N-{2-[4-amino-2-(hydroxymethyl)-1H-imidazo[4,5-c]quinolin-1-yl]-1,1-dimethylethyl}methanesulfonamide or a pharmaceutically acceptable salt thereof.

For certain embodiments, the present invention provides a pharmaceutical composition comprising a therapeutically effective amount of a compound or salt of Formula I, II, III, or of any one of the above embodiments and a pharmaceutically acceptable carrier.

For certain embodiments, the present invention provides a method of preferentially inducing the biosynthesis of IFN-α in an animal comprising administering an effective amount of a compound or salt of Formula I, II, III, or of any one of the above embodiments or the above pharmaceutical composition to the animal.

For certain embodiments, the present invention provides a method of treating a viral disease in an animal in need thereof comprising administering a therapeutically effective amount of a compound or salt of Formula I, II, III, or of any one of the above embodiments or the above pharmaceutical composition to the animal.

For certain embodiments, the present invention provides a method of treating a neoplastic disease in an animal in need thereof comprising administering a therapeutically effective amount of a compound or salt of Formula I, II, III, or of any one of the above embodiments or the above pharmaceutical composition to the animal.

For certain embodiments of the above methods, the compound or salt or pharmaceutical composition is administered systemically.

For certain embodiments, R is selected from the group consisting of C$_{1-10}$ alkyl, C$_{1-10}$ alkoxy, halogen, and C$_{1-10}$ haloalkyl.

For certain embodiments, $R_1$ is selected from the group consisting of —X—Y—R$_4$, —X—R$_5$, and —X-Het.

For certain embodiments, $R_1$ is —X—Y—R$_4$.

For certain embodiments, $R_1$ is —X—Y—R$_4$ wherein X is straight chain or branched chain C$_{1-6}$ alkylene which may be interrupted by one —O— group; Y is selected from the group consisting of —N(R$_8$)—C(O)—, —N(R$_8$)—S(O)$_2$—, —N(R$_8$)—C(O)—N(R$_8$)—, and —S(O)$_2$— wherein R$_8$ is selected from hydrogen and methyl; and R$_4$ is selected from the group consisting of C$_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

For certain embodiments, $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino]carbonyl}amino)propyl, and 2,2-dimethyl-3-(methylsulfonyl)propyl.

For certain embodiments, $R_1$ is —X—R$_5$.

For certain embodiments, $R_1$ is —X—R$_5$ wherein X is straight chain or branched chain C$_{1-6}$ alkylene, and R$_5$ is

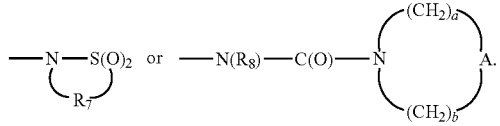

For certain embodiments, $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl.

For certain embodiments, $R_1$ is —X-Het.

For certain embodiments, $R_1$ is —C$_{1-4}$ alkylenyl-Het.

For certain embodiments, $R_1$ is tetrahydro-2H-pyran-4-ylmethyl.

For certain embodiments, R$_4$ is selected from the group consisting of hydrogen, alkyl, alkenyl, aryl, arylalkylenyl, heteroaryl, and heteroarylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo.

For certain embodiments, R$_4$ is selected from the group consisting of C$_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

For certain embodiments, R$_4$ is selected from the group consisting of C$_{1-7}$ alkyl, haloC$_{1-4}$ alkyl, hydroxyC$_{1-4}$ alkyl, phenyl, benzyl, 1-phenylethyl, 2-phenylethyl, 2-phenylethenyl, phenylcyclopropyl, pyridinyl, thienyl, N-methylimidazolyl, 3,5-dimethylisoxazolyl, wherein benzyl is unsubstituted or substituted by a methyl group, and phenyl is unsubstituted or substituted by one or two substituents independently selected from the group consisting of methyl, fluoro, chloro, cyano, hydroxy, and dimethylamino.

For certain embodiments, R$_4$ is C$_{1-7}$ alkyl.

For certain embodiments, R$_4$ is C$_{1-4}$ alkyl.

For certain embodiments, R$_4$ is phenyl which is unsubstituted or substituted by one or two substituents independently selected from the group consisting of methyl, fluoro, chloro, cyano, hydroxy, and dimethylamino.

For certain embodiments, R$_5$ is selected from the group consisting of

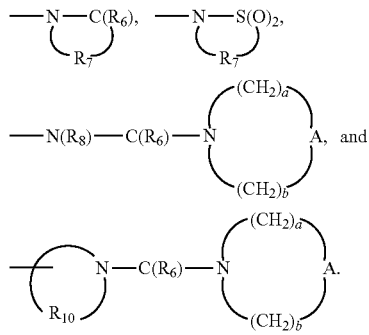

For certain embodiments, R$_5$ is

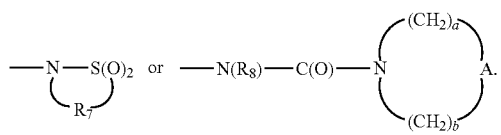

For certain embodiments, R$_5$ is

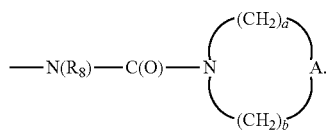

For certain embodiments, R$_6$ is selected from the group consisting of =O and =S.

For certain embodiments, R$_6$ is =O.

For certain embodiments, R$_6$ is =S.

For certain embodiments, R$_7$ is C$_{2-7}$ alkylene.

For certain embodiments, R$_7$ is C$_{2-4}$ alkylene.

For certain embodiments, R$_8$ is selected from the group consisting of hydrogen, alkyl, alkoxyalkylenyl, hydroxyalkylenyl, arylalkylenyl, and heteroarylalkylenyl.

For certain embodiments, R$_8$ is selected from the group consisting of hydrogen, C$_{1-4}$ alkyl, and C$_{1-4}$ alkoxyC$_{1-4}$ alkylenyl.

For certain embodiments, R$_8$ is arylalkylenyl.

For certain embodiments, R$_8$ is benzyl.

For certain embodiments, R$_8$ is heteroarylalkylenyl.

For certain embodiments, R$_8$ is pyridin-3-ylmethyl.

For certain embodiments, R$_8$ is hydrogen or C$_{1-4}$ alkyl.

For certain embodiments, R$_8$ is selected from hydrogen and methyl.

For certain embodiments, R$_8$ is hydrogen.

For certain embodiments, R$_{10}$ is C$_{3-8}$ alkylene.

For certain embodiments, R$_{10}$ is C$_{4-6}$ alkylene.

For certain embodiments, A is selected from the group consisting of —O—, —C(O)—, —CH$_2$—, —S(O)$_{0-2}$—, and —N(Q-R$_4$)—.

For certain embodiments, A is —O—, —CH$_2$—, or —N(Q-R$_4$)—.

For certain embodiments, A is —O—, —CH$_2$—, —S—, or —S(O)$_2$—.

For certain embodiments, A is —O— or —S(O)$_2$—.

For certain embodiments, A is —O—.

For certain embodiments, A is —CH$_2$—.

For certain embodiments, A is —N(Q-R$_4$)—.

For certain embodiments, A is —N(CH$_3$)—.

For certain embodiments, including any one of the above embodiments of Formula II, G$_1$ is selected from the group consisting of —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; α-aminoacyl is an α-aminoacyl group derived from an α-amino acid selected from the group consisting of racemic, D-, and L-amino acids; Y' is selected from the group consisting of hydrogen, C$_{1-6}$ alkyl, and benzyl; Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl; and Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments of Formula II, G$_1$ is selected from the group consisting of —C(O)—R', α-aminoacyl, and —C(O)—O—R'. For certain of these embodiments, R' contains one to ten carbon atoms. For certain of these embodiments, α-aminoacyl is an α-C$_{2-11}$ aminoacyl group derived from an α-amino acid selected from the group consisting of racemic, D-, and L-amino acids containing a total of at least 2 carbon atoms and a total of up to 11 carbon atoms, and may also include one or more heteroatoms selected from the group consisting of O, S, and N.

For certain embodiments, including any one of the above embodiments of Formula III, G$_2$ is selected from the group consisting of —X$_2$—C(O)—R', α-aminoacyl, α-aminoacyl-α-aminoacyl, —X$_2$—C(O)—O—R', and —C(O)—N(R")R'. For certain of these embodiments, X$_2$ is selected from the group consisting of a bond; —CH$_2$—O—; —CH(CH$_3$)—O—; —C(CH$_3$)$_2$—O—; and, in the case of —X$_2$—C(O)—O—R', —CH$_2$—NH—; R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; and α-aminoacyl is an α-aminoacyl group derived from an α-amino acid selected from the group consisting of racemic, D-, and L-amino acids.

For certain embodiments, including any one of the above embodiments of Formula III, $G_2$ is selected from the group consisting of —C(O)—R' and α-aminoacyl, wherein R' is $C_{1-6}$ alkyl or phenyl which is unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$.

For certain embodiments, including any one of the above embodiments of Formula III, $G_2$ is selected from the group consisting of α-amino-$C_{2-5}$ alkanoyl, $C_{2-6}$ alkanoyl, $C_{1-6}$ alkoxycarbonyl, and $C_{1-6}$ alkylcarbamoyl.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the amino acid is selected from the group consisting of racemic, D-, and L-amino acids.

For certain embodiments, the hydrogen atom of the hydroxy group of Formula II (including any one of its embodiments) is replaced by $G_2$, wherein $G_2$ is defined as in any one of the above embodiments of $G_2$.

For certain embodiments, Het is selected from the group consisting of tetrahydropyranyl and tetrahydrofuranyl.

For certain embodiments, Het is tetrahydro-2H-pyran-4-yl.

For certain embodiments, Q is selected from the group consisting of a bond, —C($R_6$)—, —$S(O)_2$, —C($R_6$)—N($R_8$)—, —$S(O)_2$—N($R_8$)—, —C($R_6$)—O—, and —C($R_6$)—S—.

For certain embodiments, Q is selected from the group consisting of a bond, —C($R_6$)—, —$S(O)_2$—, and —C($R_6$)—N($R_8$)—.

For certain embodiments, Q is selected from the group consisting of —C(O)—, —$S(O)_2$—, and —C(O)—N($R_8$)—. In certain of these embodiments, $R_8$ is hydrogen or methyl.

For certain embodiments, Q is —C(O)—.

For certain embodiments, Q is —$S(O)_2$—.

For certain embodiments, Q is —C($R_6$)—N($R_8$)—.

For certain embodiments, Q is —C(O)—N($R_8$)— wherein $R_8$ is hydrogen or methyl.

For certain embodiments, X is straight chain or branched chain alkylene optionally interrupted by one —O— group.

For certain embodiments, X is straight chain or branched chain $C_{1-6}$ alkylene which may be interrupted by one —O— group.

For certain embodiments, X is straight chain or branched chain $C_{1-8}$ alkylene.

For certain embodiments, X is straight chain or branched chain $C_{1-6}$ alkylene.

For certain embodiments, X is straight chain or branched chain $C_{1-4}$ alkylene.

For certain embodiments, X is ethylene.

For certain embodiments, X is propylene.

For certain embodiments, X is butylene.

For certain embodiments, X is —$CH_2$—C($CH_3$)$_2$—.

For certain embodiments, Y is selected from the group consisting of —$S(O)_{0-2}$— and —N($R_8$)-Q-, with the proviso that when Y is —$S(O)_{0-2}$— then X does not contain an —O— group.

For certain embodiments, Y is selected from the group consisting of —N($R_8$)—C(O)—, —N($R_8$)—$S(O)_2$—, —N($R_8$)—C(O)—N($R_8$)—, and —$S(O)_2$—, with the proviso that when Y is —$S(O)_2$— then X does not contain an —O— group. In certain of these embodiments, $R_8$ is selected from hydrogen and methyl.

For certain embodiments, Y is selected from the group consisting of —N($R_8$)—C(O)—, —N($R_8$)—$S(O)_2$—, —N($R_8$)—$S(O)_2$—N($R_{8a}$)—, —N($R_8$)—C(O)—N($R_{8a}$)—, and —$S(O)_2$—.

For certain embodiments, Y is selected from the group consisting of —N($R_8$)—C(O)—, —N($R_8$)—$S(O)_2$—, —N($R_8$)—C(O)—N($R_{8a}$)—.

For certain embodiments, Y is —$S(O)_2$—.

For certain embodiments, a and b are independently integers from 1 to 6 with the proviso that a+b is $\leq 7$.

For certain embodiments, a and b are each independently 1 to 3.

For certain embodiments, a and b are each 2.

For certain embodiments, a is 1, 2, or 3, and b is 2.

For certain embodiments, a is 1 or 2, and b is 2.

For n certain embodiments, n is 1 or 2.

For certain embodiments, n is 1.

For certain embodiments, n is 2.

For certain embodiments, m is 0 or 1.

For certain embodiments, m is 0.

For certain embodiments, m is 1.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

In some embodiments, compounds of the invention can be prepared according to Reaction Scheme I, wherein $R_1$, R, m, and n are as defined above and alkyl is methyl or ethyl.

In Reaction Scheme I an ether substituted 1H-imidazo[4,5-c]quinolin-4-amine of Formula X is cleaved to provide a hydroxyalkyl substituted 1H-imidazo[4,5-c]quinolin-4-amine of Formula I. The reaction is conveniently carried out by adding a solution of boron tribromide in a suitable solvent such as dichloromethane to a solution or suspension of a compound of Formula X in a suitable solvent such as dichloromethane at ambient or at a sub-ambient temperature, for example, at 0° C. The product or pharmaceutically acceptable salt thereof can be isolated using conventional methods.

Numerous compounds of Formula X are known; others can be prepared using known synthetic methods. See, for example, U.S. Pat. Nos. 6,069,149; 6,331,539; 6,451,810; 6,541,485; 6,756,382; 6,677,349; 6,573,273; 6,664,264; 6,664,265; 6,677,347; 6,660,735; 6,683,088; and 6,667,312 and the references cited therein.

hydrogen atom in an amino group with a group such as —C(O)—R', α-aminoacyl, α-aminoacyl-α-aminoacyl, C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; wherein R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; each α-aminoacyl is an α-aminoacyl group derived from an α-amino acid selected from the group consisting of racemic, D-, and L-amino acids; Y' is selected from the group consisting of hydrogen, $C_{1-6}$ alkyl, and benzyl; Y$_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and Y$_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl. Particularly useful compounds of Formula II are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at ambient temperature.

Alternatively, the hydroxy group on a compound of Formula I can be protected using a suitable silyl group such as tert-butyl dimethylsilyl using conventional methods. The $G_1$ group may then be installed using conventional methods followed by the removal of the hydroxy protecting group under acidic conditions to provide a compound of Formula II.

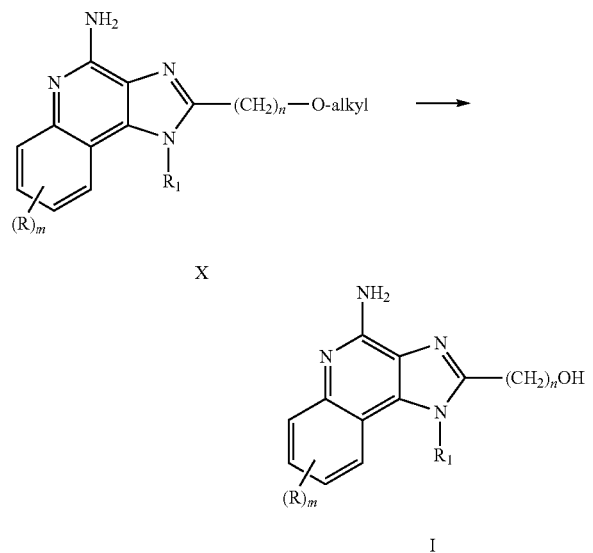

Reaction Scheme I

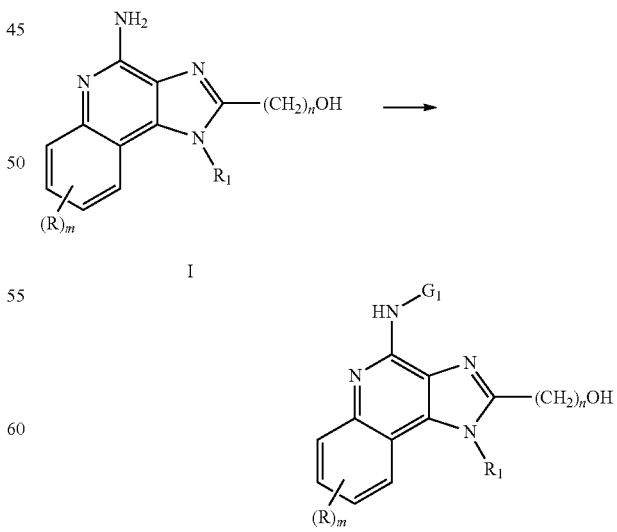

Reaction Scheme II

In some embodiments, compounds of the invention can be prepared according to Reaction Scheme II, wherein $R_1$, $G_1$, and n are as defined above. Compounds of Formula I can be prepared according to the method described above. The amino group of a compound of Formula I can be converted by conventional methods to a functional group such as an amide, carbamate, urea, amidine, or another hydrolyzable group. A compound of this type can be made by the replacement of a In some embodiments, compounds of the invention can be prepared according to Reaction Scheme III, wherein $R_1$, $G_2$, and n are as defined above. Compounds of Formula I can be prepared according to the method described above. The hydrogen atom of the alcohol group of a compound of Formula I can be replaced using conventional methods with a group such as $X_2$—C(O)—R', α-aminoacyl, α-aminoacyl-α-aminoacyl, —$X_2$—C(O)—O—R', and —C(O)—N(R")R'; wherein $X_2$ is selected from the group consisting of a bond; —$CH_2$—O—; —CH($CH_3$)—O—; —C($CH_3$)$_2$—O—; and, in the case of —$X_2$—C(O)—O—R', —$CH_2$—NH—; R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R" can also be hydrogen; and each α-aminoacyl is an α-aminoacyl group derived from an α-amino acid selected from the group consisting of racemic, D-, and L-amino acids. Particularly useful compounds of Formula III are esters made from carboxylic acids containing one to six carbon atoms, unsubstituted or substituted benzoic acid esters, or esters made from naturally occurring amino acids. For example, the reaction can be carried out by treating a compound of Formula I with a carboxylic acid or amino acid under Mitsunobu reaction conditions by adding triphenylphosphine and a carboxylic acid to a solution or suspension of a compound of Formula I in a suitable solvent such as tetrahydrofuran and then slowly adding diisopropyl azodicarboxylate. The reaction can be run at a sub-ambient temperature such as 0° C.

Reaction Scheme III

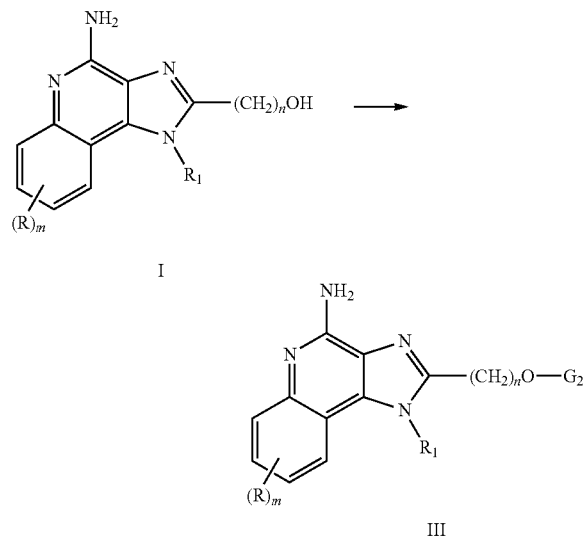

In some embodiments, compounds of the invention can also be prepared using the synthetic methods described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Cytokine induction can include preferentially inducing the biosynthesis of IFN-α. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations (e.g., intravenous formulations), syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders. The compounds or salts of the invention are especially useful as immune response modifiers due to their ability to preferentially induce interferon-α, thus providing a benefit over compounds that also induce pro-inflammatory cytokines (e.g. TNF-α) or that induce pro-inflammatory cytokines at higher levels. While interferon-α and pro-inflammatory cytokines are beneficial in treating certain conditions, interferon-α preferentially induced is believed to be better tolerated by patients, because the significantly lower levels of pro-inflammatory cytokines can result in fewer or less severe adverse side effects experienced by patients. For example, if a subject is treated for a disease (e.g., hepatitis C, metastatic cancer) with a compound that induces significant levels of pro-inflammatory cytokines, while treating the disease, the compound may also cause side effects, such as severe and/or widespread inflammation, tissue destruction, or emesis, that render the subject unable or unwilling to receive the treatment. Alternatively, if a subject is treated with a compound that preferentially induces interferon-α then the compound may treat the disease with less risk of adverse side effects from pro-inflammatory cytokines such as TNF-α. Therefore, by maintaining the ability to treat a condition and reducing adverse side effects, compounds that preferentially induce IFN-α provide an advantage over compounds that would also induce pro-inflammatory cytokines, such as TNF-α, at higher levels.

The ability of the compounds or salts of the invention to preferentially induce the biosynthesis of IFN-α may be particularly advantageous when administered systemically, since adverse side effects, including for example widespread inflammation, may be reduced or even eliminated. Compounds of the invention may be administered systemically in a number of ways, including but not limited to oral and intravenous administration.

Cytokines whose biosynthesis may be induced by compounds or salts of the invention include IFN-α, IP-10, MCP-1, and a variety of other cytokines. In some instances, cytokines such as TNF-α, IL-12 may be induced, albeit at significantly reduced levels. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, the compounds or salts may cause maturation of dendritic cells or proliferation and differentiation of B-lymphocytes.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as dendritic cells and B-cells to produce an amount of one or more cytokines such as, for example, IFN-α, IP-10, and MCP-1 that is increased (induced) over a background level of such cytokines. The precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention provides a method of treating a disease which is responsive to the induction of cytokine biosynthesis, particularly the preferential induction of IFN-α, including a method of treating a viral infection in an animal and a method of treating a neoplastic disease in an animal, comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In the examples below normal high performance flash chromatography (prep HPLC) was carried out using a COMBIFLASH system (an automated high-performance flash purification product available from Teledyne Isco, Inc., Lincoln, Nebr., USA) or a HORIZON HPFC system (an automated high-performance flash purification product available from Biotage, Inc, Charlottesville, Va., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

N-{3-[4-Amino-2-(2-hydroxyethyl)-1H-imidazo[4,5-c]quinolin-1-yl]propyl}-4-methylbenzenesulfonamide

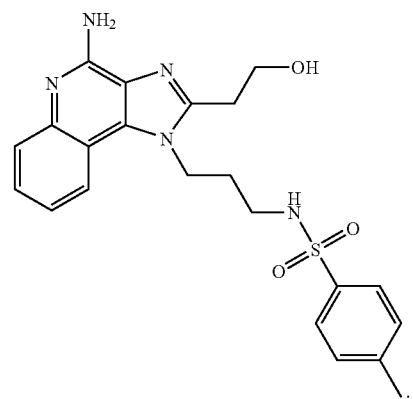

Boron tribromide (5.50 mL of 1 M in dichloromethane) was added dropwise to a chilled (0° C.) suspension of N-{3-[4-amino-2-(2-methoxyethyl)-1H-imidazo[4,5-c]quinolin-1-yl]propyl}-4-methylbenzenesulfonamide (1.0 g, 2.2 mmol; U.S. Pat. No. 6,677,349, Example 253) in dichloromethane (20 mL). The reaction mixture was stirred at 0° C. for 3 hours. The reaction mixture was quenched with methanol. Hydrochloric acid (about 10 mL of 6 N) was added and the mixture was stirred at 50° C. overnight. The mixture was diluted with water (50 mL) and ethyl acetate (100 mL) and then brought to neutral pH with solid sodium hydroxide. The layers were separated and the aqueous was extracted with ethyl acetate (×2). The combined organics were dried over magnesium sulfate, filtered, and then concentrated under reduced pressure to provide a yellow solid. This material was purified by prep HPLC (COMBIFLASH system eluting first with a gradient of 0 to 5% methanol in dichloromethane containing 1% ammonium hydroxide and then with a gradient of 5 to 10% methanol in dichloromethane containing 1% ammonium hydroxide) to provide a white solid. This material was suspended in hot acetonitrile, allowed to cool, and then the solvent was decanted. The resulting material was dried under vacuum to provide about 200 mg of N-{3-[4-amino-2-(2-hydroxyethyl)-1H-imidazo[4,5-c]quinolin-1-yl]propyl}-4-methylbenzenesulfonamide as a white solid, m p. 231-232° C. Anal. calcd for $C_{22}H_{25}N_5O_3S \cdot 0.20\ CH_4O$: % C, 59.79; % H, 5.85; % N, 15.70. Found: % C, 59.44; % H, 5.89; % N, 15.52.

Example 2

N-{3-[4-Amino-2-(2-hydroxyethyl)-1H-imidazo[4,5-c]quinolin-1-yl]propyl}isoquinoline-3-carboxamide

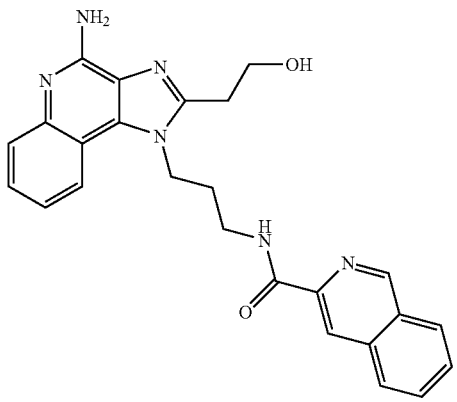

Boron tribromide (5.50 mL of 1 M in dichloromethane) was added dropwise to a chilled (0° C.) suspension of N-{3-[4-amino-2-(2-methoxyethyl)-1H-imidazo[4,5-c]quinolin-1-yl]propyl}isoquinoline-3-carboxamide (1.0 g, 2.2 mmol; U.S. Pat. No. 6,756,382, Example 192) in dichloromethane (20 mL). The reaction mixture was stirred at 0° C. for 45 minutes and then allowed to warm to ambient temperature. After 5 hours the reaction mixture was concentrated under reduced pressure and the residue was allowed to stand over the weekend. The residue was diluted with methanol (20 mL) and then heated to 50° C. Hydrochloric acid (about 10 mL of 6 N) was added and the mixture was stirred for about 2.5 hours. The mixture was made basic with aqueous sodium hydroxide and then extracted with ethyl acetate (x2). The combined extracts were dried over magnesium sulfate, filtered, and then concentrated under reduced pressure to provide a yellow solid. This material was purified by prep HPLC (COMBIFLASH system eluting first with a gradient of 0 to 5% methanol in dichloromethane containing 1% ammonium hydroxide and then with a gradient of 5 to 10% methanol in dichloromethane containing 1% ammonium hydroxide) to provide a white solid. This material was suspended in hot acetonitrile, allowed to cool, and then the solvent was decanted. The resulting material was dried under vacuum to provide about 400 mg of N-{3-[4-amino-2-(2-hydroxyethyl)-1H-imidazo[4,5-c]quinolin-1-yl]propyl}isoquinoline-3-carboxamide as a white solid, mp 245-246° C. Anal calcd for $C_{25}H_{24}N_6O_2$: % C, 67.73; % H, 5.59; % N, 18.80. Found: % C, 67.38; % H, 5.54; % N, 18.84.

Example 3

N-{4-[4-Amino-2-(2-hydroxyethyl)-1H-imidazo[4,5-c]quinolin-1-yl]butyl}methanesulfonamide

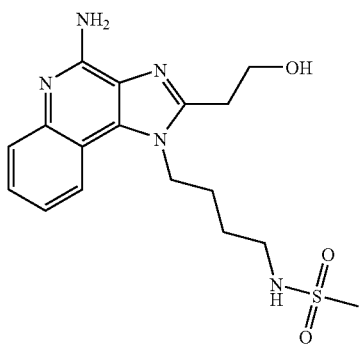

Part A

3-Methoxypropionyl chloride (15.4 g, 126 mmol) was added dropwise over a period of 20 minutes to a chilled (ice bath) solution of tert-butyl N-{4-[(3-aminoquinolin-4-yl)amino]butyl}carbamate (38 g, 115 mmol, U.S. Pat. No. 6,541,485, Example 2, Part B) in pyridine. The reaction mixture was stirred for 4 hours and then allowed to stand at ambient temperature over the weekend. Pyridine hydrochloride (3.9 g, 34 mmol) was added and the reaction mixture was heated at reflux overnight. The reaction mixture was concentrated under reduced pressure and the residue was diluted with dichloromethane (250 mL) and aqueous sodium bicarbonate (250 mL). The layers were separated. The separatory funnel was rinsed with a small amount of methanol to remove a residue coating the walls. The combined organics were concentrated under reduced pressure. The residue was purified by prep HPLC (COMBIFLASH system eluting first with a gradient of 0 to 5% methanol in dichloromethane containing 1% ammonium hydroxide and then with a gradient of 5 to 10% methanol in dichloromethane containing 1% ammonium hydroxide) to provide 18 g of tert-butyl N-{4-[2-(2-methoxyethyl)-1H-imidazo[4,5-c]quinolin-1-yl]butyl}carbamate.

Part B

3-Chloroperoxybenzoic acid (20 g of 77%) was added in a single portion to a solution of the material from Part A (18 g, 45.2 mmol) in dichloroethane (170 mL). After 2 hours concentrated ammonium hydroxide (150 mL) was added and the reaction mixture was stirred until the phases were mixed well. Para-Toluenesulfonyl chloride (10.6 g, 54 mmol) was added in a single portion along with a small amount of dichloroethane. The reaction mixture was stirred overnight at ambient temperature and then diluted with water and dichloromethane. The layers were separated and the aqueous layer was extracted with dichloromethane (x2). The combined organics were dried over magnesium sulfate, filtered, and then concentrated under reduced pressure to provide 23 g of crude tert-butyl N-{4-[4-amino-2-(2-methoxyethyl)-1H-imidazo[4,5-c]quinolin-1-yl]butyl}carbamate as a red tar.

Part C

The material from Part B was combined with a solution of hydrochloric acid in dioxane (325 mL of 4 M) and stirred at ambient temperature for 3 hours. The reaction mixture was concentrated under reduced pressure. The residue was dissolved in methanol (30 mL) and 6 M sodium hydroxide was added with stirring to about pH 9. Attempts to extract with dichloromethane and ethyl acetate were not successful. The organic and aqueous layers were concentrated under reduced pressure and combined to provide a dark orange solid. This material was purified by prep HPLC (COMBIFLASH system eluting first with a gradient of 0 to 8% methanol in dichloromethane containing 1% ammonium hydroxide and then with a gradient of 9 to 35% methanol in dichloromethane containing 1% ammonium hydroxide) to provide 10.65 g of 1-(4-aminobutyl)-2-(2-methoxyethyl)-1H-imidazo[4,5-c]quinolin-4-amine as an orange solid.

Part D

Triethylamine (10.5 mL, 75.0 mmol) was added to a mixture of a portion (4.7 g, 15 mmol) of the material from Part C in pyridine (50 mL). The reaction mixture was stirred for several minutes and then methanesulfonyl chloride (1.27 mL, 16.5 mmol) was added dropwise. The reaction mixture was stirred at ambient temperature for 2 hours and then at 50° C. for 2 hours. More methanesulfonyl chloride (0.5 eq) was added and the reaction mixture was stirred at 50° C. for 2 hours. Another portion of methanesulfonyl chloride (0.25 eq) was added and the reaction mixture was stirred at ambient temperature overnight. The reaction mixture was diluted with dichloromethane and water. The layers were separated and the aqueous layer was extracted with dichloromethane (×3). The combined organics were dried over magnesium sulfate, filtered, and then concentrated under reduced pressure to provide 5 g of crude N-{4-[4-amino-2-(2-methoxyethyl)-1H-imidazo[4,5-c]quinolin-1-yl]butyl}methanesulfonamide as a red oil.

Part E

Boron tribromide (22.4 mL of 1 M in dichloromethane) was added slowly to a chilled (ice bath) mixture of a portion of the material from Part D (3.5 g, about 8.9 mmol) and dichloromethane (50 mL). After the addition was complete the ice bath was removed and the reaction mixture was allowed to stir at ambient temperature for 3 hours. The reaction mixture was concentrated under reduced pressure. The residue was dissolved in methanol and then combined with hydrochloric acid (50 mL of 6 M). The mixture was stirred at 50° C. for 2 hours and then concentrated under reduced pressure. The residue was combined with ammonia in methanol (about 50 mL of 7 M) to neutralize the acid and then concentrated. This procedure was repeated 3 times. The crude product was purified by prep HPLC (COMBIFLASH system eluting with a gradient of 0 to 10% methanol in dichloromethane containing 1% ammonium hydroxide). The product was stirred with hot acetonitrile, allowed to stand overnight, and then isolated by filtration, washed with acetonitrile, and dried in a vacuum oven to provide 1.1 g of N-{4-[4-amino-2-(2-hydroxyethyl)-1H-imidazo[4,5-c]quinolin-1-yl]butyl}methanesulfonamide, mp 206-208° C. Anal calcd for $C_{17}H_{23}N_5O_3S$: % C, 54.09; % H, 6.14; % N, 18.55. Found: % C, 53.83; % H, 6.29; % N, 18.29.

Example 4

1-(2-Amino-2-methylpropyl)-2-hydroxymethyl-1H-imidazo[4,5-c]quinolin-4-amine

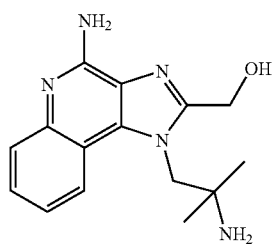

Part A

Under a nitrogen atmosphere, triethylamine (6.6 mL, 47 mmol) was added slowly to a solution of 2,4-dichloro-3-nitroquinoline (10.0 g, 41.1 mmol) in anhydrous 1-methyl-2-pyrrolidinone (40 mL). The reaction mixture was cooled to 0° C. with an ice bath. A solution of 1,2-diamino-2-methylpropane (4.1 g, 47.3 mmol) in anhydrous 1-methyl-2-pyrrolidinone (5 mL) was added dropwise over a period of 15 minutes while maintaining the temperature of the reaction mixture below 4° C. After the addition was completed the ice bath was removed and the reaction mixture was allowed to stir at ambient temperature for 4 hours. The reaction mixture was slowly poured into vigorously stirred warm water (300 mL). The resulting suspension was stirred for 1 hour and then cooled to 13° C. by adding ice. The solid was isolated by filtration and then washed with cold water until the filtrate was clear to provide 12.1 g of $N^1$-(2-chloro-3-nitroquinolin-4-yl)-2-methylpropane-1,2-diamine as a damp yellow solid.

Part B

A solution of sodium hydroxide (1.8 g of solid sodium hydroxide dissolved in 45 mL of water) was added slowly to a solution of the material from Part A (41.1 mmol) in tetrahydrofuran (96 mL). A solution of di-tert-butyl dicarbonate (10.8 g, 49.4 mmol) in tetrahydrofuran (30 mL) was added dropwise over a period of 15 minutes. The reaction solution was stirred at ambient temperature. After 6 hours 10% sodium hydroxide (2 mL) and additional di-tert-butyl dicarbonate (1.5 g) were added and the reaction solution was stirred at ambient temperature overnight. The layers were separated and the tetrahydrofuran was removed under reduced pressure to provide a mixture. The mixture was diluted with water (200 mL) and then extracted with dichloromethane (2×100 mL). The organics were combined, washed sequentially with aqueous sodium carbonate (2×150 mL) and brine (100 mL), dried over sodium sulfate and magnesium sulfate, filtered, and then concentrated under reduced pressure. The residue was triturated with heptane (75 mL) for 15 minutes at 65° C. and then filtered while hot. The isolated solids were washed with heptane (20 mL) to provide 13.2 g of tert-butyl N-{2-[(2-chloro-3-nitroquinolin-4-yl)amino]-1,1-dimethylethyl}carbamate as a yellow powdery solid.

Part C

A Parr vessel was charged with 5% Pt/C (0.5 g) and acetonitrile (10 mL). A solution of the material from Part B in acetonitrile (450 mL) was added. The vessel was placed on a Parr shaker under hydrogen pressure (40 psi, $2.8 \times 10^5$ Pa) for 5 hours. The reaction mixture was filtered through a layer of CELITE filter aid to remove the catalyst. The filtrate was carried on to the next step.

Part D

The solution of tert-butyl N-{2-[(3-amino-2-chloroquinolin-4-yl)amino]-1,1-dimethylethyl}carbamate in acetonitrile from Part C was cooled to 5° C. using an ice bath.

A solution of acetoxyacetyl chloride (4.8 g, 35.1 mmol) in acetonitrile (20 mL) was added dropwise at a rate such that the temperature of the reaction mixture was maintained at 5° C. After the addition was complete the ice bath was removed and the reaction mixture was allowed to stir at ambient temperature for 5 hours. The reaction mixture was concentrated under reduced pressure to provide 16.7 g of N-{2-[(3-acetoxyacetylamino-2-chloroquinolin-4-yl)amino]-1,1-dimethylethyl}carbamate hydrochloride as a yellow powder.

Part E

A mixture of the material from Part D (15.7 g) and ammonia in methanol (235 mL of 7 N) was divided into equal portions and placed in pressure vessels. The vessels were sealed, heated at 160° C. for 20 hrs, and then allowed to cool to ambient temperature overnight. The reaction mixtures were filtered. The isolated solids were washed with water and dried in a vacuum oven at 60° C. overnight to provide 6.0 g of a tan powder. A portion (1 g) was treated with activated charcoal and recrystallized from ethanol (75 mL) to provide 0.5 g of 1-(2-amino-2-methylpropyl)-2-hydroxymethyl-1H-imidazo[4,5-c]quinolin-4-amine as a white granular solid, mp 248-250° C. Anal calcd for $C_{15}H_{19}N_5O$: % C, 63.14; % H, 6.71; % N, 24.54. Found: % C, 63.13; % H, 6.81; % N, 24.64.

Example 5

N-[2-(4-Amino-2-hydroxymethyl-1H-imidazo[4,5-c]quinolin-1-yl)-1,1-dimethylethyl]cyclohexanecarboxamide

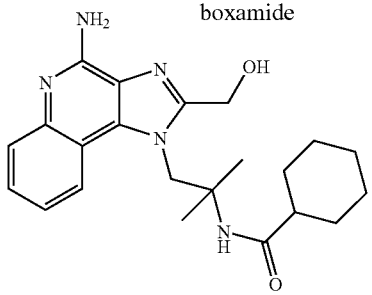

A solution of 1-(2-amino-2-methylpropyl)-2-hydroxymethyl-1H-imidazo[4,5-c]quinolin-4-amine (2.0 g, 7.0 mmol) in 1-methyl-2-pyrrolidinone (30 mL) was cooled to −20° C. Triethylamine (1.1 mL, 7.7 mmol) was added in a single portion. A chilled (−5° C.) solution of cyclohexanecarbonyl chloride (1.03 g, 7.0 mmol) in 1-methyl-2-pyrrolidinone (2 mL) was added dropwise over a period of 20 minutes while maintaining the reaction mixture at −20° C. The reaction mixture was stirred at ambient temperature overnight. Additional cyclohexanecarbonyl chloride (0.1 g) was added and the reaction mixture stirred for 2 hours. The reaction mixture was poured into water with vigorous stirring. The resulting precipitate was isolated by filtration to provide 1.7 g of an ivory powder. Analysis by high performance liquid chromatography and NMR indicated that the powder was a mixture of the desired product and an ester formed from the reaction of the hydroxy group of the desired product with cyclohexanecarbonyl chloride.

The powder was dissolved in ethanol (25 mL), combined with a solution of sodium hydroxide (0.21 g) in water (25 mL), and then heated at 50° C. for 3 hours. The ethanol was removed under reduced pressure and the solids were isolated by filtration to provide 1.2 g of a light tan powder. The powder was dissolved in a mixture of acetonitrile (100 mL), water (2 mL) and ethanol (25 mL). The solution was allowed to stand overnight and was then concentrated to a volume of 5 mL to provide a white paste. The paste was triturated with warm (70° C.) acetonitrile (50 mL), heated to reflux, and then allowed to cool to ambient temperature. The resulting solid was isolated by filtration to provide 1.05 g of N-[2-(4-amino-2-hydroxymethyl-1H-imidazo[4,5-c]quinolin-1-yl)-1,1-dimethylethyl]cyclohexanecarboxamide as a light yellow powder, mp 248-250° C. Anal calcd for $C_{22}H_{29}N_5O_2$: % C, 66.81; % H, 7.39; % N, 17.71. Found: % C, 66.56; % H, 7.60; % N, 17.82.

Example 6

N-{2-[4-Amino-2-(2-hydroxyethyl)-1H-imidazo[4,5-c]quinolin-1-yl]-1,1-dimethylethyl}methanesulfonamide

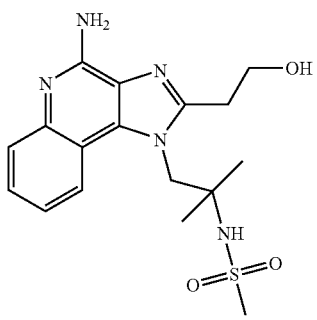

Part A

Triethylamine (39.3 mL, 0.282 mol) was added to a chilled (ice bath) solution of $N^1$-(2-chloro-3-nitroquinolin-4-yl)-2-methylpropane-1,2-diamine (41.42 g, 0.141 mol) in dichloromethane (about 500 mL). Under a nitrogen atmosphere a solution of methanesulfonic anhydride in (29.47 g, 0.169 mol) in dichloromethane (100 mL) was added via a cannula to the reaction mixture over a period of 45 minutes. After the addition was complete the ice bath was removed and the reaction mixture was allowed to stir at ambient temperature overnight. The reaction mixture was washed sequentially with saturated aqueous sodium bicarbonate (×2) and brine, dried over a mixture of sodium sulfate and magnesium sulfate, filtered, and then concentrated under reduced pressure to provide 46.22 g of an orange solid. This material was recrystallized from toluene (about 1 L), isolated by filtration, rinsed with cold toluene, and dried under high vacuum at 60° C. to provide 33.09 g of N-{2-[(2-chloro-3-nitroquinolin-4-yl)amino]-1,1-dimethylethyl}methanesulfonamide.

Part B

A hydrogenation vessel was charged with 5% Pt/C (4.14 g) and a solution of N-{2-[(2-chloro-3-nitroquinolin-4-yl)amino]-1,1-dimethylethyl}methanesulfonamide (54.59 g, 0.147 mol) in acetonitrile (1800 mL). The vessel was placed under hydrogen pressure (48 psi, $3.3 \times 10^5$ Pa) overnight. An additional portion (4.25 g) of catalyst was added and the vessel was placed under hydrogen pressure (48 psi, $3.3 \times 10^5$ Pa) for 4 hours. The reaction mixture was filtered through a layer of CELITE filter aid and the filter cake was rinsed with fresh acetonitrile until the washes were clear.

Part C

Under a nitrogen atmosphere, 3-methoxypropionyl chloride (17.6 mL, 0.162 mol) was added dropwise to the solution of N-{2-[(3-amino-2-chloroquinolin-4-yl)amino]-1,1-dimethylethyl}methanesulfonamide (0.147 mol) in acetonitrile (2.2 L) from Part B. The reaction mixture was allowed to stir at ambient temperature over the weekend. The resulting precipitate was isolated by filtration, rinsed with a small amount of acetonitrile, and then dried under high vacuum at 60° C. to provide 55.84 g of N-{2-chloro-4-[2-(methanesulfonylamino)-2-methylpropyl]quinolin-3-yl}-3-methoxypropionamide.

Part D

A Parr bomb was charged with 25.0 g of N-{2-chloro-4-[2-(methanesulfonylamino)-2-methylpropyl]aminoquinolin-3-yl}-3-methoxypropionamide and ammonia in methanol (300 mL of 7 N). A second vessel was charged with 30.21 g of N-{2-chloro-4-[2-(methanesulfonylamino)-2-methylpropyl]quinolin-3-yl}-3-methoxypropionamide and ammonia in methanol (400 mL of 7 N). Both vessels were sealed and then heated at 170° C. for 14 hours. The reaction mixtures were combined and the solvent was removed under reduced pressure. The residue was partitioned between dichloromethane and saturated aqueous sodium bicarbonate. The organic layer was washed sequentially with saturated aqueous sodium bicarbonate and brine, dried over sodium sulfate, filtered, and then concentrated under reduced pressure to provide 38.16 g of N-{2-[4-amino-2-(2-methoxyethyl)-1H-imidazo[4,5-c]quinolin-1-yl]-1,1-dimethylethyl}methanesulfonamide as an off white foam.

Part E

Under a nitrogen atmosphere, boron tribromide (3.5 mL of 1 M in dichloromethane) was added dropwise to a chilled (0° C.) solution of N-{2-[4-amino-2-(2-methoxyethyl)-1H-imidazo[4,5-c]quinolin-1-yl]-1,1-dimethylethyl}methanesulfonamide (0.55 g, 1.40 mmol) in dichloromethane (20 mL). The reaction was allowed to warm to ambient temperature overnight. The reaction was quenched with methanol (10 mL) and the solvent was removed under reduced pressure. The residue was dissolved in hydrochloric acid (6 N), stirred at 50° C. for about 2.5 hours, and then allowed to cool to ambient temperature. The reaction mixture was adjusted to pH 11 with ammonium hydroxide and then extracted with dichloromethane (×10). The combined organics were washed with brine, dried over sodium sulfate, filtered, and then concentrated under reduced pressure to provide 0.47 g of a white solid. This material was purified by prep HPLC (HORIZON HPFC system, eluting with a gradient of 30-50% CMA in chloroform for 15 column volumes followed by 50% CMA in chloroform for 5 column volumes) and then dried under high vacuum to provide 250 mg of N-{2-[4-amino-2-(2-hydroxyethyl)-1H-imidazo[4,5-c]quinolin-1-yl]-1,1-dimethylethyl}methanesulfonamide as white solid, m.p. 209-212° C. $^1$H NMR (500 MHz, DMSO-$d_6$) δ 8.30 (d, J=8.2 Hz, 1H), 7.60 (d, J=8.2 Hz, 1H), 7.39 (m, 1H), 7.27 (s, 1H), 7.21 (m, 1H), 6.49 (s, 2H), 4.84 (t, J=5.4 Hz, 2H), 4.82 (br s, 1H), 3.88 (m, 2H), 3.18 (br s, 2H), 3.00 (s, 3H), 1.27 (br s, 6H); $^{13}$C NMR (125 MHz, DMSO-$d_6$) δ 153.6, 152.0, 145.4, 133.5, 126.9, 126.8, 126.5, 121.3, 120.8, 115.6, 60.5, 57.9, 54.1, 44.8, 31.4, 25.8; MS (ESI) m/z 378 (M+H)$^+$; Anal. calcd for $C_{17}H_{23}N_5O_3S$: % C, 54.09; % H, 6.14; % N, 18.55. Found: % C, 53.76; % H, 6.02; % N, 18.32.

Example 7

N-[2-(4-Amino-2-hydroxymethyl-1H-imidazo[4,5-c]quinolin-1-yl)-1,1-dimethylethyl]methanesulfonamide

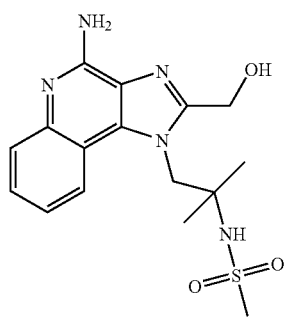

Part A

A pressure vessel was charged with a solution of N-{2-[(2-chloro-3-nitroquinolin-4-yl)amino]-1,1-dimethylethyl}methanesulfonamide (5 g, 13 mmol) in acetonitrile (150 mL). Catalyst was added (0.5 g of 5% Pt/C) and the vessel was placed under hydrogen pressure (50 psi, 3.4× 10$^5$ Pa) for 2 hours. The reaction mixture was filtered through a layer of CELITE filter aid.

Part B

The solution of N-{2-[(3-amino-2-chloroquinolin-4-yl)amino]-1,1-dimethylethyl}methanesulfonamide in acetonitrile from Part A was chilled in an ice bath. Acetoxyacetyl chloride (1.5 mL, 14 mmol) was added over a period of 5 minutes. The reaction mixture was allowed to stir for 3 hours. A precipitate was isolated by filtration and rinsed with acetonitrile to provide crude N-{2-chloro-4-[2-(methanesulfonylamino)-2-methylpropyl]quinolin-3-yl}acetoxyacetamide hydrochloride.

Part C

A solution of sodium hydroxide (0.8 g) in water (15 mL) was added to a suspension of the material from Part B in ethanol (60 mL) until all of the solid dissolved. The reaction mixture was heated at 60° C. overnight and then concentrated under reduced pressure. The residue was dissolved in water (50 mL), sodium chloride (10 g) was added, and the mixture was extracted with chloroform (3×300 mL). The extracts were concentrated under reduced pressure to provide about 4 g of crude N-[2-(4-chloro-2-hydroxymethyl-1H-imidazo[4,5-c]quinolin-1-yl)-1,1-dimethylethyl]methanesulfonamide.

Part D

The material from Part C was combined with a solution of ammonia in methanol (50 mL of 7 N) and heated at 150° C. for 10 hours. The reaction mixture was allowed to cool to ambient temperature. A precipitate was isolated by filtration, rinsed with methanol (20 mL), slurried with water (50 mL), isolated by filtration, washed with water (20 mL), and dried to provide 2.7 g of a brown crystalline solid. This material was combined with methanol (50 mL), heated at 50° C. overnight, and then isolated by filtration to provide 2.3 g of N-[2-(4-amino-2-hydroxymethyl-1H-imidazo[4,5-c]quinolin-1-yl)-1,1-dimethylethyl]methanesulfonamide, mp 262-265° C. Anal. calcd for $C_{16}H_{21}N_5O_3S$: % C, 52.88; % H, 5.82; % N, 19.27. Found: % C, 52.64; % H, 5.95; % N, 19.50.

Examples 8-72

Part A

A reagent (1.1 eq) from Table 1 below was added to a test tube containing a solution of 1-(4-aminobutyl)-2-(2-methoxyethyl)-1H-imidazo[4,5-c]quinolin-4-amine (73 mg) in N,N-dimethylacetamide (1 mL) containing N,N-diisopropylethylamine (2 eq). The test tube was placed on a shaker overnight. The solvent was removed by vacuum centrifugation. The reaction mixtures were separated by solid-supported liquid-liquid extraction according to the following procedure. Each sample was dissolved in chloroform (1 mL) then loaded onto diatomaceous earth that had been equilibrated with de-ionized water (600 μL) for about 20 minutes. After 10 minutes chloroform (500 μL) was added to elute the product from the diatomaceous earth into a well of a collection plate. After an additional 10 minutes the process was repeated with additional chloroform (500 μL). The solvent was then removed by vacuum centrifugation.

Part B

The residue (in a test tube) was combined with dichloromethane (1 mL) and the mixture was sonicated to dissolve the solids. The solution was cooled (0° C.) and then combined with boron tribromide (400 μL of 1 M in heptane). The mixture was shaken for 5 minutes, placed in an ice bath for 30 minutes, and then shaken overnight. The solvents were removed by vacuum centrifugation. The residue was diluted with methanol (1 mL) and hydrochloric acid (500 μL of 6 N). The mixture was shaken for 30 minutes and then the solvents were removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. Table 1 below shows the reagent used for each example, the structure of the resulting compound, and the observed accurate mass for the isolated trifluoroacetate salt.

TABLE 1

| Example | Reagent | R | Measured Mass (M + H) |
|---------|---------|---|------------------------|
| 8 | None | H | 300.1840 |
| 9 | Cyclopropanecarbonyl chloride | | 368.2063 |
| 10 | Isobutyryl chloride | | 370.2224 |
| 11 | Pivaloyl chloride | | 384.2390 |
| 12 | Benzoyl chloride | | 404.2103 |
| 13 | Phenyl chloroformate | | 420.2056 |
| 14 | 3-Cyanobenzoyl chloride | | 429.2031 |

TABLE 1-continued
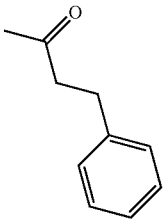
| Example | Reagent | R | Measured Mass (M + H) |
|---|---|---|---|
| 15 | Hydrocinnamoyl chloride | 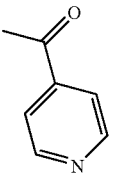 | 432.2377 |
| 16 | Isonicotinoyl chloride hydrochloride | 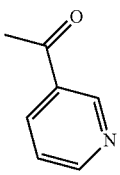 | 405.2071 |
| 17 | Nicotinoyl chloride hydrochloride | 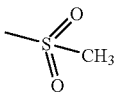 | 405.2058 |
| 18 | Methanesulfonyl chloride | 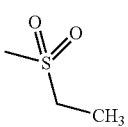 | 378.1592 |
| 19 | Ethanesulfonyl chloride | 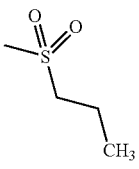 | 392.1729 |
| 20 | 1-Propanesulfonyl chloride | 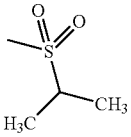 | 406.1899 |
| 21 | Isopropylsulfonyl chloride |  | 406.1888 |

TABLE 1-continued
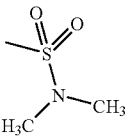
| Example | Reagent | R | Measured Mass (M + H) |
|---|---|---|---|
| 22 | Dimethylsulfamoyl chloride | 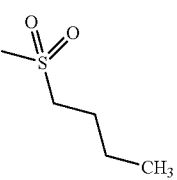 | 407.1853 |
| 23 | 1-Butanesulfonyl chloride | 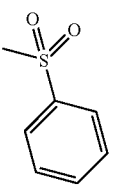 | 420.2050 |
| 24 | Benzenesulfonyl chloride | 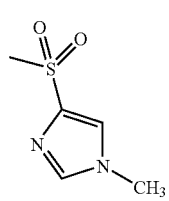 | 440.1741 |
| 25 | 1-Methylimidazole-4-sulfonyl chloride | 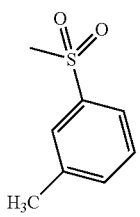 | 444.1806 |
| 26 | 3-Methylbenzenesulfonyl chloride | 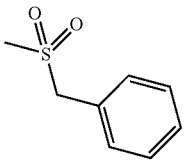 | 454.1895 |
| 27 | alpha-Toluenesulfonyl chloride | | 454.1923 |

TABLE 1-continued
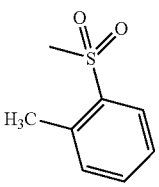
| Example | Reagent | R | Measured Mass (M + H) |
|---|---|---|---|
| 28 | o-Toluenesulfonyl chloride | 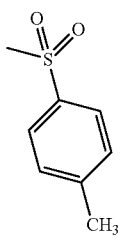 | 454.1944 |
| 29 | p-Toluenesulfonyl chloride | 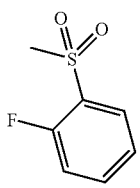 | 454.1907 |
| 30 | 2-Fluorobenzenesulfonyl chloride | 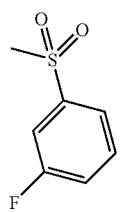 | 458.1664 |
| 31 | 3-Fluorobenzenesulfonyl chloride | 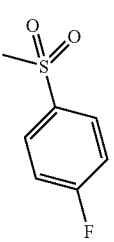 | 458.1652 |
| 32 | 4-Fluorobenzenesulfonyl chloride | | 458.1639 |

TABLE 1-continued

| Example | Reagent | R | Measured Mass (M + H) |
|---|---|---|---|
| 33 | 3-Cyanobenzenesulfonyl chloride | 3-cyanophenylsulfonyl | 465.1678 |
| 34 | 4-Cyanobenzenesulfonyl chloride | 4-cyanophenylsulfonyl | 465.1668 |
| 35 | beta-Styrene sulfonyl chloride | styrenylsulfonyl | 466.1895 |
| 36 | 2,5-Dimethylbenzenesulfonyl chloride | 2,5-dimethylphenylsulfonyl | 468.2063 |
| 37 | 3,5-Dimethylbenzenesulfonyl chloride | 3,5-dimethylphenylsulfonyl | 468.2046 |

TABLE 1-continued
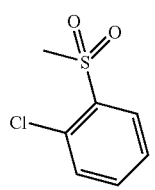
| Example | Reagent | R | Measured Mass (M + H) |
|---|---|---|---|
| 38 | 2-Chlorobenzenesulfonyl chloride | 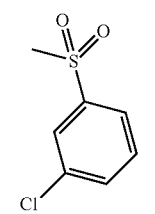 | 474.1351 |
| 39 | 3-Chlorobenzenesulfonyl chloride | 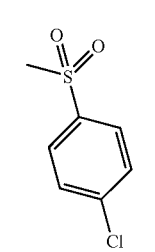 | 474.1385 |
| 40 | 4-Chlorobenzenesulfonyl chloride | 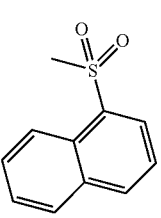 | 474.1390 |
| 41 | 1-Naphthalenesulfonyl chloride | 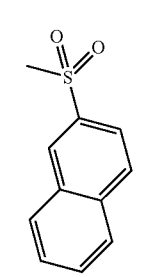 | 490.1891 |
| 42 | 2-Naphthalenesulfonyl chloride | | 490.1885 |

TABLE 1-continued
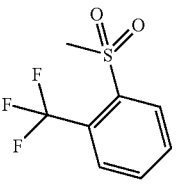
| Example | Reagent | R | Measured Mass (M + H) |
|---|---|---|---|
| 43 | 2-(Trifluoromethyl)benzenesulfonyl chloride | 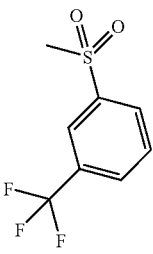 | 508.1592 |
| 44 | 3-(Trifluoromethyl)benzenesulfonyl chloride | 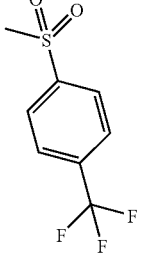 | 508.1612 |
| 45 | 4-(Trifluoromethyl)benzenesulfonyl chloride | 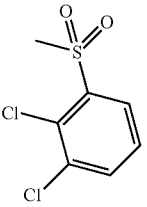 | 508.1640 |
| 46 | 2,3-Dichlorobenzenesulfonyl chloride | 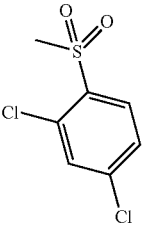 | 508.0967 |
| 47 | 2,4-Dichlorobenzenesulfonyl chloride | | 508.0979 |

TABLE 1-continued

[Structure: 4-amino-1H-imidazo[4,5-c]quinoline with 2-(2-hydroxyethyl) substituent and 1-(4-(NHR)butyl) substituent]

| Example | Reagent | R | Measured Mass (M + H) |
|---------|---------|---|------------------------|
| 48 | 2,5-Dichlorobenzenesulfonyl chloride | 2,5-dichlorophenylsulfonyl | 508.0987 |
| 49 | 2,6-Dichlorobenzenesulfonyl chloride | 2,6-dichlorophenylsulfonyl | 508.0968 |
| 50 | 3,4-Dichlorobenzenesulfonyl chloride | 3,4-dichlorophenylsulfonyl | 508.0961 |
| 51 | 3,5-Dichlorobenzenesulfonyl chloride | 3,5-dichlorophenylsulfonyl | 508.0985 |
| 52 | Methyl isocyanate | C(=O)NHCH$_3$ | 357.2073 |
| 53 | Ethyl isocyanate | C(=O)NHCH$_2$CH$_3$ | 371.2203 |

TABLE 1-continued
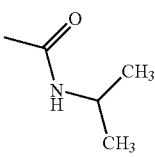
| Example | Reagent | R | Measured Mass (M + H) |
|---|---|---|---|
| 54 | Isopropyl isocyanate | 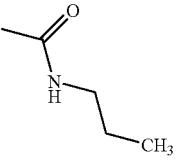 | 385.2347 |
| 55 | n-Propyl isocyanate | 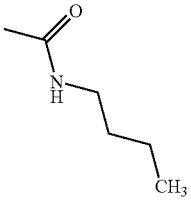 | 385.2349 |
| 56 | n-Butyl isocyanate | 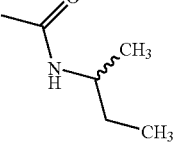 | 399.2494 |
| 57 | sec-Butyl isocyanate | 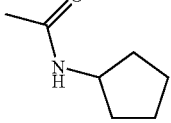 | 399.2517 |
| 58 | Cyclopentyl isocyanate | 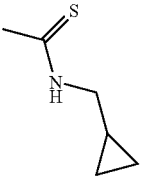 | 411.2516 |
| 59 | Cyclopropylmethyl isothiocyanate | 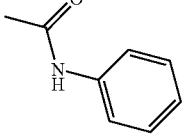 | 413.2133 |
| 60 | Phenyl isocyanate | | 419.2226 |

TABLE 1-continued
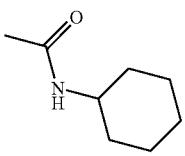
| Example | Reagent | R | Measured Mass (M + H) |
|---|---|---|---|
| 61 | Cyclohexyl isocyanate | 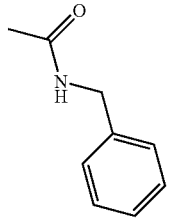 | 425.2701 |
| 62 | Benzyl isocyanate | 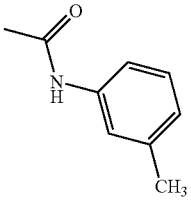 | 433.2374 |
| 63 | m-Tolyl isocyanate | 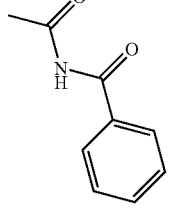 | 433.2344 |
| 64 | Benzoyl isocyanate | 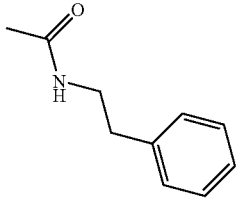 | 447.2126 |
| 65 | 2-Phenyl ethylisocyanate | | 447.2512 |
| 66 | 4-Chlorophenyl isocyanate | 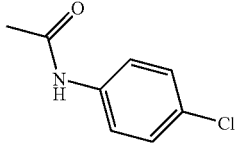 | 453.1797 |

TABLE 1-continued

[Structure: 4-amino-2-(2-hydroxyethyl)-1H-imidazo[4,5-c]quinoline with 1-(4-aminobutyl) substituent bearing NH-R group]

| Example | Reagent | R | Measured Mass (M + H) |
|---|---|---|---|
| 67 | trans-2-Phenylcyclopropyl isocyanate | -C(O)NH-(trans-2-phenylcyclopropyl) | 459.2518 |
| 68 | N,N-Dimethylcarbamoyl chloride | -C(O)N(CH₃)₂ | 371.2185 |
| 69 | 1-Pyrrolidinecarbonyl chloride | -C(O)-(1-pyrrolidinyl) | 397.2382 |
| 70 | 1-Piperidinecarbonyl chloride | -C(O)-(1-piperidinyl) | 411.2526 |
| 71 | 4-Morpholinylcarbonyl chloride | -C(O)-(4-morpholinyl) | 413.2330 |
| 72 | N-Methyl-N-phenylcarbamoyl chloride | -C(O)N(CH₃)(phenyl) | 433.2364 |

Examples 73-110

Part A

Tert-Butyl 3-[4-amino-2-(2-methoxyethyl)-1H-imidazo[4,5-c]quinolin-1-yl]propylcarbamate (5 g, U.S. Pat. No. 6,573,273, example 148) and hydrochloric acid in dioxane (100 mL of 4 M) were combined and stirred for 4 hours at ambient temperature. The reaction mixture was concentrated under reduced pressure. The residue was dissolved in methanol (30 mL). The pH was adjusted to pH 8 with 6 M sodium hydroxide. The solution was diluted with dichloromethane, ethyl acetate, triethylamine, and brine. The organic layer was concentrated under reduced pressure to provide an orange solid. This material was purified by prep HPLC (COMBI-FLASH system eluting first with a gradient of 0 to 10% methanol in dichloromethane containing 1% ammonium hydroxide and then with a gradient of 9 to 30% methanol in dichloromethane containing 1% ammonium hydroxide) to provide 1.58 g of 1-(3-aminopropyl)-2-(2-methoxyethyl)-1H-imidazo[4,5-c]quinolin-4-amine as a yellow solid.

Part B

A reagent (1.1 eq) from Table 2 below was added to a test tube containing a solution of 1-(3-aminopropyl)-2-(2-methoxyethyl)-1H-imidazo[4,5-c]quinolin-4-amine (30 mg) in chloroform (1 mL) containing N,N-diisopropylethylamine (1.5 eq). The test tube was placed on a shaker overnight. The reaction mixtures were separated by solid-supported liquid-liquid extraction according to the following procedure. Each reaction mixture was loaded onto diatomaceous earth that had been equilibrated with de-ionized water (600 μL) for about 20 minutes. After 10 minutes chloroform (500 μL) was added to elute the product from the diatomaceous earth into a well of a collection plate. After an additional 10 minutes the process was repeated with additional chloroform (500 μL). The solvent was then removed by vacuum centrifugation.

Part C

The ether was cleaved and the resulting product was purified using the method of Part B in Examples 8-72. Table 2 below shows the reagent used for each example, the structure of the resulting compound, and the observed accurate mass for the isolated trifluoroacetate salt.

TABLE 2

| Example | Reagent | R | Measured Mass (M + H) |
|---|---|---|---|
| 73 | None | 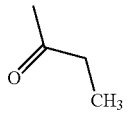 | 286.1689 |
| 74 | Propionyl chloride | 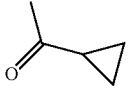 | 342.1956 |
| 75 | Cyclopropanecarbonyl chloride | 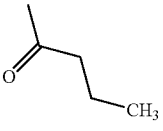 | 354.1946 |
| 76 | Butyryl chloride | 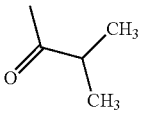 | 356.2122 |
| 77 | Isobutyryl chloride | 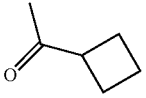 | 356.2119 |
| 78 | Cyclobutanecarbonyl chloride | 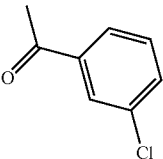 | 368.2120 |
| 79 | 3-Chlorobenzoyl chloride | | 424.1570 |

TABLE 2-continued

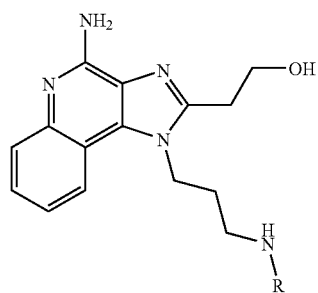

| Example | Reagent | R | Measured Mass (M + H) |
|---|---|---|---|
| 80 | 4-Chlorobenzoyl chloride | 4-chlorobenzoyl group | 424.1583 |
| 81 | Nicotinoyl chloride hydrochloride | nicotinoyl group | 391.1913 |
| 82 | trans-2-Phenyl-1-cyclopropanecarbonyl chloride | trans-2-phenylcyclopropanecarbonyl group | 430.2257 |
| 83 | Methanesulfonyl chloride | methanesulfonyl group | 364.1479 |
| 84 | Ethanesulfonyl chloride | ethanesulfonyl group | 378.1639 |
| 85 | 1-Propanesulfonyl chloride | 1-propanesulfonyl group | 392.1783 |
| 86 | Isopropylsulfonyl chloride | isopropylsulfonyl group | 392.1788 |
| 87 | Dimethylsulfamoyl chloride | dimethylsulfamoyl group | 393.1715 |
| 88 | 1-Butanesulfonyl chloride | 1-butanesulfonyl group | 406.1946 |

TABLE 2-continued
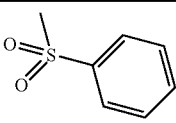
| Example | Reagent | R | Measured Mass (M + H) |
|---|---|---|---|
| 89 | Benzenesulfonyl chloride | 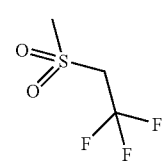 | 426.1633 |
| 90 | 2,2,2-Trifluoroethanesulfonyl chloride | 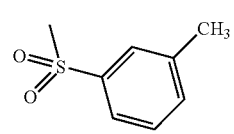 | 432.1355 |
| 91 | 3-Methylbenzenesulfonyl chloride | 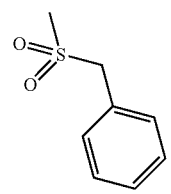 | 440.1774 |
| 92 | alpha-Toluenesulfonyl chloride | 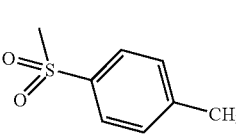 | 440.1762 |
| 93 | p-Toluenesulfonyl chloride | 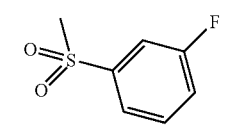 | 440.1790 |
| 94 | 3-Fluorobenzenesulfonyl chloride | 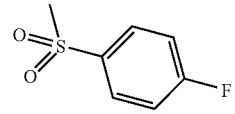 | 444.1523 |
| 95 | 4-Fluorobenzenesulfonyl chloride | 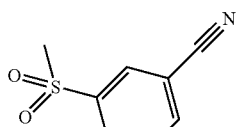 | 444.1545 |
| 96 | 3-Cyanobenzenesulfonyl chloride | 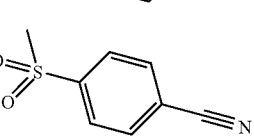 | 451.1554 |
| 97 | 4-Cyanobenzenesulfonyl chloride | | 451.1582 |

TABLE 2-continued

| Example | Reagent | R | Measured Mass (M + H) |
|---------|---------|---|----------------------|
| 98 | Ethyl isocyanate | –C(O)NH–CH₂CH₃ | 357.2050 |
| 99 | Isopropyl isocyanate | –C(O)NH–CH(CH₃)₂ | 371.2234 |
| 100 | n-Butyl isocyanate | –C(O)NH–(CH₂)₃CH₃ | 385.2364 |
| 101 | Cyclopentyl isocyanate | –C(O)NH–cyclopentyl | 397.2359 |
| 102 | Cyclopropylmethyl isothiocyanate | –C(S)NH–CH₂-cyclopropyl | 399.1979 |
| 103 | Phenyl isocyanate | –C(O)NH–phenyl | 405.2040 |
| 104 | Cyclohexyl isocyanate | –C(O)NH–cyclohexyl | 411.2526 |

TABLE 2-continued

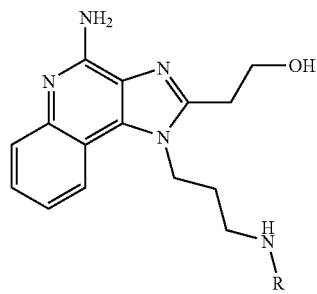

| Example | Reagent | R | Measured Mass (M + H) |
|---|---|---|---|
| 105 | Benzyl isocyanate | | 419.2239 |
| 106 | trans-2-Phenylcyclopropyl isocyanate | | 445.2388 |
| 107 | 1-Piperidinecarbonyl chloride | | 397.2384 |
| 108 | 4-Morpholinylcarbonyl chloride | | 399.2173 |
| 109 | 4-Methyl-1-piperazinecarbonyl chloride | | 412.2485 |
| 110 | N-Methyl-N-phenylcarbamoyl chloride | | 419.2229 |

Examples 111-140

Boron tribromide (400 μL of 1 M in heptane) was added to a tube containing a chilled (0° C.) solution of a compound of Formula Xa (about 25 mg) in dichloromethane (1 mL). The tube was vortexed, maintained at 0° C. for 0.5 hour, and then shaken overnight at ambient temperature. The reaction mixture was diluted with methanol (1 mL) and hydrochloric acid (250 μL of 6 N), vortexed, and then the solvents were removed by vacuum centrifugation. The compounds were purified by prep HPLC as described in Examples 8-72. Table 3 shows the structure of the starting material, a reference for the starting material, the structure of the resulting compound, and the observed accurate mass for the isolated trifluoroacetate salt.

TABLE 3
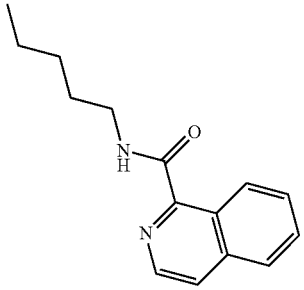
| Example | Reference Formula III | R₁ | Measured Mass (M + H) |
|---|---|---|---|
| 111 | U.S. Pat. No. 6,756,382 Example 57 | 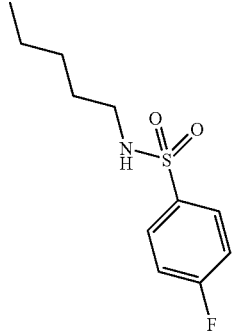 | 455.2222 |
| 112 | U.S. Pat. No. 6,331,539 Example 121 | 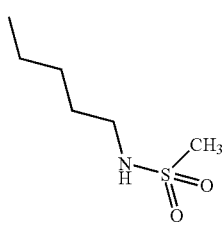 | 458.1657 |
| 113 | U.S. Pat. No. 6,331,539 Example 111 | 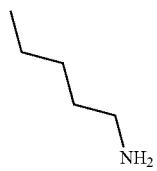 | 378.1599 |
| 114 | Example 3 Part C | | 300.1853 |

TABLE 3-continued
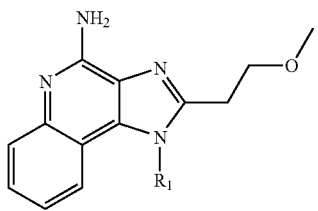
| Example | Reference Formula III | R₁ | Measured Mass (M + H) |
|---|---|---|---|
| 115 | U.S. Pat. No. 6,541,485 Example 121 | 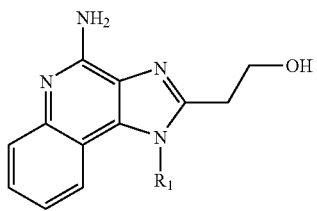 | 413.2301 |
| 116 | U.S. Pat. No. 6,756,382 Example 182 | | 455.2198 |
| 117 | U.S. Pat. No. 6,756,382 Example 183 | 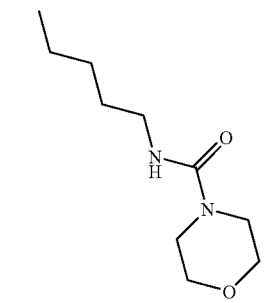 | 456.2161 |

TABLE 3-continued
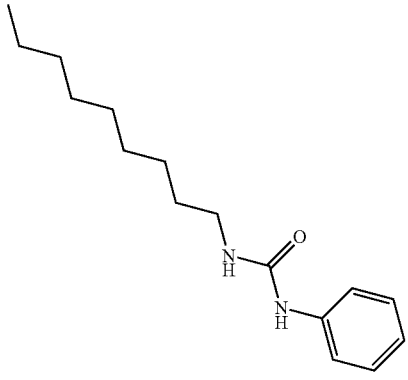
| Example | Reference Formula III | $R_1$ | Measured Mass (M + H) |
|---|---|---|---|
| 118 | U.S. Pat. No. 6,573,273 Example 145 | 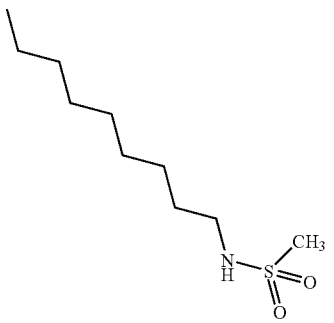 | 475.2829 |
| 119 | U.S. Pat. No. 6,677,349 Example 243 | 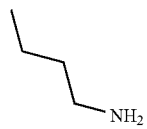 | 434.2253 |
| 120 | Example 73 Part A | 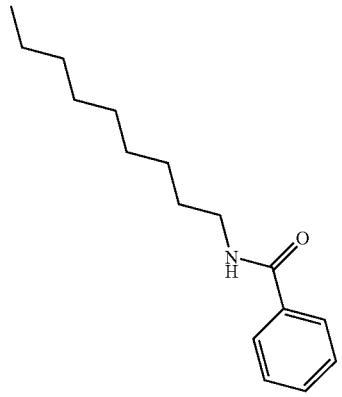 | 286.1683 |
| 121 | U.S. Pat. No. 6,756,382 Example 187 |  | 460.2737 |

TABLE 3-continued

| Example | Reference Formula III | R₁ | Measured Mass (M + H) |
|---|---|---|---|
| 122 | U.S. Pat. No. 6,677,349 Example 247 | butyl-NH-S(O)₂-CH₃ | 364.1446 |
| 123 | U.S. Pat. No. 6,573,273 Example 158 | butyl-NH-C(O)-NH-cyclohexyl | 411.2505 |
| 124 | U.S. Pat. No. 6,756,382 Example 190 | 2,2-dimethylbutyl-NH-C(O)-phenyl | 418.2275 |
| 125 | U.S. Pat. No. 6,664,264 Example 16 | hexyl-S(O)₂-CH₃ | 377.1655 |
| 126 | U.S. Pat. No. 6,573,273 Example 162 | butyl-NH-C(O)-NH-propyl | 385.2358 |

TABLE 3-continued

| Example | Reference Formula III | R₁ | Measured Mass (M + H) |
|---|---|---|---|
| 127 | U.S. Pat. No. 6,677,349 Example 253 | butyl-NH-SO₂-(4-methylphenyl) | 440.1720 |
| 128 | U.S. Pat. No. 6,573,273 Example 163 | butyl-NH-C(O)-morpholine | 399.2145 |
| 129 | U.S. Pat. No. 6,677,349# | 2,2-dimethylbutyl-NH₂ | 314.1980 |
| 130 | U.S. Pat. No. 6,573,273 Example 169 | 2-methyl-2-ethylpropyl-NH-C(O)-NH-phenyl | 433.2321 |
| 131 | U.S. Pat. No. 6,677,349 Example 256 | 2-methyl-2-ethylpropyl-NH-SO₂-CH₃ | 392.1757 |

TABLE 3-continued

Structures shown: Xa (2-(2-methoxyethyl)-1H-imidazo[4,5-c]quinolin-4-amine with R₁) converted to Ia (2-(2-hydroxyethyl) analog with R₁).

| Example | Reference Formula III | R₁ | Measured Mass (M + H) |
|---|---|---|---|
| 132 | U.S. Pat. No. 6,756,382 Example 196 | butyl-NH-C(O)-phenyl | 390.1929 |
| 133 | U.S. Pat. No. 6,683,088 Example 3 | propyl-O-CH₂CH₂-N(CH₃)-S(O)₂-CH₃ | 408.1714 |
| 134 | U.S. Pat. No. 6,664,265 Example 8 | propyl-O-CH₂CH₂-N(CH₃)-C(O)-phenyl | 434.2197 |
| 135 | U.S. Pat. No. 6,664,265 Example 73 | propyl-O-CH₂CH₂-N(CH₃)-C(O)-cyclohexyl | 440.2672 |
| 136 | U.S. Pat. No. 6,677,349[#] | propyl-NH-S(O)₂-CH₃ | 350.1316 |

TABLE 3-continued

| Example | Reference Formula III | R₁ | Measured Mass (M + H) |
|---|---|---|---|
| 137 | U.S. Pat. No. 6,573,273# | propyl-NH-C(O)-NH-ethyl | 343.1884 |
| 138 | U.S. Pat. No. 6,451.810# | propyl-NH-C(O)-CH₂-CH(CH₃)₂ | 356.2078 |
| 139 | U.S. Pat. No. 6,677,349# | ethyl-C(CH₃)₂-NH-S(O)₂-CH₃ | 378.1595 |
| 140 | U.S. Patent Publication 2004/0091491 IRM3 | -CH₂CH₂-O-CH₂CH₂-NH-C(O)-(CH₂)₁₄-CH₃ | 554.4064 |

Although not specifically exemplified the compound can be readily prepared using the disclosed synthetic routes.

Example 141

N-{3-[4-Amino-2-(2-hydroxyethyl)-1H-imidazo[4,5-c]quinolin-1-yl]propyl}-2-methylpropionamide

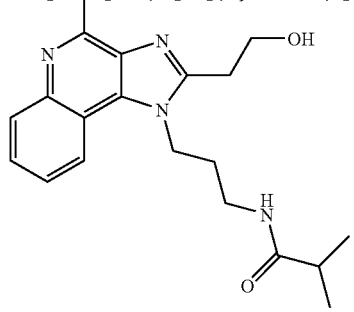

Part A 1-(3-Aminopropyl)-2-(2-methoxyethyl)-1H-imidazo[4,5-c]quinolin-4-amine dihydrochloride (6 g, 16 mmol) was combined with triethylamine (11.2 mL, 80 mmol) and pyridine (100 mL). Isobutyryl chloride (1.9 g, 18 mmol) was added dropwise and the reaction mixture was stirred at ambient temperature for 1 hour. The reaction mixture was combined with saturated aqueous sodium bicarbonate and extracted with dichloromethane (3×200 mL). The combined organics were dried over magnesium sulfate, filtered through a layer of CELITE filter aid, and then concentrated under reduced pressure to provide 6.2 g of crude N-{3-[4-amino-2-(2-methoxyethyl)-1H-imidazo[4,5-c]quinolin-1-yl]propyl}-2-methylpropionamide as a brown solid.

Part B

The material from Part A was combined with dichloromethane (40 mL), stirred until homogeneous, and then chilled in an ice bath. Boron tribromide (40 mL of 1 M in dichloromethane) was slowly added. The ice bath was removed and the reaction mixture was stirred overnight at ambient temperature. The reaction mixture was concentrated under reduced pressure. The residue was combined with methanol (50 mL) and hydrochloric acid (50 mL of 6 N) and heated at 50° C. for 2 hours. The solution was adjusted to pH 9 with sodium hydroxide (6 M) and then extracted first with ethyl acetate (3×100 mL) and then with dichloromethane. The organics were dried over magnesium sulfate, filtered through a layer of CELITE filter aid, and then concentrated under reduced pressure. The residue was purified by prep HPLC (HORIZON HPFC system, eluting with a gradient of 0-10% methanol in dichloromethane), recrystallized from acetonitrile, and then dried in a vacuum oven to provide 208 mg of N-{3-[4-amino-2-(2-hydroxyethyl)-1H-imidazo[4,5-c]quinolin-1-yl]propyl}-2-methylpropionamide as an off-white solid, mp 196-198° C. Anal. calcd for $C_{19}H_{25}N_5O_2$: % C, 64.20; % H, 7.09; % N, 19.70. Found: % C, 63.99; % H, 7.28; % N, 19.63.

Example 142

1-[2-(4-Amino-2-hydroxymethyl-1H-imidazo[4,5-c]quinolin-1-yl)-1,1-dimethylethyl]-3-(1-methylethyl)urea

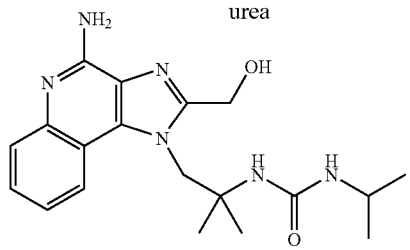

Part A

Under a nitrogen atmosphere, a solution of 1,2-diamino-2-methylpropane (52.20 mL, 503.3 mmol), triethylamine (131.8 mL, 958.8 mmol), and dichloromethane (1.0 L) was chilled in an ice water bath. 4-Chloro-3-nitroquinoline (100.0 g, 479.4 mmol) was added in portions over a period of 5 minutes. The reaction mixture was stirred at 0° C. for 2 hours and then allowed to slowly warm to ambient temperature. After 16 hours the reaction mixture was concentrated under reduced pressure. The residue was triturated with water (500 mL) for 1 hour. The resulting solid was isolated by filtration and dried overnight in a vacuum desiccator to provide 124.6 g of $N^1$-(3-nitroquinolin-1-yl)-2-methylpropane-1,2-diamine as a yellow crystalline solid.

Part B

Under a nitrogen atmosphere, a suspension of $N^1$-(3-nitroquinolin-1-yl)-2-methylpropane-1,2-diamine (60.0 g, 231 mmol) in dichloromethane (1.0 L) was chilled in an ice bath. Isopropyl isocyanate (23.8 mL, 242 mmol) was added dropwise over a period of 10 minutes. The reaction was allowed to slowly warm to room temperature. After 17 hours additional isopropyl isocyanate (about 2 mL) was added. After an additional 3 hours more isopropyl isocyanate (1 mL) was added. After 2 more hours the reaction mixture was concentrated under reduced pressure to provide 79.8 g of 1-{1,1-dimethyl-2-[(3-nitroquinolin-1-yl)amino]ethyl}-3-(1-methylethyl)urea as a bright yellow solid.

Part C

A pressure vessel was charged with the material from Part B, 5% Pt/C (4.24 g), and acetonitrile (1.5 L). The mixture was placed under hydrogen pressure for 20 hours and then filtered through a layer of CELITE filter aid. The filter cake was rinsed with additional acetonitrile. The filtrate was concentrated under reduced pressure. The residue was dissolved in toluene (750 mL) and then concentrated under reduced pressure to remove residual water. The toluene concentration was repeated. The residue was dissolved in dichloromethane (about 1 L), concentrated under reduced pressure, and then dried under high vacuum to provide 66.4 g of 1-{1,1-dimethyl-2-[(3-aminoquinolin-1-yl)amino]ethyl}-3-(1-methylethyl)urea as an orange foam.

Part D

Under a nitrogen atmosphere, a solution of 1-{1,1-dimethyl-2-[(3-aminoquinolin-1-yl)amino]ethyl}-3-(1-methylethyl)urea (66.0 g, 209 mmol) and triethylamine (32.1 mL, 230 mmol) in dichloromethane (1.0 L) was chilled in an ice bath. Ethoxyacetyl chloride (23.6 mL, 291 mmol) was added dropwise over a period of 10 minutes. The reaction mixture was allowed to slowly warm to ambient temperature overnight. The reaction mixture was concentrated under reduced pressure. The residue was combined with 1-butanol (800 mL) and triethylamine (87 mL, 627 mmol) and heated at 140° C. for 3 hours. The reaction mixture was cooled to ambient temperature and then concentrated under reduced pressure to provide a light brown foam. This material was purified by column chromatography (silica gel, eluting with 98/2/0.5 chloroform/methanol/ammonium hydroxide) to provide 29.36 g of 1-[2-(2-ethoxymethyl-1H-imidazo[4,5-c]quinolin-1-yl)-1,1-dimethylethyl]-3-(1-methylethyl)urea as a light yellow foam.

Part E

3-Chloroperoxybenzoic acid (26.33 g of 60%, 91.56 mmol) was added in portions over a period of 5 minutes to a chilled solution of the material from Part D in chloroform (350 mL). The reaction mixture was allowed to slowly warm to ambient temperature. After 2 hours the reaction mixture was chilled in an ice bath and ammonium hydroxide (100 mL) was added with vigorous stirring to homogenize. Para-toluenesulfonyl chloride (15.27 g, 80.12 mmol) was added in portions over a period of 10 minutes. The ice bath was removed and the reaction mixture was stirred for 30 minutes. The reaction mixture was diluted with water (100 mL) and chloroform (250 mL). The layers were separated. The organic layer was washed with 10% sodium carbonate (200 mL) and water (200 mL). The combined aqueous was back extracted with chloroform (100 mL). The combined organics were washed with brine (200 mL), dried over magnesium sulfate, filtered, and then concentrated under reduced pressure to provide a light brown foam. The foam was purified by column chromatography (silica gel, eluting with 95/5 chloroform/methanol) and then recrystallized from acetonitrile to provide 3.75 g of 1-[2-(4-amino-2-ethoxymethyl-1H-imidazo[4,5-c]quinolin-1-yl)-1,1-dimethylethyl]-3-(1-methylethyl)urea as an off white solid.

Part F

Under a nitrogen atmosphere, a suspension of 1-[2-(4-amino-2-ethoxymethyl-1H-imidazo[4,5-c]quinolin-1-yl)-1,1-dimethylethyl]-3-(1-methylethyl)urea (1.19 g, 2.99 mmol) in dichloromethane (30 mL) was chilled in an ice bath. Boron tribromide (7.47 mL of 1 M in dichloromethane) was added. The reaction mixture was allowed to warm slowly to ambient temperature and then stirred for 18 hours. Additional boron tribromide (2 eq) was added. After 2 hours the reaction mixture was diluted with acetonitrile (10 mL) and the reaction mixture was stirred overnight. The reaction mixture was diluted with dichloromethane (10 mL) and acetonitrile (10 mL), stirred for an additional 16 hours, quenched with methanol (25 mL), and then concentrated under reduced pressure to provide an orange foam. The foam was dissolved in hydrochloric acid (25 mL of 6 N) and heated at 50° C. for 2 hours. The solution was neutralized with 50% sodium hydroxide. The resulting gummy precipitate was extracted with chloroform (3×15 mL). The combined organics were washed with brine (15 mL), dried over magnesium sulfate, filtered, and then concentrated under reduced pressure to provide an off white solid. This material was purified by prep HPLC (HORIZON HPFC system, eluting with a gradient of 15-50% CMA in chloroform) and then recrystallized from acetonitrile to provide 335 g of 1-[2-(4-amino-2-hydroxymethyl-1H-imidazo[4,5-c]quinolin-1-yl)-1,1-dimethylethyl]-3-(1-methylethyl)urea as a white crystalline solid, mp 196-199° C.; $^1$H NMR (300 MHz, DMSO-$d_6$) δ 8.38 (d, J=8.0 Hz, 1H), 7.59 (d, J=7.5 Hz, 1H), 7.43-7.38 (m, 1H), 7.24-7.19 (m, 1H), 6.54 (s, 2H), 5.72 (s, 1H), 5.63 (d, J=7.6 Hz, 1H), 5.46 (t, J=5.7 Hz, 1H), 5.01 (s, 2H), 4.78 (s, 2H), 3.78-3.67 (m, 1H), 1.17 (bs, 6H), 1.05 (d, J=6.9 Hz, 6H); $^{13}$C NMR (75 MHz, DMSO-$d_6$) δ 157.2, 154.2, 152.3, 145.6, 134.3, 126.8, 126.7, 121.5, 120.9, 115.8, 56.5, 54.2, 52.1, 26.4, 23.6; MS (APCI) m/z 371 (M+H)$^+$; Anal. Calcd for $C_{19}H_{26}N_6O_2 \cdot 0.3H_2O$: % C, 60.72; % H, 7.13; % N, 22.36. Found: % C, 60.44; % H, 7.42; % N, 22.52.

Example 143

{4-Amino-1-[2,2-dimethyl-3-(methylsulfonyl)propyl]-1H-imidazo[4,5-c]quinolin-2-yl}methanol

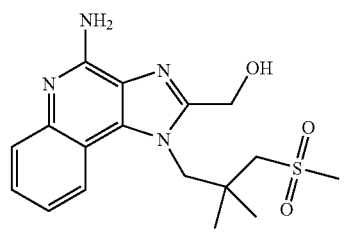

To a suspension of 1-[2,2-dimethyl-3-(methylsulfonyl)propyl]-2-(ethoxymethyl)-1H-imidazo[4,5-c]quinolin-4-amine (0.4 g, 1.02 mmol) in dichloromethane (5 mL) was added boron tribromide (5.1 mL, 1M solution in dichloromethane). An exotherm was observed upon addition and the mixture turned light purple. After stirring at ambient temperature for 20 hours, the remaining starting material was consumed by adding boron tribromide (2.5 mL, 1M solution in dichloromethane). The reaction was quenched with aqueous hydrochloric acid (1N, 20 mL) to afford a homogeneous mixture. The layers were separated and the aqueous layer washed with dichloromethane (20 mL). The pH of the aqueous layer was adjusted to 12 by addition of aqueous sodium hydroxide (50%) at which time a solid precipitated out of solution. The solid was stirred for 18 hours, collected by filtration and washed with water. The crude product was purified by chromatography over silica gel (eluting with CMA) to afford a white powder. The powder was triturated with methanol (20 mL). The resulting solid was isolated by filtration, washed with methanol and dried for 4 hours at 65° C. to provide 150 mg of {4-amino-1-[2,2-dimethyl-3-(methylsulfonyl)propyl]-1H-imidazo[4,5-c]quinolin-2-yl}methanol as a white powder, mp 230-232° C.

Anal. Calcd for $C_{17}H_{22}N_4O_3S$: % C, 56.33; % H, 6.12; % N, 15.46. Found: % C, 56.33; % H, 6.31; % N, 15.27.

Example 144

N-{2-[4-amino-2-(hydroxymethyl)-1H-imidazo[4,5-c]quinolin-1-yl]ethyl}-N'-isopropylurea

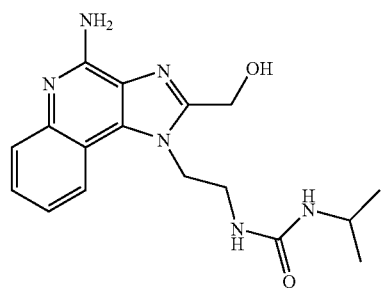

A stirring solution of N-{2-[4-amino-2-(ethoxymethyl)-1H-imidazo[4,5-c]quinolin-1-yl]ethyl}-N'-isopropylurea (400 mg, 1.1 mmol) in dichloromethane (50 mL) was sealed with a septum and purged with nitrogen gas. The solution was cooled in an ice/water bath and a 1.0 M solution of boron tribromide in dichloromethane (2.2 mL) was added via syringe. The resulting mixture was stirred for 2 hours while warming to ambient temperature. The mixture was cooled back to 0° C. in an ice/water bath and the second portion of boron tribromide (1.0 M, 5.5 mL) was added. The reaction was stirred for 18 hours while warming to ambient temperature. Aqueous hydrochloric acid (6N, 10 ml) was added and the mixture was stirred for 1 hour. The layers were separated and the aqueous fraction was neutralized by the slow addition of solid sodium hydroxide until the pH reached 14. A fine precipitate formed. The aqueous mixture was extracted with chloroform (2×50 mL) and filtered. The resulting solid (filter cake) was combined with the organic extracts, methanol (50 mL), and silica gel (5 g). The mixture was concentrated under reduced pressure. The crude product absorbed on silica was purified by chromatography using a HORIZON HPFC system (silica cartridge, eluting with 0-35% CMA in chloroform over 2.6 L) followed by recrystallization from acetonitrile to provide 170 mg of N-{2-[4-amino-2-(hydroxymethyl)-1H-imidazo[4,5-c]quinolin-1-yl]ethyl}-N'-isopropylurea as an off-white solid, mp>240° C.

$^1$H NMR (500 MHz, DMSO-$d_6$) δ 8.30 (d, J=7.9 Hz, 1H), 7.61 (dd, J=8.3, 0.9 Hz, 1H), 7.43 (m, 1H), 7.24 (m, 1H), 6.53 (br s, 2H), 5.99 (t, J=5.8 Hz, 1H), 5.82 (d, J=7.8 Hz, 1H), 5.67 (d, J=5.8 Hz, 1H), 4.75 (d, J=5.8 Hz, 2H), 4.66 (t, J=6.7 Hz, 2H), 3.69 (m, 1H), 3.48 (q, J=6.4 Hz, 2H), 1.01 (d, J=6.5 Hz, 6H);

MS (APCI) m/z 343 (M+H)$^+$;

Anal. Calcd. for $C_{17}H_{22}N_6O_2$: % C, 59.63; % H, 6.48; % N, 24.54. Found: % C, 59.64; % H, 6.59; % N, 24.58.

Example 145

N-{4-[4-amino-2-(hydroxymethyl)-1H-imidazo[4,5-c]quinolin-1-yl]butyl}cyclopentanecarboxamide

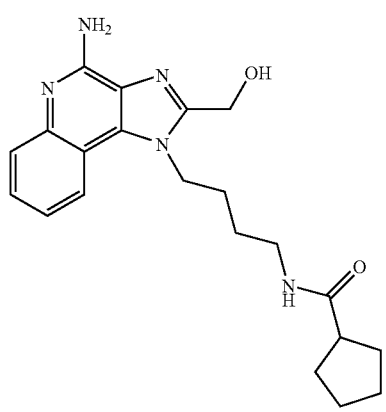

Boron tribromide (2.5 equivalents, 14.6 mL of 1 M solution in dichloromethane) was added dropwise to a cooled (ice bath) suspension of N-{4-[4-amino-2-(ethoxymethyl)-1H-imidazo[4,5-c]quinolin-1-yl]butyl}cyclopentanecarboxamide (2.4 g, 5.8 mmol) in dichloromethane (25 mL). The reaction mixture was allowed to slowly warm to ambient temperature and then stirred for 6 days. Additional boron tribromide (5 equivalents, 29 mmol, 29 mL) was added and the reaction was stirred at ambient until starting material was consumed. The reaction was quenched slowly with methanol (100 mL) and then concentrated under reduced pressure. The residue was combined with 6 M hydrochloric acid (100 mL), heated to 50° C., and stirred for 2 hours. The resulting solution was cooled (ice bath) and then free-based (pH 9) with the addition of 6 M aqueous sodium hydroxide. A brown gummy solid formed in the basic aqueous solution. The aqueous liquid was decanted from the solid and acetonitrile was added (30 mL). A white precipitate formed and was isolated by filtration. The white precipitate was then triturated with hot acetonitrile, allowed to cool, isolated by filtration, washed with ether, and dried under vacuum to provide N-{4-[4-amino-2-(hydroxymethyl)-1H-imidazo[4,5-c]quinolin-1-yl]butyl}cyclopentanecarboxamide (0.48 g) as a fine white solid, mp 183-186° C.; MS (ESI) m/z 382 (M+H)$^+$; Anal. Calcd for $C_{21}H_{27}N_5O_2$: C, 65.35; H, 7.18; N, 18.14; Found C, 65.06; H, 6.90; N, 18.13.

Example 146

N-[4-(4-amino-2-hydroxymethyl-1H-imidazo[4,5-c]quinolin-1-yl)butyl]isobutyramide

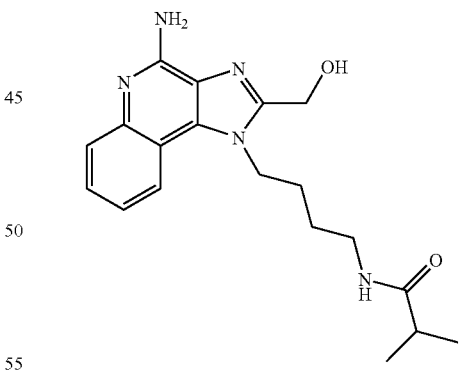

Boron tribromide (2.5 equivalents, 15.6 mL of 1 M solution in dichloromethane) was added dropwise to a cooled (ice bath) suspension of N-[4-(4-amino-2-ethoxymethyl-1H-imidazo[4,5-c]quinolin-1-yl)butyl]isobutyramide (2.4 g, 6.2 mmol) in dichloromethane (25 mL). The reaction mixture was allowed to slowly warm to ambient temperature and then stirred for 1 day. Additional boron tribromide (5 equivalents, 31 mmol, 31 mL) was added to the mixture. The reaction was quenched slowly with methanol (100 mL) and then concentrated under reduced pressure. The residue was combined with 6 M hydrochloric acid (100 mL), heated to 50° C., and stirred for 2 hours. The resulting solution was cooled (ice bath) and then free-based (pH 9) with the addition of 6 M sodium hydroxide. A brown gummy solid formed in the basic aqueous solution. The resulting solid was extracted with dichloromethane (6×50 mL). The combined extracts were washed with brine (100 mL), dried with magnesium sulfate, filtered, and then concentrated under reduced pressure. This material was purified by prep HPLC (Analogix Separation System, Biotage Si 40+M column, eluted with a gradient of 0-20% methanol in dichloromethane with 1% ammonium hydroxide) to provide a light brown solid. The solid was triturated with hot acetonitrile, allowed to cool, isolated by filtration, washed with ether, and dried under vacuum to provide N-[4-(4-amino-2-hydroxymethyl-1H-imidazo[4,5-c]quinolin-1-yl)butyl]isobutyramide (0.049 g) as a white solid, mp 222-224° C.; MS (ESI) m/z 356 (M+H)$^+$; Anal. Calcd for $C_{19}H_{25}N_5O_2$.0.25HBr.0.10$H_2O$: C, 60.46; H, 6.80; N, 18.55; Found C, 60.26; H, 6.64; N, 18.43.

Example 147

N-[4-(4-amino-2-hydroxymethyl-1H-imidazo[4,5-c]quinolin-1-yl)butyl]methanesulfonamide

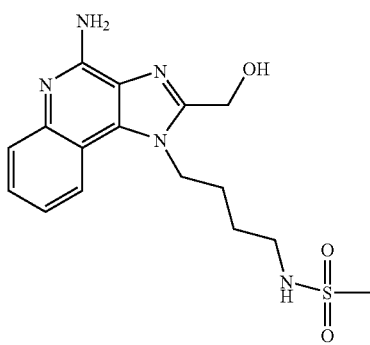

Boron tribromide (2.5 equivalents, 20 mL of 1 M solution in dichloromethane) was added dropwise to a cooled (ice bath) suspension of N-[4-(4-amino-2-ethoxymethyl-1H-imidazo[4,5-c]quinolin-1-yl)butyl]methanesulfonamide (3 g, 7.92 mmol) in dichloromethane (20 mL). The reaction mixture was allowed to slowly warm to ambient temperature and then stirred for 4 hours. Additional boron tribromide (2 mL) was added and the mixture was stirred for 3 hours. The reaction was quenched slowly with methanol (20 mL) and then concentrated under reduced pressure. The residue was combined with 6 M hydrochloric acid (50 mL), heated to 50° C., and stirred for 2 hours. The resulting solution was concentrated under reduced pressure to a slurry that cooled (ice bath) and then free-based with the addition of 7 M ammonia in methanol (40 mL). The mixture was concentrated under reduced pressure and the addition of 7 M ammonia in methanol (40 mL) was repeated 2 more times. The concentrated brown sludge like material was purified by prep HPLC (ISCO Combiflash Separation System, Biotage Si 40+M column, eluted with a gradient of methanol in dichloromethane with 1% ammonium hydroxide) to provide a light brown solid. The solid was triturated with hot acetonitrile, allowed to cool, isolated by filtration, washed with ether, and dried under vacuum to provide N-[4-(4-amino-2-hydroxymethyl-1H-imidazo[4,5-c]quinolin-1-yl)butyl]methanesulfonamide (0.1 g) as a fine beige solid, mp 216-219° C.; MS (ESI) m/z 364 (M+H)$^+$; Anal. Calcd for $C_{16}H_{21}N_5O_3S$: C, 52.88; H, 5.82; N, 19.27; Found C, 52.62; H, 5.71; N, 19.02.

Example 148

(4-Amino-1-{4-[(methylsulfonyl)amino]butyl}-1H-imidazo[4,5-c]quinolin-2-yl)methyl N-[(benzyloxy)carbonyl]-L-valinate

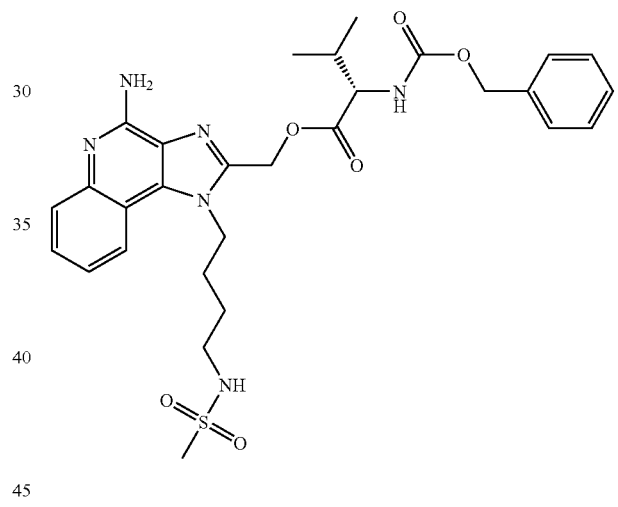

To a stirred suspension of N-[4-(4-amino-2-hydroxymethyl-1H-imidazo[4,5-c]quinolin-1-yl)butyl]methanesulfonamide (2.1 g, 5.8 mmol) in THF was added triphenylphosphine (1.5 equivalents, 8.7 mmol, 2.2 g) followed by CBZ-L-valine (1.5 equivalents, 8.7 mmol, 2.3 g). The suspension was stirred for 5 min after which it was cooled in an ice-bath. To this cooled reaction mixture diisopropyl azodicarboxylate (DIAD, 1.8 equivalents, 10.4 mmol, 2.0 mL) was added and the reaction was warmed to room temperature and stirred overnight. The solvent was evaporated under reduced pressure and the crude solid was purified by prep HPLC (ISCO Combiflash Separation System, Biotage Si 40+M column, eluted with a gradient of 0-8% methanol in dichloromethane with 1% ammonium hydroxide) to provide a solid. The solid was heated in diethyl ether and filtered to afford (4-amino-1-{4-[(methylsulfonyl)amino]butyl}-1H-imidazo[4,5-c]quinolin-2-yl)methyl N-[(benzyloxy)carbonyl]-L-valinate (2 g) as a beige solid, mp 99-100° C.; MS (ESI) m/z 597 (M+H)$^+$; Anal. Calcd for $C_{29}H_{36}N_6O_6S$: C, 58.37; H, 6.08; N, 14.08; Found C, 57.98; H, 6.31; N, 13.82.

Example 149

(4-Amino-1-{4-[(methylsulfonyl)amino]butyl}-1H-imidazo[4,5-c]quinolin-2-yl)methyl L-valinate

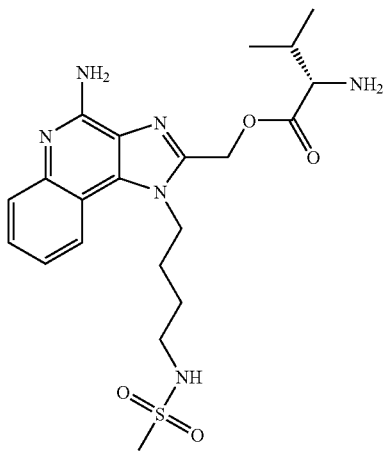

To a hydrogenation bottle was added (4-amino-1-{4-[(methylsulfonyl)amino]butyl}-1H-imidazo[4,5-c]quinolin-2-yl) methyl N-[(benzyloxy)carbonyl]-L-valinate (1.5 g, 2.5 mmol) followed by a mixture of methanol (30 mL), THF (15 mL) and water (5 mL) and conc HCl (5 mL). To this was added Pd/C (90 mg) and the reaction was hydrogenated at 40 psi (2.8×10$^5$ Pa) overnight. To the reaction mixture was added conc. HCl (5 mL) and Pd/C (90 mg) and the reaction was hydrogenated at 40 psi (2.8×10$^5$ Pa) for 18 hours. The reaction was filtered through CELITE filter aid and the filtrate was evaporated to afford a clear oil. The product was isolated by prep HPLC (ISCO Combiflash Separation System, Biotage Si 40+M column, eluted with a gradient of 0-8% methanol in dichloromethane with 1% ammonium hydroxide) to provide (4-amino-1-{4-[(methylsulfonyl)amino]butyl}-1H-imidazo [4,5-c]quinolin-2-yl)methyl L-valinate (0.495 g) as an off white solid, mp 161-163° C.; MS (ESI) m/z 463 (M+H)$^+$; Anal. Calcd for $C_{21}H_{30}N_6O_4S$: C, 54.53; H, 6.54; N, 18.17; Found C, 53.96; H, 6.62; N, 17.85, delta C=0.57.

Example 150

[4-Amino-1-(tetrahydro-2H-pyran-4-ylmethyl)-1H-imidazo[4,5-c]quinolin-2-yl]methanol

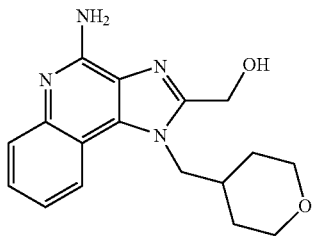

Part A

Under a nitrogen atmosphere THF (90 mL) and triethylamine (17.5 mL, 125.6 mmol) were added sequentially to a mixture of crude 4-chloro-3-nitroquinoline (13.10 g, 62.81 mmol) and 1-tetrahydro-2H-pyran-4-ylmethylamine hydrochloride (10.0 g, 65.95 mmol). The reaction mixture was placed in an oil bath at 45° C. for 1 hour and then concentrated under reduced pressure. The residue was diluted with THF (30 mL) and water (200 mL). The THF was removed under reduced pressure. A solid was isolated by filtration and dried to provide 16.10 g of 3-nitro-N-(tetrahydro-2H-pyran-4-ylmethyl)quinolin-4-amine as a light yellow solid.

Part B

A mixture of 3-nitro-N-(tetrahydro-2H-pyran-4-ylmethyl) quinolin-4-amine (2.50 g), 10% palladium on carbon (0.25 g), and ethanol (40 mL) was placed under hydrogen pressure on a Parr apparatus. When the reaction was complete, the mixture was filtered through a layer of CELITE filter agent. The filter cake was washed with ethanol. The filtrate was concentrated under reduced pressure to provide 2.23 g of N$^4$-(tetrahydro-2H-pyran-4-ylmethyl)quinoline-3,4-diamine as a yellowish-orange oil.

Part C

Chloroacetyl chloride (12 mL, 151 mmol) was dissolved in dichloromethane (30 mL) and added via addition funnel, over 20 minutes, to a stirring solution of N$^4$-(tetrahydro-2H-pyran-4-ylmethyl)quinoline-3,4-diamine (35.3 g, 137 mmol) in dichloromethane (300 mL). The resulting solution was stirred at ambient temperature under nitrogen for 24 hours at which point the solution was heated to 40° C. for an additional 24 hours. The mixture was cooled to ambient temperature, diluted with dichloromethane (150 mL) and transferred to a separatory funnel. The organic layer was washed with water (2×200 mL) and brine (2×200 mL), dried over magnesium sulfate, filtered and concentrated under reduced pressure to provide 38.3 g of 2-(chloromethyl)-1-(tetrahydro-2H-pyran-4-ylmethyl)-1H-imidazo[4,5-c]quinoline as a light brown solid.

Part D

3-Chloroperoxybenzoic acid (mCPBA) (3.8 g of 77% pure material, 14.2 mmol) was added to a stirring solution of 2-(chloromethyl)-1-(tetrahydro-2H-pyran-4-ylmethyl)-1H-imidazo[4,5-c]quinoline (3.0 g, 9.50 mmol) in dichloromethane (60 mL). After 15.5 hours, ammonium hydroxide (12 mL) and then p-toluenesulfonyl chloride (2.2 g, 11.4 mmol) were added to the stirring solution and the biphasic mixture was stirred at ambient temperature for 3 hours. The reaction was diluted with water (50 mL) and then transferred to a separatory funnel. The aqueous layer was extracted with dichloromethane (3×100 mL) and the combined organic fractions dried over magnesium sulfate, filtered and concentrated under reduced pressure. The residue was purified by column chromatography using a HORIZON HPFC system (silica cartridge, eluting with 3-20% methanol in dichloromethane) to provide 1.6 g of 2-(chloromethyl)-1-(tetrahydro-2H-pyran-4-ylmethyl)-1H-imidazo[4,5-c]quinolin-4-amine as a yellow solid.

Part E

Potassium acetate (0.41 g, 4.16 mmol) and potassium iodide (0.28 g, 1.66 mmol) were added to a stirring solution of 2-(chloromethyl)-1-(tetrahydro-2H-pyran-4-ylmethyl)-1H-imidazo[4,5-c]quinolin-4-amine (0.55 g, 1.66 mmol) and the resulting suspension was heated to 50° C. After 17 hours, the suspension was cooled to ambient temperature and concentrated under reduced pressure. The residue was suspended in methanol (10 mL) and water (5 mL) and lithium hydroxide monohydrate (0.35 g, 8.31 mmol) was added in one portion.

The resulting solution was stirred at ambient temperature 18 hours and concentrated under reduced pressure. The residue was diluted with water (20 mL) and neutralized with hydrochloric acid (6 N in water). The aqueous layer was extracted with dichloromethane (2×50 mL) and ethyl acetate (50 mL). The combined organic fractions were concentrated to a yellow solid which was crystallized from acetonitrile. The crystals were isolated by filtration and dried in a vacuum oven at 65° C. to provide 0.20 g of [4-amino-1-(tetrahydro-2H-pyran-4-ylmethyl)-1H-imidazo[4,5-c]quinolin-2-yl]methanol as an off-white solid, mp 239-241° C.

Anal. calcd for $C_{17}H_{20}N_4O_2 \cdot 0.2H_2O$: C, 64.62; H, 6.51; N, 17.73. Found: C, 64.45; H, 6.69; N, 17.62.

Examples 151-229

Part A

A solution of 1-(4-aminobutyl)-2-methoxymethyl-1H-imidazo[4,5-c]quinoline-4-amine (30 mg, 1 eq, prepared according to the general method of Example 3 using methoxyacetyl chloride in lieu of 3-methoxypropionyl chloride) and N,N-diisopropylethylamine (2 eq) in N,N-dimethylacetamide (1 mL) was added to a tube containing a reagent (1.1 eq) from the table below. The reaction mixture was vortexed overnight and then quenched with water (100 μL). The solvents were removed by vacuum centrifugation. The residue was purified by solid-supported liquid-liquid extraction according to the following procedure. The sample was dissolved in chloroform (1 mL) then loaded onto diatomaceous earth that had been equilibrated with 1 M sodium hydroxide (600 μL) for about 20 minutes. After 10 minutes chloroform (500 μL) was added to elute the product from the diatomaceous earth into a well of a collection plate. After an additional 10 minutes the process was repeated with additional chloroform (500 μL). The solvent was then removed by vacuum centrifugation.

Part B

The residue (in a test tube) was combined with dichloromethane (500 μL) and the tube was vortexed to dissolve the solids. The solution was cooled (0° C.) and then combined with boron tribromide (400 μL of 1 M in dichloromethane). The mixture was vortexed for 5 minutes, chilled for 30 minutes, and then vortexed at ambient temperature for 64 hours. Additional dichloromethane (500 μL) and boron tribromide (400 μL of 1 M in dichloromethane) were added and the mixture was vortexed overnight. The solvent was then removed by vacuum centrifugation. The residue was diluted with methanol (500 μL) and hydrochloric acid (500 μL of 6 N). The solvents were removed by vacuum centrifugation. The compounds were purified according to the method described in Examples 8-72. The table below shows the reagent used for each example, the structure of the resulting compound, and the observed accurate mass for the isolated trifluoroacetate salt.

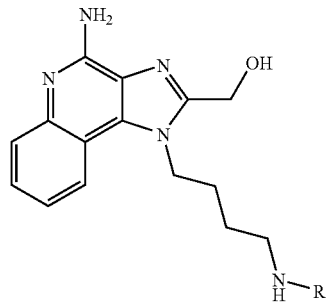

| Example | Reagent | R | Measured Mass (M + H) |
|---|---|---|---|
| 151 | None | —H | 286.1658 |
| 152 | Cyclopropanecarbonyl chloride | —C(O)-cyclopropyl | 354.1907 |
| 153 | Methoxyacetyl chloride | —C(O)CH₂OH | 344.1699 |
| 154 | Cyclobutanecarbonyl chloride | —C(O)-cyclobutyl | 368.2050 |

-continued
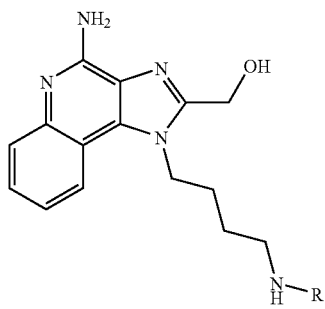
| Example | Reagent | R | Measured Mass (M + H) |
|---|---|---|---|
| 155 | Isovaleryl chloride | 2CH2C(O)-) | 370.2206 |
| 156 | Pentanoyl chloride | -) | 370.2208 |
| 157 | Benzoyl chloride | -) | 390.1909 |
| 158 | Cyclohexanecarbonyl chloride | -) | 396.2412 |
| 159 | Cyclopentylacetyl chloride | -) | 396.2411 |
| 160 | m-Toluoyl chloride | -) | 404.2069 |
| 161 | o-Toluoyl chloride | -) | 404.2072 |

-continued
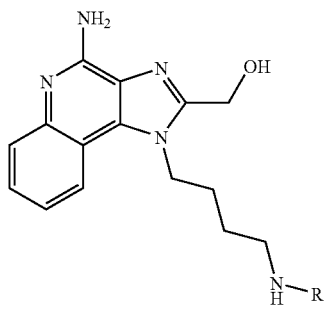
| Example | Reagent | R | Measured Mass (M + H) |
|---|---|---|---|
| 162 | p-Toluoyl chloride | (4-methylbenzoyl) | 404.2108 |
| 163 | Phenylacetyl chloride | (phenylacetyl) | 404.2056 |
| 164 | Dimethylaminoacetyl chloride hydrochloride | (dimethylaminoacetyl) | 371.2157 |
| 165 | 2-Fluorobenzoyl chloride | (2-fluorobenzoyl) | 408.1819 |
| 166 | 3-Fluorobenzoyl chloride | (3-fluorobenzoyl) | 408.1811 |
| 167 | 4-Fluorobenzoyl chloride | (4-fluorobenzoyl) | 408.1819 |

-continued
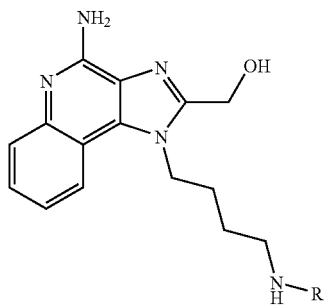
| Example | Reagent | R | Measured Mass (M + H) |
|---|---|---|---|
| 168 | 3-Cyanobenzoyl chloride | 3-cyanobenzoyl | 415.1847 |
| 169 | Hydrocinnamoyl chloride | hydrocinnamoyl | 418.2200 |
| 170 | 2-Methoxybenzoyl chloride | 2-hydroxybenzoyl | 406.1880 |
| 171 | 3-Methoxybenzoyl chloride | 3-hydroxybenzoyl | 406.1876 |
| 172 | p-Anisoyl chloride | 4-hydroxybenzoyl | 406.1860 |
| 173 | 3-Chlorobenzoyl chloride | 3-chlorobenzoyl | 424.1517 |

-continued

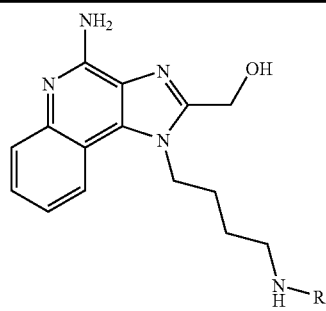

| Example | Reagent | R | Measured Mass (M + H) |
|---|---|---|---|
| 174 | 4-Chlorobenzoyl chloride | 4-chlorobenzoyl | 424.1525 |
| 175 | Isonicotinoyl chloride hydrochloride | pyridin-4-ylcarbonyl | 391.1874 |
| 176 | Nicotinoyl chloride hydrochloride | pyridin-3-ylcarbonyl | 391.1895 |
| 177 | Picolinoyl chloride hydrochloride | pyridin-2-ylcarbonyl | 391.1846 |
| 178 | trans-2-Phenyl-1-cyclopropanecarbonyl chloride | trans-2-phenylcyclopropanecarbonyl | 430.2213 |
| 179 | Methanesulfonyl chloride | methanesulfonyl | 364.1421 |
| 180 | Ethanesulfonyl chloride | ethanesulfonyl | 378.1595 |

-continued
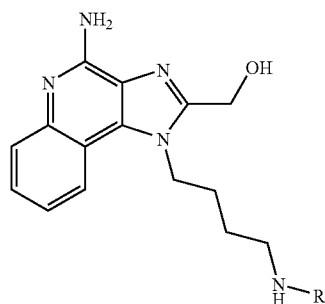
| Example | Reagent | R | Measured Mass (M + H) |
|---|---|---|---|
| 181 | 1-Propanesulfonyl chloride | | 392.1753 |
| 182 | Dimethylsulfamoyl chloride | | 393.1685 |
| 183 | 1-Butanesulfonyl chloride | | 406.1881 |
| 184 | Benzenesulfonyl chloride | | 426.1591 |
| 185 | 1-Methylimidazole-4-sulfonyl chloride | | 430.1668 |
| 186 | 2-Thiophenesulfonyl chloride | | 432.1135 |

-continued
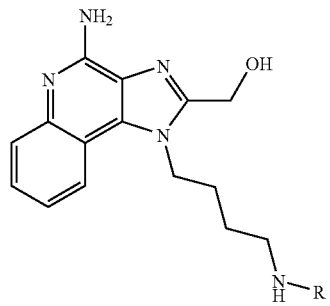
| Example | Reagent | R | Measured Mass (M + H) |
|---|---|---|---|
| 187 | 3-Methylbenzenesulfonyl chloride | 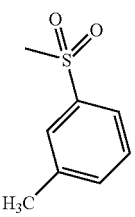 | 440.1728 |
| 188 | o-Toluenesulfonyl chloride | 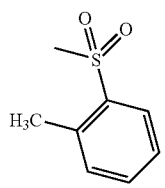 | 440.1758 |
| 189 | p-Toluenesulfonyl chloride | 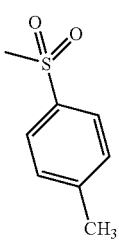 | 440.1766 |
| 190 | 2-Fluorobenzenesulfonyl chloride | 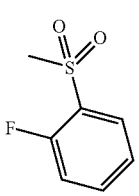 | 444.1479 |
| 191 | 3-Fluorobenzenesulfonyl chloride | 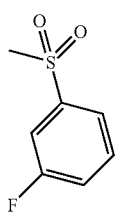 | 444.1517 |

-continued
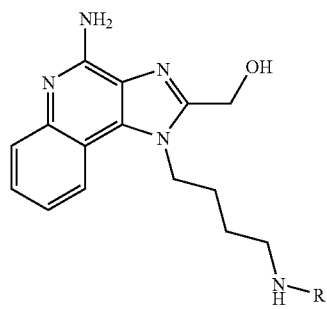
| Example | Reagent | R | Measured Mass (M + H) |
|---|---|---|---|
| 192 | 4-Fluorobenzenesulfonyl chloride | 4-F-C6H4-SO2- | 444.1496 |
| 193 | 3-Cyanobenzenesulfonyl chloride | 3-CN-C6H4-SO2- | 451.1568 |
| 194 | 4-Cyanobenzenesulfonyl chloride | 4-CN-C6H4-SO2- | 451.1579 |
| 195 | beta-Styrenesulfonyl chloride | PhCH=CH-SO2- | 452.1725 |
| 196 | 3-Methoxybenzenesulfonyl chloride | 3-HO-C6H4-SO2- | 442.1534 |

-continued
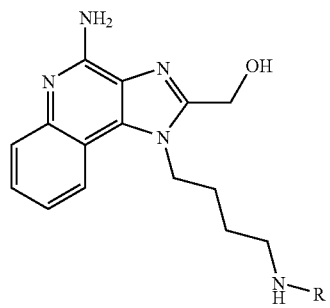
| Example | Reagent | R | Measured Mass (M + H) |
|---|---|---|---|
| 197 | 4-Methoxybenzenesulfonyl chloride | | 442.1557 |
| 198 | 2-Chlorobenzenesulfonyl chloride | | 460.1173 |
| 199 | 3-Chlorobenzenesulfonyl chloride | | 460.1242 |
| 200 | 4-Chlorobenzenesulfonyl chloride | | 460.1191 |
| 201 | 3-Pyridinesulfonyl chloride hydrochloride | | 427.1530 |

-continued
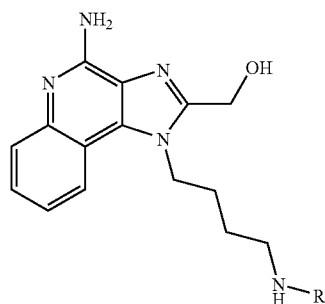
| Example | Reagent | R | Measured Mass (M + H) |
|---|---|---|---|
| 202 | 3,4-Dimethoxybenzenesulfonyl chloride | 3-hydroxy-4-hydroxyphenyl methylsulfonyl | 458.1452 |
| 203 | 3,4-Dichlorobenzenesulfonyl chloride | 3,4-dichlorophenyl methylsulfonyl | 494.0806 |
| 204 | Methyl isocyanate | —C(O)NH—CH₃ | 343.1862 |
| 205 | Ethyl isocyanate | —C(O)NH—CH₂CH₃ | 357.2018 |
| 206 | Isopropyl isocyanate | —C(O)NH—CH(CH₃)₂ | 371.2181 |
| 207 | n-Propyl isocyanate | —C(O)NH—CH₂CH₂CH₃ | 371.2187 |

-continued
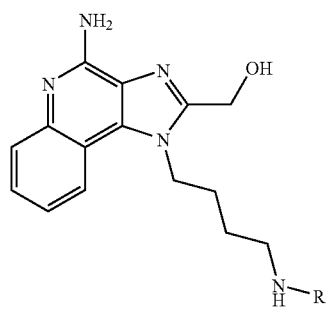
| Example | Reagent | R | Measured Mass (M + H) |
|---|---|---|---|
| 208 | n-Butyl isocyanate | -C(=O)-NH-(CH2)3-CH3 | 385.2314 |
| 209 | Cyclopentyl isocyanate | -C(=O)-NH-cyclopentyl | 397.2312 |
| 210 | Pentyl isocyanate | -C(=O)-NH-(CH2)4-CH3 | 399.2512 |
| 211 | Phenyl isocyanate | -C(=O)-NH-phenyl | 405.2047 |
| 212 | Cyclohexyl isocyanate | -C(=O)-NH-cyclohexyl | 411.2473 |
| 213 | 2-Fluorophenyl isocyanate | -C(=O)-NH-(2-fluorophenyl) | 423.1959 |

-continued

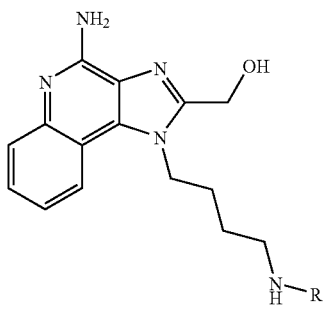

| Example | Reagent | R | Measured Mass (M + H) |
|---|---|---|---|
| 214 | 3-Fluorophenyl isocyanate | 3-fluorophenyl acetamide | 423.1924 |
| 215 | 4-Cyanophenyl isocyanate | 4-cyanophenyl acetamide | 430.1979 |
| 216 | (R)-(+)-alpha-Methylbenzyl isocyanate | (R)-alpha-methylbenzyl acetamide | 433.2370 |
| 217 | (S)-(−)-alpha-Methylbenzyl isocyanate | (S)-alpha-methylbenzyl acetamide | 433.2327 |
| 218 | 2-Phenylethylisocyanate | 2-phenylethyl acetamide | 433.2333 |
| 219 | 2-Methoxyphenyl isocyanate | 2-hydroxyphenyl acetamide | 421.2006 |

-continued

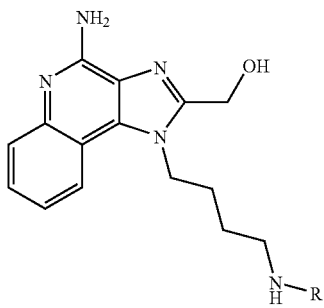

| Example | Reagent | R | Measured Mass (M + H) |
|---|---|---|---|
| 220 | 4-Methoxyphenyl isocyanate | acetamido-4-hydroxyphenyl | 421.1958 |
| 221 | 2-Chlorophenyl isocyanate | acetamido-2-chlorophenyl | 439.1650 |
| 222 | 4-Chlorophenyl isocyanate | acetamido-4-chlorophenyl | 439.1656 |
| 223 | trans-2-Phenylcyclopropyl isocyanate | acetamido-trans-2-phenylcyclopropyl | 445.2328 |
| 224 | N,N-Dimethylcarbamoyl chloride | N,N-dimethylacetamide | 357.2005 |
| 225 | 1-Pyrrolidinecarbonyl chloride | 1-pyrrolidinyl acetyl | 383.2168 |
| 226 | 1-Piperidinecarbonyl chloride | 1-piperidinyl acetyl | 397.2329 |

-continued

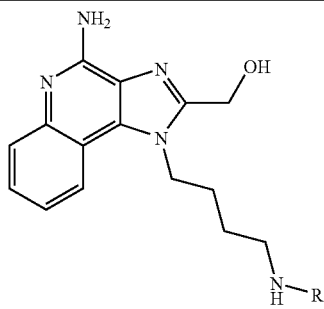

| Example | Reagent | R | Measured Mass (M + H) |
|---------|---------|---|------------------------|
| 227 | 4-Morpholinylcarbonyl chloride | ![morpholinylcarbonyl] | 399.2112 |
| 228 | 4-Methyl-1-Piperazinecarbonyl chloride | ![methylpiperazinecarbonyl] | 412.2439 |
| 229 | N-Methyl-N-phenylcarbamoyl chloride | ![methylphenylcarbamoyl] | 419.2167 |

Examples 230-245

Part A

A solution of 1-(2-amino-2-methylpropyl)-2-methoxymethyl-1H-imidazo[4,5-c]quinoline-4-amine (31 mg, 1 eq, prepared according to the general method of Example 3 using methoxyacetyl chloride in lieu of 3-methoxypropionyl chloride and tert-butyl N-{2-[(3-aminoquinolin-4-yl)amino]-1,1-dimethylethyl}carbamate in lieu of tert-butyl N-{4-[(3-aminoquinolin-4-yl)amino]butyl}carbamate) and N,N-diisopropylethylamine (2 eq) in N,N-dimethylacetamide (1 mL) was placed in a test tube. A reagent (1.1 eq) from the table below was added and the reaction mixture was vortexed overnight. The reaction was quenched with concentrated ammonium hydroxide (100 µL) and the solvents were removed by vacuum centrifugation.

Part B

The residue (in a test tube) was combined with dichloromethane (1 mL) and the tube was vortexed to dissolve the solids. The solution was cooled (0° C.) and then combined with boron tribromide (400 µL of 1 M in dichloromethane). The reaction was maintained at about 0° C. for 20 minutes. Methanol (1 mL) and hydrochloric acid (500 µL of 6 N) were added and the tube was vortexed for about 30 minutes. The solvents were removed by vacuum centrifugation. The compounds were purified according to the method described in Examples 8-72. The table below shows the reagent used for each example, the structure of the resulting compound, and the observed accurate mass for the isolated trifluoroacetate salt.

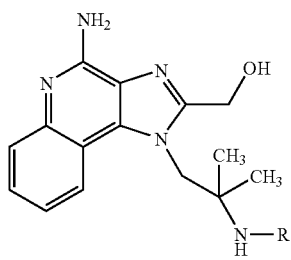

| Example | Reagent | R | Measured Mass (M + H) |
|---------|---------|---|------------------------|
| 230 | None | H | 286.1687 |

-continued

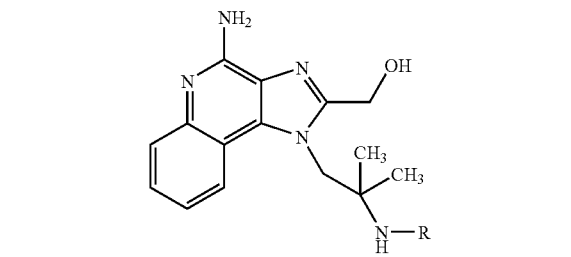

| Example | Reagent | R | Measured Mass (M + H) |
|---|---|---|---|
| 231 | Cyclopropanecarbonyl chloride | -C(=O)-cyclopropyl | 354.1936 |
| 232 | Butyryl chloride | -C(=O)CH₂CH₂CH₃ | 356.2094 |
| 233 | Isobutyryl chloride | -C(=O)CH(CH₃)₂ | 356.2119 |
| 234 | Cyclopentanecarbonyl chloride | -C(=O)-cyclopentyl | 382.2259 |
| 235 | Benzoyl chloride | -C(=O)-phenyl | 390.1908 |
| 236 | Nicotinoyl chloride hydrochloride | -C(=O)-(3-pyridyl) | 391.1844 |
| 237 | Methanesulfonyl chloride | -S(=O)₂CH₃ | 364.1414 |
| 238 | Benzenesulfonyl chloride | -S(=O)₂-phenyl | 426.1617 |

-continued

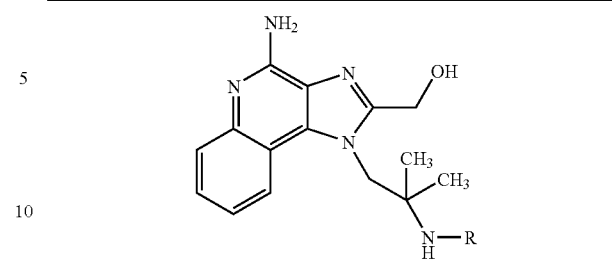

| Example | Reagent | R | Measured Mass (M + H) |
|---|---|---|---|
| 239 | 2,2,2-Trifluoroethanesulfonyl chloride | -S(=O)₂CH₂CF₃ | 432.1339 |
| 240 | 3-Fluorobenzenesulfonyl chloride | -S(=O)₂-(3-fluorophenyl) | 444.1523 |
| 241 | n-Propyl isocyanate | -C(=O)NH-CH₂CH₂CH₃ | 371.2215 |
| 242 | Cyclopentyl isocyanate | -C(=O)NH-cyclopentyl | 397.2327 |
| 243 | Phenyl isocyanate | -C(=O)NH-phenyl | 405.2063 |
| 244 | Cyclohexyl isocyanate | -C(=O)NH-cyclohexyl | 411.2515 |
| 245 | 3-Fluorophenyl isocyanate | -C(=O)NH-(3-fluorophenyl) | 423.1955 |

Examples 246-257

Part A

To a round-bottomed flask containing 1-(4-aminobutyl)-2-methoxymethyl-1H-imidazo[4,5-c]quinolin-4-amine (10.0 g, 33.4 mmol) was added methanol (160 mL) followed by acetic acid (40 mL). The reaction was stirred for 5 minutes and pyridine 3-carboxaldehyde (5.4 g, 50.1 mmol) was added and the reaction was stirred overnight at ambient temperature. Sodium cyanoborohydride (1 M in THF, 33.4 mL, 33.4 mmol) was added to the resultant imine in portions over 10 minutes. After 45 minutes the solvent was evaporated to afford an oil. To the oil was added saturated aqueous sodium bicarbonate (200 mL) and the aqueous layer was washed with ethyl acetate (200 mL) and dichloromethane (200 mL). The product was extracted from the aqueous with 20% methanol (2×100 mL) in dichloromethane. The organic layers were combined and the solvent evaporated to afford crude 2-methoxymethyl-1-{4-[(pyridin-3-ylmethyl)amino]butyl}-1H-imidazo[4,5-c]quinolin-4-amine (about 2 g). The aqueous layer was again extracted with 20% dimethylformamide (2×100 mL) in dichloromethane. The organic layers were combined and the solvent evaporated to afford crude 2-methoxymethyl-1-{4-[(pyridin-3-ylmethyl)amino]butyl}-1H-imidazo[4,5-c]quinolin-4-amine (about 2 g).

Part B

A solution of 2-methoxymethyl-1-{4-[(pyridin-3-ylmethyl)amino]butyl}-1H-imidazo[4,5-c]quinolin-4-amine (40 mg, 1 eq) and N,N-diisopropylethylamine (2 eq) in N,N-dimethylacetamide (1 mL) was added to a tube containing a reagent (1.1 eq) from the table below. The reaction mixture was vortexed for 4 hours and then quenched with water (50 µL). The solvents were removed by vacuum centrifugation. The residue was purified by solid-supported liquid-liquid extraction according to the following procedure. The sample was dissolved in chloroform (1 mL) then loaded onto diatomaceous earth that had been equilibrated with 1 M sodium hydroxide (600 µL) for about 20 minutes. After 10 minutes chloroform (500 µL) was added to elute the product from the diatomaceous earth into a well of a collection plate. After an additional 10 minutes the process was repeated with additional chloroform (500 µL). The solvent was then removed by vacuum centrifugation.

Part C

The residue (in a test tube) was combined with dichloromethane (500 µL) and the tube was vortexed to dissolve the solids. The solution was cooled (0° C.) and then combined with boron tribromide (400 µL of 1 M in dichloromethane). The mixture was vortexed for 10 minutes, chilled for 30 minutes, and then vortexed at ambient temperature overnight. The solvent was then removed by vacuum centrifugation. The residue was diluted with methanol (500 µL) and hydrochloric acid (500 µL of 6 N) and the mixture was vortexed for about 30 minutes. The solvents were removed by vacuum centrifugation. The compounds were purified according to the method described in Examples 8-72. The table below shows the reagent used for each example, the structure of the resulting compound, and the observed accurate mass for the isolated trifluoroacetate salt.

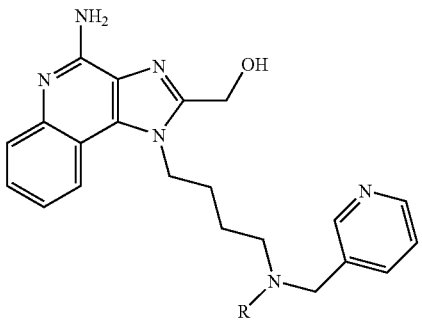

| Example | Reagent | R | Measured Mass (M + H) |
| --- | --- | --- | --- |
| 246 | None | H– | 377.2087 |
| 247 | Isobutyryl chloride | –C(O)CH(CH₃)₂ | 447.2468 |
| 248 | Cyclohexanecarbonyl chloride | –C(O)-cyclohexyl | 487.2783 |
| 249 | Phenylacetyl chloride | –C(O)CH₂Ph | 495.2465 |
| 250 | 4-Fluorobenzoyl chloride | –C(O)-(4-F-C₆H₄) | 499.2272 |
| 251 | 3-Methoxybenzoyl chloride | –C(O)-(3-HO-C₆H₄) | 497.2263 |

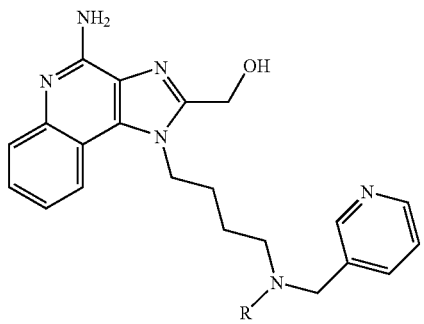

| Example | Reagent | R | Measured Mass (M + H) |
|---|---|---|---|
| 252 | 1-Methylimidazole-4-sulfonyl chloride | | 521.2071 |

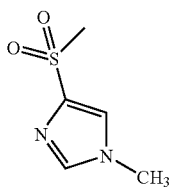

| | | | |
|---|---|---|---|
| 253 | 2,2,2-Trifluoroethanesulfonyl chloride | | 523.1717 |

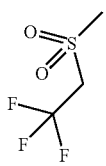

| 254 | alpha-Toluenesulfonyl chloride | | 531.2134 |

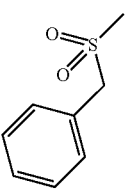

| 255 | 3-Methoxybenzenesulfonyl chloride | | 533.1941 |

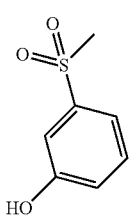

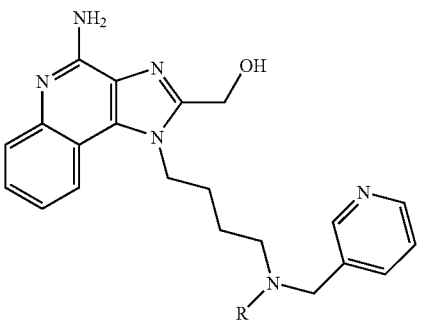

| Example | Reagent | R | Measured Mass (M + H) |
|---|---|---|---|
| 256 | Isopropyl isocyanate | | 462.2611 |

| 257 | 3-Fluorophenyl isocyanate | | 514.2357 |

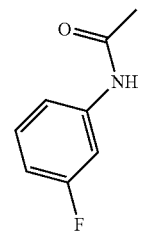

Examples 258-322

The compounds in the table below were prepared and purified according to the methods of Parts B and C of Examples 246-257 using 1-(4-benzylaminobutyl)-2-ethoxymethyl-1H-imidazo[4,5-c]quinolin-4-amine in lieu of 2-methoxymethyl-1-{4-[(pyridin-3-ylmethyl)amino]butyl}-1H-imidazo[4,5-c]quinolin-4-amine. 1-(4-Benzylaminobutyl)-2-ethoxymethyl-1H-imidazo[4,5-c]quinolin-4-amine was prepared according to the general method of Part A of Examples 246-257 using benzaldehyde in lieu of pyridine 3-carboxaldehyde and 1-(4-aminobutyl)-2-ethoxymethyl-1H-imidazo[4,5-c]quinolin-4-amine in lieu of 1-(4-aminobutyl)-2-methoxymethyl-1H-imidazo[4,5-c]quinolin-4-amine. The table below shows the reagent used for each example, the structure of the resulting compound, and the observed accurate mass for the isolated trifluoroacetate salt.

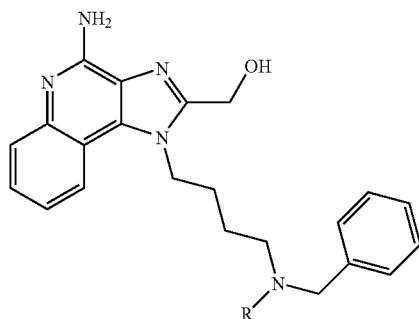
| Example | Reagent | R | Measured Mass (M + H) |
|---|---|---|---|
| 258 | Cyclobutanecarbonyl chloride | | 458.2550 |
| 259 | DL-2-Methylbutyryl chloride | | 460.2707 |
| 260 | Isovaleryl chloride | | 460.2714 |
| 261 | Pentanoyl chloride | | 460.2730 |
| 262 | Pivaloyl chloride | | 460.2714 |
| 263 | Cyclopentanecarbonyl chloride | | 472.2712 |
| 264 | tert-Butylacetyl chloride | | 474.2879 |

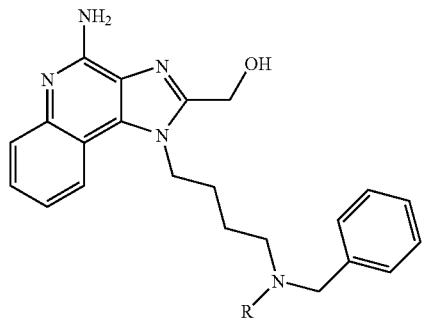
| Example | Reagent | R | Measured Mass (M + H) |
|---|---|---|---|
| 265 | Benzoyl chloride | benzoyl | 480.2398 |
| 266 | Thiophene-2-carbonyl chloride | thiophene-2-carbonyl | 486.1971 |
| 267 | Cyclohexanecarbonyl chloride | cyclohexanecarbonyl | 486.2893 |
| 268 | Cyclopentylacetyl chloride | cyclopentylacetyl | 486.2818 |
| 269 | m-Toluoyl chloride | m-toluoyl | 494.2577 |
| 270 | o-Toluoyl chloride | o-toluoyl | 494.2531 |

-continued
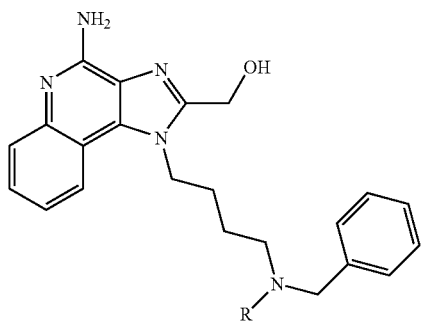
| Example | Reagent | R | Measured Mass (M + H) |
|---|---|---|---|
| 271 | p-Toluoyl chloride | 4-methylbenzoyl | 494.2527 |
| 272 | 3-Fluorobenzoyl chloride | 3-fluorobenzoyl | 498.2307 |
| 273 | 4-Fluorobenzoyl chloride | 4-fluorobenzoyl | 498.2326 |
| 274 | 3-Cyanobenzoyl chloride | 3-cyanobenzoyl | 505.2378 |
| 275 | 4-Cyanobenzoyl chloride | 4-cyanobenzoyl | 505.2387 |

-continued
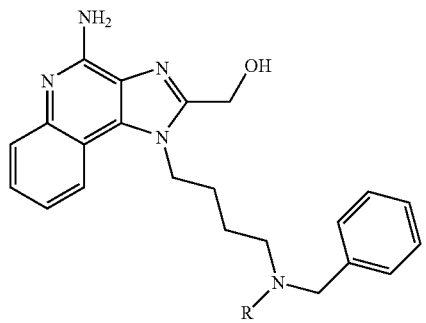
| Example | Reagent | R | Measured Mass (M + H) |
|---|---|---|---|
| 276 | Hydrocinnamoyl chloride | | 508.2715 |
| 277 | 2-Methoxybenzoyl chloride | | 496.2311 |
| 278 | 3-Methoxybenzoyl chloride | | 496.2314 |
| 279 | p-Anisoyl chloride | | 496.2365 |
| 280 | 3-Chlorobenzoyl chloride | | 514.2026 |
| 281 | 4-Chlorobenzoyl chloride | | 514.2041 |

-continued

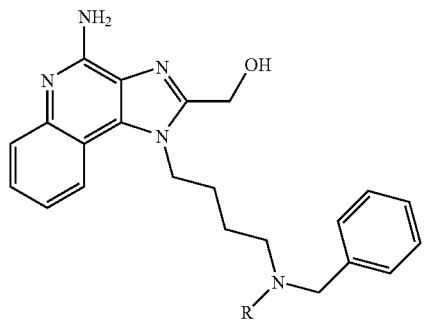

| Example | Reagent | R | Measured Mass (M + H) |
|---|---|---|---|
| 282 | Picolinoyl chloride hydrochloride | 2-pyridinyl-C(=O)– | 481.2361 |
| 283 | trans-2-Phenyl-1-cyclopropanecarbonyl chloride | trans-2-phenylcyclopropyl-C(=O)– | 520.2695 |
| 284 | 4-Dimethylaminobenzoyl chloride | 4-(N,N-dimethylamino)phenyl-C(=O)– | 523.2802 |
| 285 | 1-Propanesulfonyl chloride | CH₃CH₂CH₂-S(O)₂– | 482.2232 |
| 286 | Dimethylsulfamoyl chloride | (CH₃)₂N-S(O)₂– | 483.2196 |
| 287 | 2-Thiophenesulfonyl chloride | 2-thienyl-S(O)₂– | 522.1613 |

-continued
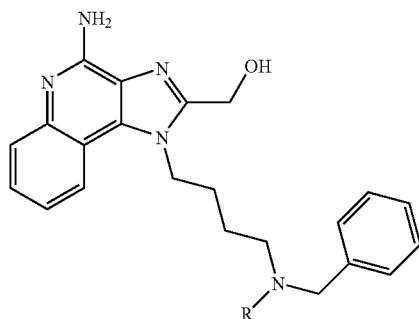
| Example | Reagent | R | Measured Mass (M + H) |
|---|---|---|---|
| 288 | alpha-Toluenesulfonyl chloride | *benzyl-SO2-CH3* | 530.2239 |
| 289 | o-Toluenesulfonyl chloride | *2-methylphenyl-SO2-* | 530.2197 |
| 290 | 4-Fluorobenzenesulfonyl chloride | *4-fluorophenyl-SO2-* | 534.2028 |
| 291 | 3,5-Dimethylisoxazole-4-sulfonyl chloride | *3,5-dimethylisoxazol-4-yl-SO2-* | 535.2106 |
| 292 | 2-Cyanobenzenesulfonyl chloride | *2-cyanophenyl-SO2-* | 541.1968 |
| 293 | 3-Cyanobenzenesulfonyl chloride | *3-cyanophenyl-SO2-* | 541.2035 |

-continued
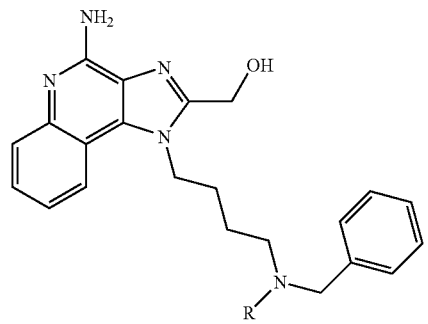
| Example | Reagent | R | Measured Mass (M + H) |
|---|---|---|---|
| 294 | beta-Styrene sulfonyl chloride | | 542.2234 |
| 295 | 3-Methoxybenzenesulfonyl chloride | | 532.2052 |
| 296 | 4-Methoxybenzenesulfonyl chloride | | 532.2037 |
| 297 | 3-Pyridine sulfonyl chloride hydrochloride | | 517.2015 |
| 298 | 2,5-Dimethoxybenzene-sulfonyl chloride | | 548.1964 |

-continued
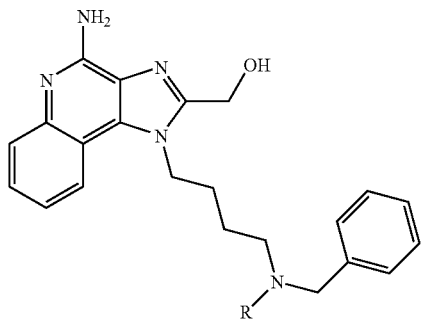
| Example | Reagent | R | Measured Mass (M + H) |
|---|---|---|---|
| 299 | 2,3-Dichlorobenzenesulfonyl chloride | 2,3-dichlorophenylsulfonyl | 584.1294 |
| 300 | 3,5-Dichlorobenzenesulfonyl chloride | 3,5-dichlorophenylsulfonyl | 584.1282 |
| 301 | Methyl isocyanate | C(=O)NHCH₃ | 433.2361 |
| 302 | Ethyl isocyanate | C(=O)NHCH₂CH₃ | 447.2538 |
| 303 | Isopropyl isocyanate | C(=O)NHCH(CH₃)₂ | 461.2663 |
| 304 | n-Propyl isocyanate | C(=O)NHCH₂CH₂CH₃ | 461.2691 |

-continued
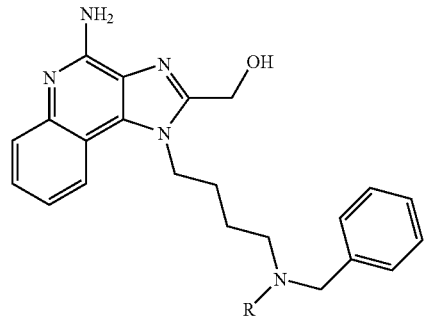
| Example | Reagent | R | Measured Mass (M + H) |
|---|---|---|---|
| 305 | n-Butyl isocyanate | (O=C-NH-CH₂CH₂CH₂CH₃) | 475.2860 |
| 306 | sec-Butyl isocyanate | (O=C-NH-CH(CH₃)CH₂CH₃) | 475.2849 |
| 307 | Pentyl isocyanate | (O=C-NH-(CH₂)₄CH₃) | 489.3005 |
| 308 | Phenyl isocyanate | (O=C-NH-Ph) | 495.2511 |
| 309 | Cyclohexyl isocyanate | (O=C-NH-cyclohexyl) | 501.2978 |

-continued
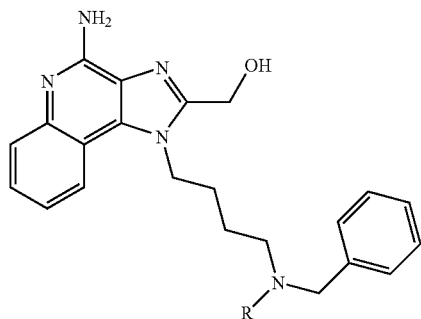
| Example | Reagent | R | Measured Mass (M + H) |
|---|---|---|---|
| 310 | Benzyl isocyanate | (benzyl carbamoyl group) | 509.2675 |
| 311 | 3-Fluorophenyl isocyanate | (3-fluorophenyl carbamoyl) | 513.2467 |
| 312 | 4-Fluorophenyl isocyanate | (4-fluorophenyl carbamoyl) | 513.2388 |
| 313 | Cycloheptyl isocyanate | (cycloheptyl carbamoyl) | 515.3081 |
| 314 | Cyclohexanemethyl isocyanate | (cyclohexylmethyl carbamoyl) | 515.3163 |
| 315 | 4-Cyanophenyl isocyanate | (4-cyanophenyl carbamoyl) | 520.2483 |

-continued
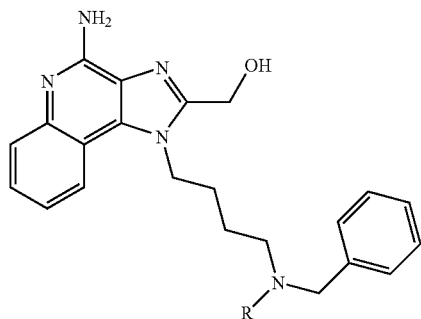
| Example | Reagent | R | Measured Mass (M + H) |
|---|---|---|---|
| 316 | 3,4-Dimethylphenyl isocyanate | | 523.2786 |
| 317 | (S)-(−)-alpha-Methylbenzyl isocyanate | | 523.2786 |
| 318 | 2-Methylbenzyl isocyanate | | 523.2860 |
| 319 | N,N-Dimethylcarbamoyl chloride | | 447.2511 |
| 320 | Diethylcarbamyl chloride | | 475.2828 |
| 321 | 1-Piperidinecarbonyl chloride | | 487.2839 |

-continued

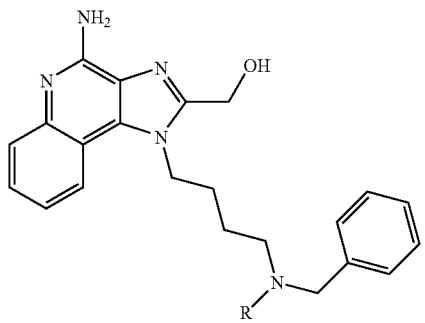

| Example | Reagent | R | Measured Mass (M + H) |
|---|---|---|---|
| 322 | N-(4-Chlorobutyl)-N-methylcarbamyl chloride | (structure shown) | 523.2588 |

Examples 323-329

The compounds in the table below were prepared according to the general method of Examples 111-140. The table shows a reference for the ether starting material, the structure of the resulting compound, and the observed accurate mass for the isolated trifluoroacetate salt.

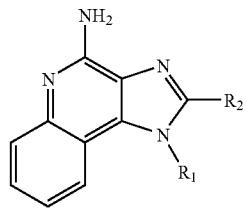

| Example | Reference (ether) | $R_1$ | $R_2$ | Measured Mass (M + H) |
|---|---|---|---|---|
| 323 | U.S. Pat. No 6,667,312* | (structure: propyl-SO₂-CH₃) | —OH (propyl-OH) | 335.1158 |
| 324 | U.S. Pat. No. 6,677,349* | (structure: propyl-NH-SO₂-CH₃) | OH (isopropyl-OH) | 336.1098 |

-continued
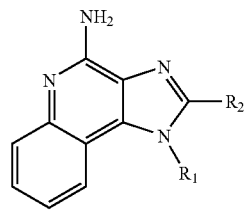
| Example | Reference (ether) | R₁ | R₂ | Measured Mass (M + H) |
|---|---|---|---|---|
| 325 | U.S. Pat. No. 6,677,349* | butyl-NH-SO₂-CH₂CH₃ | -CH₂CH₂OH | 364.1454 |
| 326 | U.S. Pat. No. 6,677,347 Example 57 | -CH₂CH₂CH₂-O-CH₂CH₂-NH-SO₂-CH₃ | -CH₂CH₂OH | 380.1391 |
| 327 | U.S. Pat. No. 6,756,382* | -CH₂CH₂CH₂-NH-C(O)-(3,5-dichlorophenyl) | -CH₂CH₂CH₂OH | 444.0999 |
| 328 | U.S. Pat. No. 6,683,088 Example 1 | -CH₂CH₂CH₂-O-CH₂CH₂-NH-SO₂-CH₃ | -CH₂CH₂CH₂OH | 394.1588 |

-continued

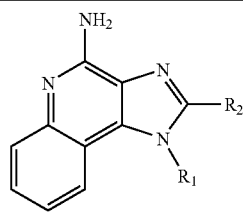

| Example | Reference (ether) | R₁ | R₂ | Measured Mass (M + H) |
|---|---|---|---|---|
| 329 | U.S. Pat. No. 6,677,349 Example 242 | (long chain with NHSO₂Ph) | —OH | 496.2401 |

*Although not specifically exemplified, the compound is readily prepared using the disclosed synthetic methods.

Exemplary Compounds

Certain exemplary compounds, including some of those described above in the Examples, have the following Formula Ib and the following substituents n and $R_1$ wherein each line of the table is matched to Formula Ib to represent a specific embodiment of the invention.

Ib

| n | R₁ |
|---|---|
| 1 | 2-[(cyclohexylcarbonyl)amino]-2-methylpropyl |
| 1 | 2-[(cyclopropylcarbonyl)amino]ethyl |
| 1 | 4-[(cyclopropylcarbonyl)amino]butyl |
| 1 | 2-{[(1-methylethyl)carbonyl]amino}ethyl |
| 1 | 4-{[(1-methylethyl)carbonyl]amino}butyl |
| 1 | 2,2-dimethyl-3-(methylsulfonyl)propyl |
| 1 | 2-methyl-2-({[(1-methylethyl)amino]carbonyl}amino)propyl |
| 1 | 2-methyl-2-[(methylsulfonyl)amino]propyl |
| 1 | 4-[(methylsulfonyl)amino]butyl |
| 1 | 2-[(methylsulfonyl)amino]ethyl |
| 1 | 4-[(4-morpholinecarbonyl)amino]butyl |
| 1 | 2-[(4-morpholinecarbonyl)amino]ethyl |
| 1 | tetrahydro-2H-pyran-4-ylmethyl |
| 2 | 2-[(cyclohexylcarbonyl)amino]-2-methylprpoyl |
| 2 | 2-[(cyclopropylcarbonyl)amino]ethyl |
| 2 | 4-[(cyclopropylcarbonyl)amino]butyl |
| 2 | 2-{[(1-methylethyl)carbonyl]amino}ethyl |
| 2 | 4-{[(1-methylethyl)carbonyl]amino}butyl |
| 2 | 2,2-dimethyl-3-(methylsulfonyl)propyl |
| 2 | 2-methyl-2-({[(1-methylethyl)amino]carbonyl}amino)propyl |
| 2 | 2-methyl-2-[(methylsulfonyl)amino]propyl |
| 2 | 4-[(methylsulfonyl)amino]butyl |
| 2 | 2-[(methylsulfonyl)amino]ethyl |
| 2 | 4-[(4-morpholinecarbonyl)amino]butyl |
| 2 | 2-[(4-morpholinecarbonyl)amino]ethyl |
| 2 | tetrahydro-2H-pyran-4-ylmethyl |

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype calorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response (pg/mL) is the maximal response attained in the dose response curve.

Compounds of the invention and close analogs were tested for their ability to induce cytokine biosynthesis using the test method described above. The analogs used are shown in the table below.

| Analog | Chemical Name | Reference |
|---|---|---|
| 1 | N-[2-(4-Amino-2-methyl-1H-imidazo[4,5-c]quinolin-1-yl)-1,1-dimethylethyl]methanesulfonamide | U.S. Pat. No. 6,677,349[#] |
| 2 | N-[2-(4-Amino-2-ethyl-1H-imidazo[4,5-c]quinolin-1-yl)-1,1-dimethylethyl]methanesulfonamide | U.S. Pat. No. 6,677,349[#] |
| 3 | N-[2-(4-Amino-2-propyl-1H-imidazo[4,5-c]quinolin-1-yl)-1,1-dimethylethyl]methanesulfonamide | U.S. Pat. No. 6,677,349[#] |
| 4 | N-[2-(4-Amino-2-ethoxymethyl-1H-imidazo[4,5-c]quinolin-1-yl)-1,1-dimethylethyl]methanesulfonamide | U.S. Pat. No. 6,677,349 Example 268 |
| 5 | N-{2-[4-Amino-2-(2-methoxyethyl)-1H-imidazo[4,5-c]quinolin-1-yl]-1,1-dimethylethyl}methanesulfonamide | Example 6 Part D |

Figure 2:
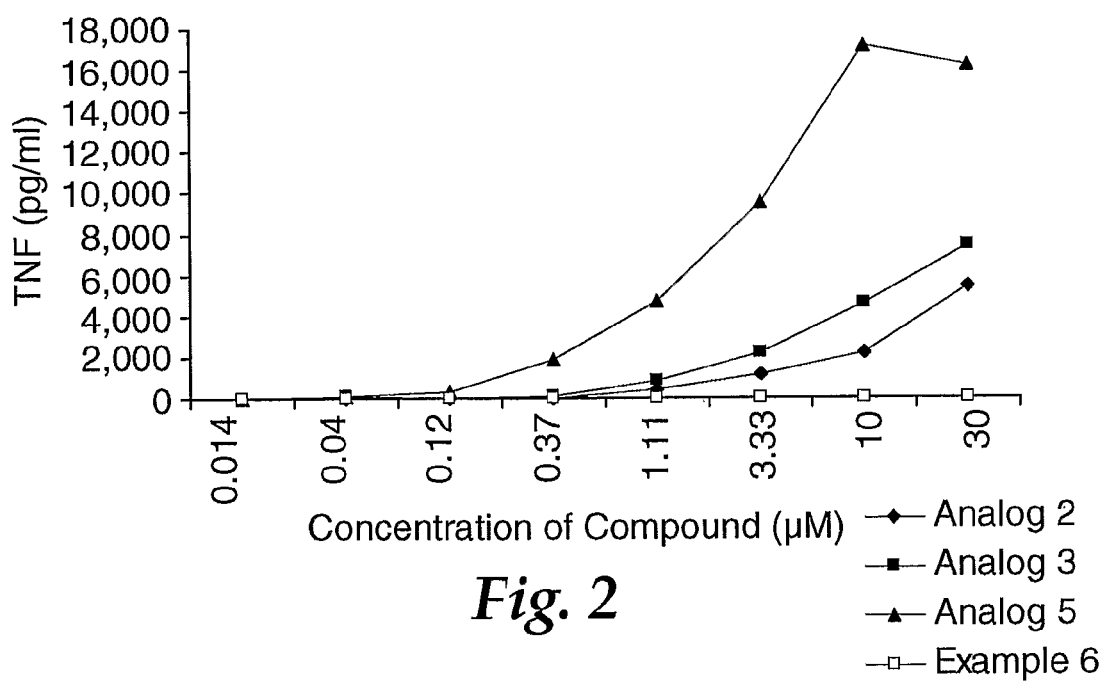
FIG. 2 shows the TNF-α dose response curves (corresponding to values shown in Table 5 below) for Example 6, Analog 2, Analog 3, and Analog 5.
Figure 3:
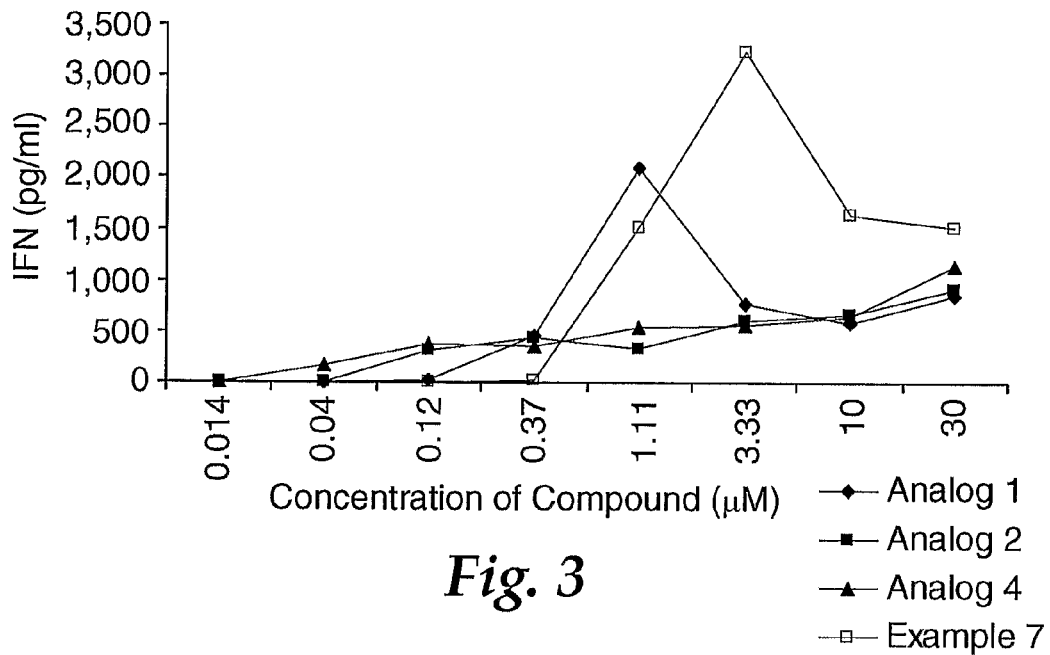
FIG. 3 shows the IFN-α dose response curves (corresponding to values shown in Table 5 below) for Example 7, Analog 1, Analog 2, and Analog 4.
Figure 4:
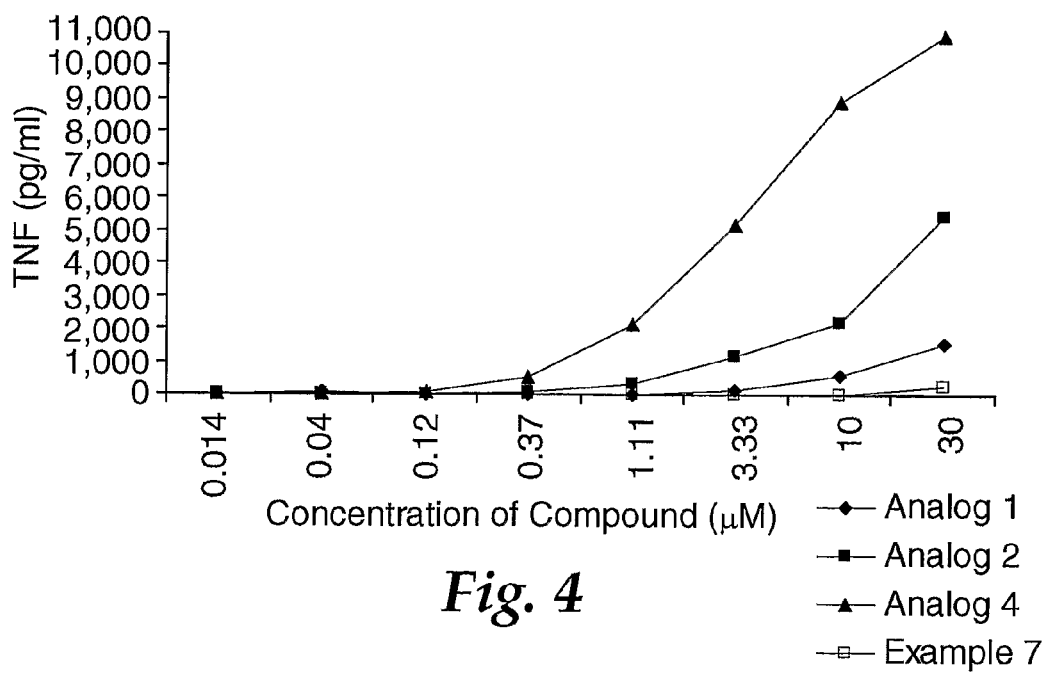
FIG. 4 shows the TNF-α dose response curves (corresponding to values shown in Table 5 below) for Example 7, Analog 1, Analog 2, and Analog 4.

[#]This compound is not specifically exemplified but can be readily prepare using the synthetic methods disclosed in the cited reference The compounds of Examples 6 and 7 and several closely related analogs were tested using the test method described above. The IFN-α dose response curves for Example 6, Analog 2, Analog 3 and Analog 5 are shown in FIG. 1. The TNF-α dose response curves for Example 6, Analog 2, Analog 3 and Analog 5 are shown in FIG. 2. The IFN-α dose response curves for Example 7, Analog 1, Analog 2 and Analog 4 are shown in FIG. 3. The TNF-α dose response curves for Example 7, Analog 1, Analog 2 and Analog 4 are shown in FIG. 4. The minimum effective concentration for the induction of IFN-α, minimum effective concentration for the induction of TNF-α, the maximal response for IFN-α, and the maximal response for TNF-α are shown in Table 5 below where # is the number of separate experiments in which the compound was tested. When a compound was tested in more than one experiment the values shown are the median values.

TABLE 5

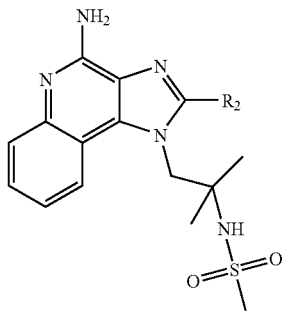

| Compound | R₂ | Minimum Effective Concentration (μM) IFN | TNF | Maximal Response (pg/mL) IFN | TNF | # |
|---|---|---|---|---|---|---|
| Example 7 | —CH₂OH | 3.330 | 30.00 | 2250 | 121 | 5 |
| Example 6 | —(CH₂)₂OH | 1.11 | >30 | 7521 | * | 3 |
| Analog 1 | —CH₃ | 0.370 | 3.330 | 1846 | 1518 | 7 |
| Analog 2 | —CH₂CH₃ | 0.120 | 1.110 | 831 | 3670 | 4 |
| Analog 3 | —(CH₂)₂CH₃ | 0.120 | 0.370 | 832 | 7245 | 9 |

TABLE 5-continued

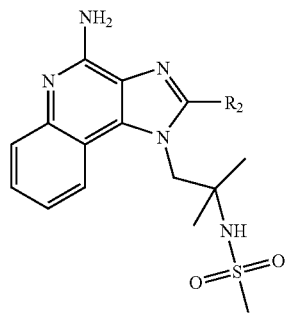

| Compound | R₂ | Minimum Effective Concentration (μM) IFN | TNF | Maximal Response (pg/mL) IFN | TNF | # |
|---|---|---|---|---|---|---|
| Analog 4 | —CH₂OCH₂CH₃ | 0.040 | 0.370 | 889 | 10125 | 22 |
| Analog 5 | —(CH₂)₂OCH₃ | 0.014 | 0.12 | 825 | 12518 | 6 |

*TNF below experimental background of 40 pg/mL.

Compounds of the invention and close analogs were tested for their ability to induce cytokine biosynthesis using the test method described above. The minimum effective concentration for the induction of IFN-α, minimum effective concentration for the induction of TNF-α, the maximal response for IFN-α, and the maximal response for TNF-α are shown in Table 6 below where # is the number of separate experiments in which the compound was tested. When a compound was tested in more than one experiment the values shown are the median values.

TABLE 6

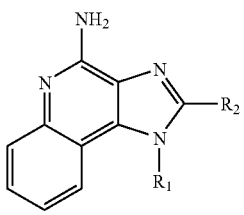

| Compound | R₁ | R₂ | Minimum Effective Concentration (μM) IFN | TNF | Maximal Response (pg/mL) IFN | TNF | # |
|---|---|---|---|---|---|---|---|
| Example 7 | —CH₂C(CH₃)₂NHS(O)₂CH₃ | —CH₂OH | 3.33 | 30 | 1670 | 154 | 6 |
| Example 6 | —CH₂C(CH₃)₂NHS(O)₂CH₃ | —(CH₂)₂OH | 1.11 | 30 | 6527 | * | 4 |
| Analog 1 | —CH₂C(CH₃)₂NHS(O)₂CH₃ | —CH₃ | 0.37 | 3.33 | 1846 | 1518 | 9 |
| Analog 2 | —CH₂C(CH₃)₂NHS(O)₂CH₃ | —CH₂CH₃ | 0.12 | 1.11 | 1096 | 9675 | 6 |
| Analog 3 | —CH₂C(CH₃)₂NHS(O)₂CH₃ | —CH₂CH₂CH₃ | 0.12 | 0.37 | 832 | 9780 | 11 |
| Analog 4 | —CH₂C(CH₃)₂NHS(O)₂CH₃ | —CH₂OCH₂CH₃ | 0.04 | 0.37 | 1138 | 10665 | 33 |
| Analog 5 | —CH₂C(CH₃)₂NHS(O)₂CH₃ | —(CH₂)₂OCH₃ | 0.014 | 0.12 | 1308 | 13908 | 8 |
| Analog 6 | —CH₂C(CH₃)₂NHS(O)₂CH₃ | —CH₂OCH₃ | 0.37 | 3.33 | 1638 | 7151 | 1 |
| Example 147 | —(CH₂)₄NHS(O)₂CH₃ | —CH₂OH | 0.37 | >30 | 7220 | * | 3 |
| Example 3 | —(CH₂)₄NHS(O)₂CH₃ | —(CH₂)₂OH | 0.37 | >30 | 2340 | * | 4 |
| Analog 7 | —(CH₂)₄NHS(O)₂CH₃ | —CH₃ | 0.12 | 10 | 7293 | 526 | 13 |
| Analog 8 | —(CH₂)₄NHS(O)₂CH₃ | —CH₂CH₃ | 0.04 | 3.33 | 2712 | 679 | 79 |
| Analog 9 | —(CH₂)₄NHS(O)₂CH₃ | —CH₂CH₂CH₃ | 0.12 | 1.11 | 2184 | 850 | 22 |
| Analog 10 | —(CH₂)₄NHS(O)₂CH₃ | —CH₂OCH₂CH₃ | 0.04 | 1.11 | 2581 | 1439 | 10 |
| Analog 11 | —(CH₂)₄NHS(O)₂CH₃ | —(CH₂)₂OCH₃ | 0.014 | 0.37 | 7594 | 1931 | 13 |

TABLE 6-continued

[Structure: 4-amino-1H-imidazo[4,5-c]quinoline with R₁ on N1 and R₂ on C2]

| Compound | R₁ | R₂ | Minimum Effective Concentration (μM) IFN | Minimum Effective Concentration (μM) TNF | Maximal Response (pg/mL) IFN | Maximal Response (pg/mL) TNF | # |
|---|---|---|---|---|---|---|---|
| Example 115 | —(CH₂)₄NHC(O)—N(morpholine) | —(CH₂)₂OH | 1.11 | >30 | 8361 | * | 1 |
| Analog 12 | —(CH₂)₄NHC(O)—N(morpholine) | —CH₃ | 0.12 | 10 | 1538 | 1400 | 1 |
| Analog 13 | —(CH₂)₄NHC(O)—N(morpholine) | —CH₂CH₃ | 0.37 | 3.33 | 4975 | 2570 | 1 |
| Analog 14 | —(CH₂)₄NHC(O)—N(morpholine) | —CH₂CH₂CH₃ | 0.12 | 1.11 | 11255 | 1298 | 3 |
| Analog 15 | —(CH₂)₄NHC(O)—N(morpholine) | —CH₂OCH₂CH₃ | 0.12 | 1.11 | 3433 | 1580 | 2 |
| Analog 16 | —(CH₂)₄NHC(O)—N(morpholine) | —(CH₂)₂OCH₃ | 0.014 | 0.04 | 8889 | 3494 | 8 |
| Example 122 | —(CH₂)₃NHS(O)₂CH₃ | —(CH₂)₂OH | 3.33 | >30 | 9651 | * | 3 |
| Analog 17 | —(CH₂)₃NHS(O)₂CH₃ | —CH₃ | 1.11 | 30 | 2778 | * | 11 |
| Analog 18 | —(CH₂)₃NHS(O)₂CH₃ | —CH₂CH₃ | 1.11 | 30 | 1912 | 238 | 2 |
| Analog 19 | —(CH₂)₃NHS(O)₂CH₃ | —CH₂CH₂CH₃ | 1.11 | 10 | 2148 | 109 | 3 |
| Analog 20 | —(CH₂)₃NHS(O)₂CH₃ | —CH₂OCH₂CH₃ | 0.37 | 10 | 1338 | 463 | 9 |
| Analog 21 | —(CH₂)₃NHS(O)₂CH₃ | —(CH₂)₂OCH₃ | 0.014 | 1.11 | 3995 | 954 | 9 |
| Example 131 | —CH₂C(CH₃)₂CH₂NHS(O)₂CH₃ | —(CH₂)₂OH | 0.37 | >30 | 8361 | * | 1 |
| Analog 22 | —CH₂C(CH₃)₂CH₂NHS(O)₂CH₃ | —CH₃ | 0.37 | 10 | 1019 | 805 | 2 |
| Analog 23 | —CH₂C(CH₃)₂CH₂NHS(O)₂CH₃ | —CH₂CH₃ | 0.12 | 3.33 | 1431 | 1453 | 3 |
| Analog 24 | —CH₂C(CH₃)₂CH₂NHS(O)₂CH₃ | —CH₂CH₂CH₃ | 0.12 | 10 | 1711 | 1929 | 2 |
| Analog 25 | —CH₂C(CH₃)₂CH₂NHS(O)₂CH₃ | —CH₂OCH₂CH₃ | 0.12 | 0.37 | 561 | 3768 | 5 |
| Analog 26 | —CH₂C(CH₃)₂CH₂NHS(O)₂CH₃ | —(CH₂)₂OCH₃ | 0.014 | 0.04 | 1805 | 5467 | 10 |
| Example 36 | —(CH₂)₂NHS(O)₂CH₃ | —(CH₂)₂OH | 10 | >30 | 3316 | * | 1 |
| Analog 27 | —(CH₂)₂NHS(O)₂CH₃ | —CH₃ | 0.12 | 10 | 1610 | 820 | 3 |
| Analog 28 | —(CH₂)₂NHS(O)₂CH₃ | —CH₂CH₃ | 0.12 | 10 | 3800 | 2401 | 6 |
| Analog 29 | —(CH₂)₂NHS(O)₂CH₃ | —CH₂CH₂CH₃ | 30 | 10 | 2003 | 11432 | 2 |
| Analog 30 | —(CH₂)₂NHS(O)₂CH₃ | —CH₂OCH₂CH₃ | 0.12 | 3.33 | 1465 | 4918 | 9 |
| Analog 31 | —(CH₂)₂NHS(O)₂CH₃ | —(CH₂)₂OCH₃ | 0.014 | 0.04 | 5858 | 8547 | 6 |
| Example 125 | —(CH₂)₅S(O)₂CH₃ | —(CH₂)₂OH | 0.37 | >30 | 8361 | * | 1 |
| Analog 32 | —(CH₂)₅S(O)₂CH₃ | —CH₃ | 0.37 | 3.33 | 1294 | 771 | 21 |
| Analog 33 | —(CH₂)₅S(O)₂CH₃ | —CH₂CH₃ | 0.12 | 1.11 | 1062 | 1545 | 7 |
| Analog 34 | —(CH₂)₅S(O)₂CH₃ | —CH₂CH₂CH₃ | 0.12 | 1.11 | 828 | 848 | 3 |
| Analog 35 | —(CH₂)₅S(O)₂CH₃ | —(CH₂)₂OCH₃ | 0.014 | 1.11 | 2695 | 6169 | 2 |
| Example 133 | —(CH₂)₂O(CH₂)₂N(CH₃)S(O)₂CH₃ | —(CH₂)₂OH | 0.37 | >30 | 8361 | * | 1 |
| Analog 36 | —(CH₂)₂O(CH₂)₂N(CH₃)S(O)₂CH₃ | —CH₃ | 0.12 | 1.11 | 1001 | 3571 | 1 |
| Analog 37 | —(CH₂)₂O(CH₂)₂N(CH₃)S(O)₂CH₃ | —CH₂CH₃ | 0.12 | 1.11 | 1803 | 2525 | 1 |
| Analog 38 | —(CH₂)₂O(CH₂)₂N(CH₃)S(O)₂CH₃ | —CH₂CH₂CH₃ | 0.37 | 3.33 | 1055 | 1312 | 2 |
| Analog 39 | —(CH₂)₂O(CH₂)₂N(CH₃)S(O)₂CH₃ | —(CH₂)₂OCH₃ | 0.014 | 0.37 | 1630 | 2191 | 4 |
| Example 99 | —(CH₂)₃NHC(O)NHCH(CH₃)₂ | —(CH₂)₂OH | 0.37 | >30 | 21829 | * | 1 |
| Analog 40 | —(CH₂)₃NHC(O)NHCH(CH₃)₂ | —CH₃ | 3.33 | 10 | 1134 | 490 | 1 |
| Analog 41 | —(CH₂)₃NHC(O)NHCH(CH₃)₂ | —CH₂CH₂CH₃ | 0.12 | 1.11 | 6571 | 3740 | 2 |
| Analog 42 | —(CH₂)₃NHC(O)NHCH(CH₃)₂ | —(CH₂)₂OCH₃ | 0.12 | 1.11 | 1289 | 1259 | 1 |
| Example 120 | —(CH₂)₃NH₂ | —(CH₂)₂OH | 3.33 | >30 | 5636 | * | 1 |
| Analog 43 | —(CH₂)₃NH₂ | —CH₃ | 3.33 | >30 | 421 | * | 1 |
| Analog 44 | —(CH₂)₃NH₂ | —CH₂OCH₂CH₃ | 0.12 | 30 | 1325 | 411 | 1 |

TABLE 6-continued

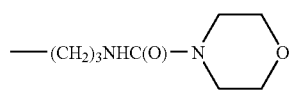

| Compound | $R_1$ | $R_2$ | Minimum Effective Concentration (μM) | | Maximal Response (pg/mL) | | # |
| --- | --- | --- | --- | --- | --- | --- | --- |
| | | | IFN | TNF | IFN | TNF | |
| Analog 45 | —(CH$_2$)$_3$NH$_2$ | —(CH$_2$)$_2$OCH$_3$ | 0.04 | 1.11 | 3433 | 1674 | 1 |
| Example 128 | —(CH$_2$)$_3$NHC(O)—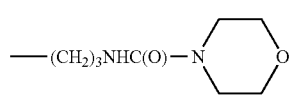 | —(CH$_2$)$_2$OH | 30 | >30 | 75 | * | 3 |
| Analog 46 | —(CH$_2$)$_3$NHC(O)—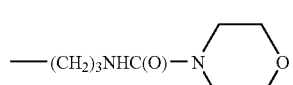 | —CH$_3$ | 0.37 | 30 | 4843 | 463 | 2 |
| Analog 47 | —(CH$_2$)$_3$NHC(O)—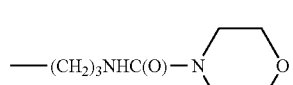 | —CH$_2$OCH$_2$CH$_3$ | 0.12 | 1.11 | 6670 | 1379 | 2 |
| Analog 48 | —(CH$_2$)$_3$NHC(O)—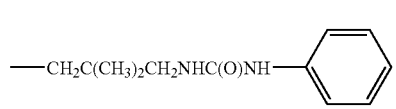 | —(CH$_2$)$_2$OCH$_3$ | 0.014 | 0.014 | 5915 | 6169 | 2 |
| Example 130 | —CH$_2$C(CH$_3$)$_2$CH$_2$NHC(O)NH—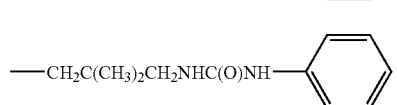 | —(CH$_2$)$_2$OH | 0.014 | 3.33 | 8361 | 2001 | 1 |
| Analog 49 | —CH$_2$C(CH$_3$)$_2$CH$_2$NHC(O)NH— | —CH$_2$CH$_3$ | 0.014 | 0.12 | 922 | 2098 | 2 |
| Analog 50 | —CH$_2$C(CH$_3$)$_2$CH$_2$NHC(O)NH— | —CH$_2$OCH$_2$CH$_3$ | 0.014 | 0.04 | 1133 | 3618 | 2 |
| Analog 51 | —CH$_2$C(CH$_3$)$_2$CH$_2$NHC(O)NH— | —(CH$_2$)$_2$OCH$_3$ | 0.014 | 0.04 | 570 | 6449 | 2 |
| Example 5 | —CH$_2$C(CH$_3$)$_2$NHC(O)— | —CH$_2$OH | 0.37 | 10 | 17274 | 1130 | 1 |
| Analog 52 | —CH$_2$C(CH$_3$)$_2$NHC(O)— | —CH$_2$OCH$_2$CH$_3$ | 0.37 | 0.37 | 1052 | 12173 | 13 |
| Analog 53 | —CH$_2$C(CH$_3$)$_2$NHC(O)— | —CH$_2$OCH$_3$ | 1.11 | 3.33 | 2518 | 9721 | 1 |
| Example 124 | —CH$_2$C(CH$_3$)$_2$CH$_2$NHC(O)— | —(CH$_2$)$_2$OH | 0.12 | 3.33 | 3980 | 1446 | 1 |

TABLE 6-continued

[Structure: 4-amino-1H-imidazo[4,5-c]quinoline core with R₁ on N1 and R₂ at C2]

| Compound | R₁ | R₂ | Minimum Effective Concentration (μM) IFN | TNF | Maximal Response (pg/mL) IFN | TNF | # |
|---|---|---|---|---|---|---|---|
| Analog 54 | —CH₂C(CH₃)₂CH₂NHC(O)—(phenyl) | —CH₂OCH₂CH₃ | 0.04 | 0.37 | 832 | 1820 | 5 |
| Analog 55 | —CH₂C(CH₃)₂CH₂NHC(O)—(phenyl) | —(CH₂)₂OCH₃ | 0.014 | 0.014 | 2133 | 1812 | 1 |
| Example 126 | —(CH₂)₃NHC(O)NH(CH₂)₃CH₃ | —(CH₂)₂OH | 1.11 | >30 | 8361 | * | 1 |
| Analog 56 | —(CH₂)₃NHC(O)NH(CH₂)₃CH₃ | —CH₂OCH₂CH₃ | 0.37 | 3.33 | 827 | 963 | 5 |
| Analog 57 | —(CH₂)₃NHC(O)NH(CH₂)₃CH₃ | —(CH₂)₂OCH₃ | 0.014 | 0.04 | 5915 | 6169 | 2 |
| Example 129 | —CH₂C(CH₃)₂CH₂NH₂ | —(CH₂)₂OH | 0.37 | 30 | 2702 | 85 | 1 |
| Analog 58 | —CH₂C(CH₃)₂CH₂NH₂ | —CH₂CH₃ | 0.04 | 0.37 | 405 | 13846 | 1 |
| Analog 59 | —CH₂C(CH₃)₂CH₂NH₂ | —(CH₂)₂OCH₃ | 0.014 | 0.04 | 571 | 17626 | 1 |
| Example 132 | —(CH₂)₃NHC(O)—(phenyl) | —(CH₂)₂OH | 0.37 | >30 | 8361 | * | 1 |
| Analog 60 | —(CH₂)₃NHC(O)—(phenyl) | —CH₃ | 1.11 | 3.33 | 571 | 156 | 3 |
| Analog 61 | —(CH₂)₃NHC(O)—(phenyl) | —(CH₂)₂OCH₃ | 0.014 | 1.11 | 1504 | 3080 | 2 |
| Example 137 | —(CH₂)₂NHC(O)NHCH₂CH₃ | —(CH₂)₂OH | 30 | 30 | 801 | 73 | 1 |
| Analog 62 | —(CH₂)₂NHC(O)NHCH₂CH₃ | —CH₂CH₃ | 3.33 | 10 | 1031 | 3250 | 2 |
| Analog 63 | —(CH₂)₂NHC(O)NHCH₂CH₃ | —(CH₂)₂OCH₃ | 0.014 | 0.12 | 2587 | 7719 | 4 |
| Example 138 | —(CH₂)₂NHC(O)CH₂CH(CH₃)₂ | —(CH₂)₂OH | 3.33 | >30 | 36 | * | 1 |
| Analog 64 | —(CH₂)₂NHC(O)CH₂CH(CH₃)₂ | —CH₂CH₃ | 3.33 | 30 | 851 | 587 | 2 |
| Analog 65 | —(CH₂)₂NHC(O)CH₂CH(CH₃)₂ | —(CH₂)₂OCH₃ | 0.12 | 3.33 | 1204 | 5694 | 5 |
| Example 142 | —CH₂C(CH₃)₂NHC(O)NHCH(CH₃)₂ | —CH₂OH | 1.11 | >30 | 1554 | * | 1 |
| Analog 66 | —CH₂C(CH₃)₂NHC(O)NHCH(CH₃)₂ | —CH₂CH₃ | 1.11 | 3.33 | 1428 | 6363 | 3 |
| Analog 67 | —CH₂C(CH₃)₂NHC(O)NHCH(CH₃)₂ | —CH₂OCH₂CH₃ | 0.37 | 1.11 | 966 | 10587 | 4 |
| Example 1 | —(CH₂)₃NHS(O)₂—(4-methylphenyl) | —(CH₂)₂OH | 0.37 | 10 | 1072 | 143 | 1 |
| Analog 68 | —(CH₂)₃NHS(O)₂—(4-methylphenyl) | —(CH₂)₂OCH₃ | 0.04 | 0.37 | 638 | 6169 | 2 |
| Example 2 | —(CH₂)₃NHC(O)—(isoquinolin-3-yl) | —(CH₂)₂OH | 3.33 | 3.33 | 507 | 45 | 1 |
| Analog 69 | —(CH₂)₃NHC(O)—(isoquinolin-3-yl) | —(CH₂)₂OCH₃ | 0.12 | 1.11 | 647 | 6169 | 2 |

TABLE 6-continued

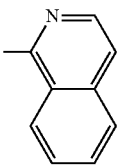

| Compound | R₁ | R₂ | Minimum Effective Concentration (μM) IFN | TNF | Maximal Response (pg/mL) IFN | TNF | # |
|---|---|---|---|---|---|---|---|
| Example 4 | —CH₂C(CH₃)₂NH₂ | —CH₂OH | 0.37 | 3.33 | 1893 | 41 | 2 |
| Analog 70 | —CH₂C(CH₃)₂NH₂ | —CH₂OCH₂CH₃ | 0.12 | 0.37 | 656 | 11475 | 7 |
| Example 111 | —(CH₂)₄NHC(O)— 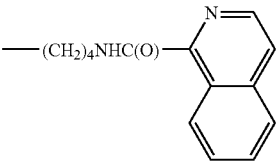 | —(CH₂)₂OH | 0.12 | 1.11 | 7753 | 983 | 1 |
| Analog 71 | —(CH₂)₄NHC(O)— 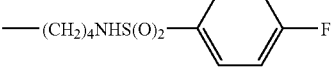 | —(CH₂)₂OCH₃ | 0.014 | 0.04 | 2127 | 1462 | 7 |
| Example 112 | —(CH₂)₄NHS(O)₂— 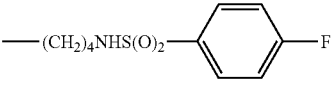—F | —(CH₂)₂OH | 1.11 | 30 | 8361 | 76 | 1 |
| Analog 72 | —(CH₂)₄NHS(O)₂— 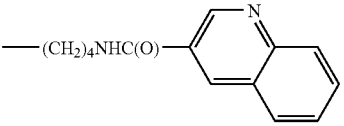—F | —(CH₂)₂OCH₃ | 0.014 | 0.04 | 6032 | 3786 | 4 |
| Example 114 | —(CH₂)₄NH₂ | —(CH₂)₂OH | 30 | >30 | 23 | * | 1 |
| Analog 73 | —(CH₂)₄NH₂ | —(CH₂)₂OCH₃ | 0.04 | 0.37 | 127231 | 724 | 1 |
| Example 116 | —(CH₂)₄NHC(O)— 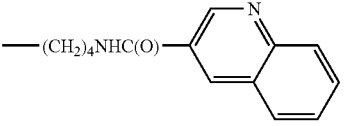 | —(CH₂)₂OH | 0.37 | 30 | 8361 | 1112 | 1 |
| Analog 74 | —(CH₂)₄NHC(O)— 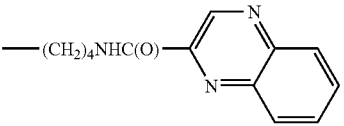 | —(CH₂)₂OCH₃ | 0.014 | 0.04 | 7545 | 9340 | 2 |
| Example 117 | —(CH₂)₄NHC(O)— 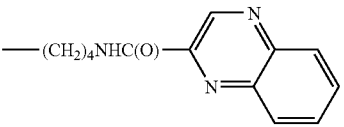 | —(CH₂)₂OH | 0.37 | 3.33 | 5520 | 1938 | 1 |
| Analog 75 | —(CH₂)₄NHC(O)— | —(CH₂)₂OCH₃ | 0.014 | 0.04 | 1129 | 7261 | 3 |

TABLE 6-continued

[Structure: 4-amino-1H-imidazo[4,5-c]quinoline with R₁ on N1 and R₂ on C2]

| Compound | R₁ | R₂ | Minimum Effective Concentration (μM) IFN | Minimum Effective Concentration (μM) TNF | Maximal Response (pg/mL) IFN | Maximal Response (pg/mL) TNF | # |
|---|---|---|---|---|---|---|---|
| Example 118 | —(CH₂)₈NHC(O)NH—phenyl | —(CH₂)₂OH | 0.37 | >30 | 5177 | * | 1 |
| Analog 76 | —(CH₂)₈NHC(O)NH—phenyl | —(CH₂)₂OCH₃ | 0.014 | 0.12 | 1257 | 1372 | 1 |
| Example 119 | —(CH₂)₈NHS(O)₂CH₃ | —(CH₂)₂OH | 0.04 | 3.33 | 8361 | 693 | 1 |
| Analog 77 | —(CH₂)₈NHS(O)₂CH₃ | —(CH₂)₂OCH₃ | 0.014 | 0.014 | 1914 | 1853 | 2 |
| Example 121 | —(CH₂)₈NHC(O)—phenyl | —(CH₂)₂OH | 0.37 | 3.33 | 2441 | 180 | 1 |
| Analog 78 | —(CH₂)₈NHC(O)—phenyl | —(CH₂)₂OCH₃ | 0.014 | 0.014 | 1584 | 1995 | 1 |
| Example 134 | —(CH₂)₂O(CH₂)₂N(CH₃)C(O)—phenyl | —(CH₂)₂OH | 3.33 | 30 | 8361 | 315 | 1 |
| Analog 79 | —(CH₂)₂O(CH₂)₂N(CH₃)C(O)—phenyl | —(CH₂)₂OCH₃ | 0.04 | 0.37 | 1394 | 3317 | 1 |
| Example 135 | —(CH₂)₂O(CH₂)₂N(CH₃)C(O)—cyclohexyl | —(CH₂)₂OH | 3.33 | 30 | 2464 | 146 | 1 |
| Analog 80 | —(CH₂)₂O(CH₂)₂N(CH₃)C(O)—cyclohexyl | —(CH₂)₂OCH₃ | 0.37 | 1.11 | 1234 | 4849 | 2 |
| Example 140 | —(CH₂)₂O(CH₂)₂NHC(O)(CH₂)₁₄CH₃ | —(CH₂)₂OH | 1.11 | >30 | 673 | * | 1 |
| Analog 81 | —(CH₂)₂O(CH₂)₂NHC(O)(CH₂)₁₄CH₃ | —(CH₂)₂OCH₃ | 0.014 | 0.014 | 2556 | 11033 | 9 |
| Example 141 | —(CH₂)₃NHC(O)CH(CH₃)₂ | —(CH₂)₂OH | 0.04 | 30 | 14046 | 243 | 1 |
| Analog 82 | —(CH₂)₃NHC(O)CH(CH₃)₂ | —CH₃ | 1.11 | 10 | 3011 | 405 | 2 |
| Example 143 | —CH₂C(CH₃)₂CH₂S(O)₂CH₃ | —CH₂OH | 1.11 | 30 | 5343 | 164 | 1 |
| Analog 83 | —CH₂C(CH₃)₂CH₂S(O)₂CH₃ | —CH₂OCH₂CH₃ | 0.12 | 0.37 | 1924 | 9513 | 4 |
| Example 144 | —(CH₂)₂NHC(O)NHCH(CH₃)₂ | —CH₂OH | 0.37 | 3.33 | 1488 | 74 | 1 |
| Analog 84 | —(CH₂)₂NHC(O)NHCH(CH₃)₂ | —CH₂OCH₂CH₃ | 0.37 | 10 | 2045 | 7512 | 7 |

*TNF below experimental background of 40 pg/mL

Analogs 1-11, 17-33, 68, 72, and 77 are either specifically exemplified in or are readily prepared using the synthetic methods disclosed in U.S. Pat. Nos. 6,331,539 and 6,677,349.

Analogs 12-16, 40-42, 46-50, 56, 57, 62, 63, 66, and 67 are either specifically exemplified in or are readily prepared using the synthetic methods disclosed in U.S. Pat. Nos. 6,541,485 and 6,573,273.

Analogs 32-35 and 83 are either specifically exemplified in or are readily prepared using the synthetic methods disclosed in U.S. Pat. No. 6,664,264.

Analogs 36-39 are either specifically exemplified in or are readily prepared using the synthetic methods disclosed in U.S. Pat. No. 6,683,088.

Analogs 43-45, 58, 59, 70, and 73 are either specifically exemplified in or are readily prepared using the synthetic methods disclosed in U.S. Pat. Nos. 6,069,149 and 6,677,349.

Analogs 52-55, 60, 61, 64, 65, 69, 71, 74, 75, 78, and 82 are either specifically exemplified in or are readily prepared using the synthetic methods disclosed in U.S. Pat. Nos. 6,451,810 and 6,756,382.

Analogs 79-81 are either specifically exemplified in or are readily prepared using the synthetic methods disclosed in U.S. Pat. No. 6,664,265.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula I:

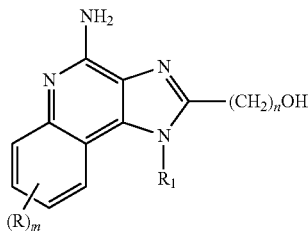

I wherein:
m is 0 or 1;
n is 1 or 2;
R is selected from the group consisting of $C_{1-10}$ alkyl, $C_{1-10}$ alkoxy, halogen, and $C_{1-10}$ haloalkyl;
$R_1$ is selected from the group consisting of:
—X—Y—$R_4$,
—X—$R_5$, and
—X-Het;
X is straight chain or branched chain alkylene optionally interrupted by one —O— group;
Y is selected from the group consisting of —S(O)$_{0-2}$— and —N($R_8$)-Q-;
$R_4$ is selected from the group consisting of hydrogen, alkyl, alkenyl, aryl, arylalkylenyl, heteroaryl, and heteroarylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo;
$R_5$ is selected from the group consisting of:

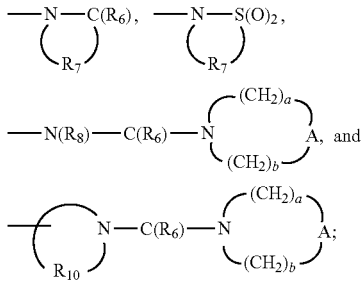

Het is selected from the group consisting of tetrahydropyranyl and tetrahydrofuranyl;

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_{10}$ is $C_{3-8}$ alkylene;
A is selected from the group consisting of —O—, —C(O)—, —CH$_2$—, —S(O)$_{0-2}$—, and —N(Q-$R_4$)—;
Q is selected from the group consisting of a bond, —C($R_6$)—, —S(O)$_2$, —C($R_6$)—N($R_8$)—, —S(O)$_2$—N($R_8$)—, —C($R_6$)—O—, and —C($R_6$)—S—; and
a and b are independently integers from 1 to 6 with the proviso that a+b is <7;
with the proviso that when Y is —S(O)$_{0-2}$— then X can not contain an —O— group;
or a pharmaceutically acceptable salt thereof.

2. The compound or salt of claim 1, wherein n is 1.

3. The compound or salt of claim 1, wherein n is 2.

4. The compound or salt of claim 1, wherein m is 0.

5. The compound or salt of claim 1, wherein $R_1$ is —X—Y—$R_4$ wherein X is straight chain or branched chain $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —S(O)$_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

6. The compound or salt of claim 1, wherein $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino]carbonyl}amino)propyl, and 2,2-dimethyl-3-(methylsulfonyl)propyl.

7. The compound or salt of claim 1, wherein $R_1$ is —X—Y—$R_4$ wherein X is straight chain or branched chain $C_{1-8}$alkylene which may be interrupted by one —O— group; Y is selected from the group consisting of —N($R_8$)—C(O)—, —N($R_8$)—S(O)$_2$—, —N($R_8$)—C(O)—N($R_{8a}$)-, and —S(O)$_2$— wherein $R_8$ is hydrogen, methyl, benzyl, or pyridin-3-ylmethyl; $R_{8a}$ is hydrogen, methyl, or ethyl, and $R_4$ is selected from the group consisting of $C_{1-7}$ alkyl, halo$C_{1-4}$ alkyl, hydroxy$C_{1-4}$alkyl, phenyl, benzyl, 1-phenylethyl, 2-phenylethyl, 2-phenylethenyl, phenylcyclopropyl, pyridinyl, thienyl, N-methylimidazolyl, 3,5-dimethylisoxazolyl, wherein benzyl is unsubstituted or substituted by a methyl group, and phenyl is unsubstituted or substituted by one or two substituents independently selected from the group consisting of methyl, fluoro, chloro, cyano, hydroxy, and dimethylamino.

8. The compound or salt of claim 1, wherein $R_1$ is —X—$R_5$ wherein X is $C_{1-6}$ alkylene, and $R_5$ is

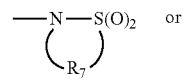

-continued

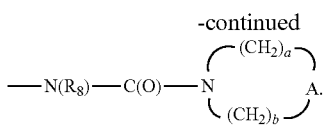

9. The compound or salt of claim 1, wherein $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl.

10. The compound or salt of claim 1, wherein $R_1$ is —$C_{1-4}$alkylenyl-Het.

11. The compound or salt of claim 1, wherein $R_1$ is tetrahydro-2H-pyran-4-ylmethyl.

12. The compound of claim 1, selected from the group consisting of N-[4-(4-amino-2-hydroxymethyl-1H-imidazo[4,5-c]quinolin-1-yl)butyl]methanesulfonamide and N-{4-[4-amino-2-(2-hydroxyethyl)-1H-imidazo[4,5-c]quinolin-1-yl]butyl]}methanesulfonamide, or a pharmaceutically acceptable salt thereof.

13. The compound of claim 1, wherein the compound is N-{2-[4-amino-2-(hydroxymethyl)-1H-imidazo[4,5-c]quinolin-1-yl]-1,1-dimethylethyl}methanesulfonamide or a pharmaceutically acceptable salt thereof.

14. A pharmaceutical composition comprising a therapeutically effective amount of a compound or salt of claim 1 and a pharmaceutically acceptable carrier.

15. A method of preferentially inducing the biosynthesis of IFN-α in an animal comprising administering an effective amount of a compound or salt of claim 1 to the animal.

16. A method of treating a viral disease in an animal in need thereof comprising administering a therapeutically effective amount of a compound or salt of claim 1 to the animal.

17. A method of treating a neoplastic disease in an animal in need thereof comprising administering a therapeutically effective amount of a compound or salt of claim 1 to the animal.

18. The method of claim 15, wherein the compound or salt is administered systemically.

* * * * *